(12) United States Patent
Llinas-Brunet et al.

(10) Patent No.: US 7,749,961 B2
(45) Date of Patent: Jul. 6, 2010

(54) MACROCYCLIC PEPTIDES ACTIVE AGAINST THE HEPATITIS C VIRUS

(75) Inventors: Montse Llinas-Brunet, Dollards des Ormeaux (CA); Murray Bailey, Pierrefonds (CA); Punit K. Bhardwaj, Laval (CA); Francois Bilodeau, Laval (CA); Pasquale Forgione, Montreal (CA); Elise Ghiro, Laval (CA); Nathalie Goudreau, St. Laurent (CA); Teddy Halmos, Laval (CA); Jean Rancourt, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 240 days.

(21) Appl. No.: 11/039,698

(22) Filed: Jan. 19, 2005

(65) Prior Publication Data

US 2005/0192212 A1 Sep. 1, 2005

Related U.S. Application Data

(60) Provisional application No. 60/537,863, filed on Jan. 21, 2004.

(51) Int. Cl.
*A61K 38/12* (2006.01)
(52) U.S. Cl. ...................................................... 514/11
(58) Field of Classification Search ........................ None
See application file for complete search history.

(56) References Cited

U.S. PATENT DOCUMENTS

| | | | |
|---|---|---|---|
| 3,139,421 A | 6/1964 | Elslager et al. |
| 5,114,918 A | 5/1992 | Ishikawa et al. |
| 5,192,746 A | 3/1993 | Lobl et al. |
| 5,633,388 A | 5/1997 | Diana et al. |
| 5,721,210 A | 2/1998 | Lobl et al. |
| 5,824,784 A | 10/1998 | Kinstler et al. |
| 5,830,888 A | 11/1998 | Getman et al. |
| 5,866,684 A | 2/1999 | Attwood et al. |
| 5,869,253 A | 2/1999 | Draper |
| 6,018,020 A | 1/2000 | Attwood et al. |
| 6,159,938 A | 12/2000 | Gyorkos et al. |
| 6,187,905 B1 | 2/2001 | Hurst et al. |
| 6,323,180 B1 | 11/2001 | Llinas-Brunet et al. |
| 6,534,523 B1 | 3/2003 | Llinas-Brunet et al. |
| 6,608,027 B1 | 8/2003 | Tsantrizos et al. |
| 6,767,991 B1 | 7/2004 | Llinas-Brunet et al. |
| 6,828,301 B2 | 12/2004 | Chen et al. |
| 6,867,185 B2 | 3/2005 | Campbell et al. |
| 6,869,964 B2 | 3/2005 | Campbell et al. |
| 6,878,722 B2 | 4/2005 | Campbell et al. |
| 7,119,072 B2 | 10/2006 | Llinas-Brunet et al. |
| 7,157,424 B2 | 1/2007 | Chen et al. |
| 7,173,004 B2 | 2/2007 | McPhee et al. |
| 2003/0181363 A1 | 9/2003 | Llinas Brunet et al. |
| 2003/0224977 A1 | 12/2003 | Llinas Brunet et al. |
| 2004/0002448 A1 | 1/2004 | Tsantrizos et al. |
| 2004/0038872 A1 | 2/2004 | Campbell et al. |
| 2004/0138109 A1 | 7/2004 | Chen et al. |
| 2004/0248779 A1 | 12/2004 | Dersch et al. |
| 2005/0020503 A1 | 1/2005 | Llinas-Brunet et al. |
| 2005/0049187 A1 | 3/2005 | Brandenburg et al. |
| 2005/0075279 A1 | 4/2005 | Llinas Brunet et al. |
| 2005/0080005 A1 | 4/2005 | Llinas-Brunet et al. |
| 2005/0090432 A1 | 4/2005 | McPhee et al. |
| 2005/0119453 A1 | 6/2005 | Brenner et al. |
| 2005/0154186 A1 | 7/2005 | Gallou et al. |
| 2005/0192212 A1 | 9/2005 | Llinas-Brunet et al. |
| 2005/0209135 A1 | 9/2005 | Busacca et al. |
| 2005/0215423 A1 | 9/2005 | Brenner et al. |
| 2006/0063915 A1 | 3/2006 | Gallou et al. |
| 2006/0063916 A1 | 3/2006 | Gallou |
| 2006/0089300 A1 | 4/2006 | Llinas-Brunet et al. |

FOREIGN PATENT DOCUMENTS

| | | |
|---|---|---|
| CA | 2087021 A1 | 1/1992 |
| CA | 2222524 A1 | 1/1997 |
| EP | 0937459 A2 | 8/1999 |
| EP | 1256628 A2 | 11/2002 |
| GB | 2337262 | 11/1999 |
| JP | 1135478 | 2/1999 |
| JP | 11127861 | 5/1999 |
| JP | 11137252 | 5/1999 |

(Continued)

OTHER PUBLICATIONS

Tsantrizos, Y.S., Macrocyclic Inhibitors of the NS3 Protease as Potential Therapeutic Agents of Hepatitis C Virus Infection.; Angew. Chem Int. Ed., (2003) 42 (12): 1356-1360.

(Continued)

*Primary Examiner*—Cecilia Tsang
*Assistant Examiner*—Christina Marchetti Bradley
(74) *Attorney, Agent, or Firm*—Michael P. Morris; Mary-Ellen M. Devlin; Philip I. Datlow

(57) ABSTRACT

Compounds of formula (I):

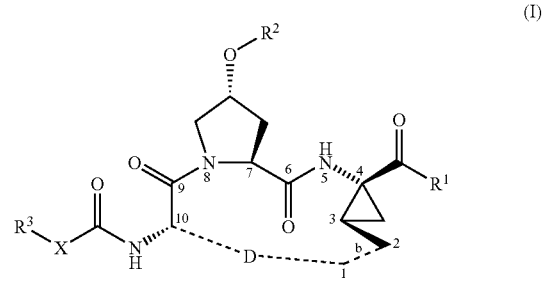

wherein $R^1$, $R^2$, X, $R^3$, D, and the dotted line b are as defined herein; or a pharmaceutically acceptable salt or ester thereof, are useful as inhibitors of the HCV NS3 protease.

46 Claims, No Drawings

FOREIGN PATENT DOCUMENTS

| | | |
|---|---|---|
| JP | 11292840 | 5/1999 |
| JP | 10298151 | 4/2001 |
| JP | 2001103993 | 4/2001 |
| WO | 9200995 A1 | 1/1992 |
| WO | 9415958 A2 | 7/1994 |
| WO | 9533764 A2 | 12/1995 |
| WO | 9701579 A2 | 1/1997 |
| WO | 9706804 A1 | 2/1997 |
| WO | 9950230 A1 | 10/1997 |
| WO | 9743310 A1 | 11/1997 |
| WO | 9817679 A1 | 4/1998 |
| WO | 9822496 A2 | 5/1998 |
| WO | 9846597 A1 | 10/1998 |
| WO | 9846630 A1 | 10/1998 |
| WO | 9853814 A1 | 12/1998 |
| WO | 9907733 A2 | 2/1999 |
| WO | 9907734 A2 | 2/1999 |
| WO | 9938888 A2 | 8/1999 |
| WO | 9964442 A1 | 12/1999 |
| WO | 0006529 A1 | 2/2000 |
| WO | 0009543 A2 | 2/2000 |
| WO | 0009558 A1 | 2/2000 |
| WO | 0020400 A1 | 4/2000 |
| WO | 0031129 A1 | 6/2000 |
| WO | 0059929 A1 | 10/2000 |
| WO | WO 00/59929 | 10/2000 |
| WO | 0102424 A2 | 1/2001 |
| WO | 0107407 A1 | 2/2001 |
| WO | 0116357 A2 | 3/2001 |
| WO | 0132691 A1 | 5/2001 |
| WO | 0140262 A1 | 6/2001 |
| WO | 0147883 A1 | 7/2001 |
| WO | 0158929 A1 | 8/2001 |
| WO | 0164678 A2 | 9/2001 |
| WO | 0174768 A2 | 10/2001 |
| WO | 0177113 A2 | 10/2001 |
| WO | 0181325 A2 | 11/2001 |
| WO | 0185172 A1 | 11/2001 |
| WO | 0190121 A2 | 11/2001 |
| WO | 0206246 A1 | 1/2002 |
| WO | 0208187 A1 | 1/2002 |
| WO | 0208198 A2 | 1/2002 |
| WO | 0208244 A2 | 1/2002 |
| WO | 0208251 A2 | 1/2002 |
| WO | 0208256 A2 | 1/2002 |
| WO | 0218369 A2 | 3/2002 |
| WO | 02057287 A2 | 7/2002 |
| WO | 02057425 A2 | 7/2002 |
| WO | 02060926 A2 | 8/2002 |
| WO | 02069903 A2 | 9/2002 |
| WO | 02079234 A1 | 10/2002 |
| WO | 02098424 A1 | 12/2002 |
| WO | 02100846 A1 | 12/2002 |
| WO | 02100851 A2 | 12/2002 |
| WO | 03000254 A1 | 1/2003 |
| WO | 03007945 A1 | 1/2003 |
| WO | 03010140 A2 | 2/2003 |
| WO | 03010141 A2 | 2/2003 |
| WO | 03026587 A2 | 4/2003 |
| WO | 03053349 A2 | 7/2003 |
| WO | WO 03/053349 | 7/2003 |
| WO | 03064416 A1 | 8/2003 |
| WO | 03064456 A1 | 8/2003 |
| WO | WO 03/064455 A2 | 8/2003 |
| WO | WO 03/066103 | 8/2003 |
| WO | 03099274 A1 | 12/2003 |
| WO | 03099316 A1 | 12/2003 |
| WO | 2004032827 A2 | 4/2004 |
| WO | WO 2004/037855 A1 | 5/2004 |
| WO | WO 2004/039833 A1 | 5/2004 |
| WO | 2004093915 A1 | 11/2004 |
| WO | 2005028501 A1 | 3/2005 |
| WO | 2005046712 A1 | 5/2005 |
| WO | 2005056182 A1 | 6/2005 |

OTHER PUBLICATIONS

Wieland et al.; Amanita Toxins. XVII. Attempted syntheses of phalloine-like cyclopeptides; Ann. 1959, 626: 154-173.
Steinkuhler et al.; Product Inhibition of the Hepatitis C Virus NS3 Protease; Biochemistry; vol. 37; 1998; pp. 8899-8905.
Ingallinella et al.; Potent Peptide Inhibitors of Human Hepatitis C Virus NS3 Protease Are Obtained by Optimizing the Cleavage Products; Biochemistry; 1998; vol. 37; pp. 8906-8914.
Chu et al.; Structure of Sch 68631: A New Hepatitis C Virus Proteinase Inhibitor from Streptomyces sp.; Tetrahedron Letters;1996; vol. 37; No. 40; pp. 7229-7232.
Matsumoto et al.; 3D Modeling of HCV Protease and Computer Screening of its Inhibitors; Antiviral Research, 1996, A 23, 30, 1, Abstract 19.
Llinas-Brunet et al.; Peptide-Based Inhibitors of the Hepatitis C Virus Serine Protease; Bioorganic & Medicinal Chemistry Letters; No. 8; 1998; pp. 1713-1718.
Llinas-Brunet et al.; Studies on the C-Terminal of Hexapeptide Inhibitors of the Hepatitis C Virus Serine Protease; Bioorganic & Medicinal Chemistry Letters; No. 8; 1998; pp. 2719-2724.
Huang et al.; Olefin Metathesis-Active Ruthenium Complexes Bearing a Nucleophilic Carbene Ligand; Journal of the American Chemical Society; 1999; vol. 121; pp. 2674-2678.
Kingsbury et al.; A Recyclable Ru-Based Metathesis Catalyst; Journal of the American Chemical Society; 1999; vol. 121; pp. 791-799.
Berge et al.; Pharmaceutical Salts; Journal of Pharmaceutical Sciences; Jan. 1977; vol. 66; No. 1; pp. 1-19.
Website: http://www.hcvadvocate.org/pdf/aasId_2002_sp-3pdf; What Have We Learned about Hepatitis C at the 2002 AASLD Conference?; 3rd Part; Alan Franciscus, Editor in Chief at HCV Advocate; Translation by Clara Maltras.
Website: http://www.natap.org/2002/AASLD/day14.htm; Sulkowski; Orally available Hepatitis C Virus (HCV) Proteasse Inhibitor (BILN 2061, Boehringer Ingelheim Pharma) Demonstrates Potent Anti-viral Activity in Persons Infected with HCV Genotype 1; Conference Reports for NATAP; American Association for the Study of Liver Diseases; Nov. 2-5, 2002; Boston, MA.
Lamarre et al.; An NS3 Protease Inhibitor with Antiviral Effects in Humans Infected with Hepatitis C Virus; Nature; vol. 426; Nov. 13, 2003; pp. 186-189.
Foy et al.; Regulation of Interferon Regulatory Factor-3 by the Hepatitis C Virus Serin Protease; Science; vol. 300; May 16, 2003; pp. 1145-1148.
World Health Organization Fact Sheet No. 164; Hepatitis C; Revised Oct. 2000; pp. 1-3.
Hoofnagle; U.S. Department of Health and Human Services; 2004. 12.14: Hepatitis C Research at the National Institute of Health; pp. 1-5.
Flamm; Chronic Hepatitis C Virus Infection; Journal of the American Medical Association; May 14, 2003; vol. 289; No. 18; pp. 2413-2417.
Jackson et al.; Potent alpha 4 beta 1 Peptide Antagonists as Potential Anti-Inflammatory Agents; J. Med. Chem. 1997; vol. 40; pp. 3359-3368.
Krchnak et al.; Polymer-Supported Mitsunobu Ether Formation and its Use in Combinatorial Chemistry; Tetrahedron Letters; vol. 36; No. 35; pp. 6193-6196.
Lohmann, et al; Replication of Subgenomic Hepatitis C Virus RNAs in a Hepatoma Cell Line; Science; Jul. 2, 1999; vol. 285; pp. 110-113.
Miller, et al; Application of Ring-Closing Methathesis to the Synthesis of Rigidified Amino Acids and Peptides; Journal of American Chemical Society; 1996; vol. 118; pp. 9606-9614.
Mitsunobu; The Use of Diethyl Azodicarboxylate and Triphenylphosphine in Synthesis and Transformation of Natural Products; Synthesis (Reviews); pp. 1-28.
Rano, et al; Solid Phase Synthesis of Aryl Ethers via the Mitsunobu Reaction; Tetrahedron Letters; 1995; vol. 36; No. 22; pp. 3789-3792.

Still, et al; Rapid Chromatographic Technique for Preparative Separations with Moderate Resolution; Journal of Organic Chemistry; 1978; vol. 43; No. 14.

Derwent Abstract: AN 2001-435746 [47] (JP2001103993).

Derwent Abstract: AN 1999-040664 [04] (JP10298151).

Derwent Abstract: AN 1999-350322 [30] (JP11127861).

Derwent Abstract: AN 2000-018687 [02] (JP11292840).

Derwent Abstract: AN 1999-186214 [16] (JP11035478).

Derwent Abstract: AN 1999-374374 [32] (JP11137252).

Cappelletti et al.; New Conformationally Constrained Xxx-Pro bicyclic mimetics; Letters in Peptide Science; 1995; vol. 2; pp. 161-164.

Glen et al.; Electron-Impact-Induced Fragmentation of Some Isomeric Cyclopropyl Picolyl and Pyridyl Ketones; Organic Mass Spectrometry; 1975; vol. 10; pp. 913-918.

MACROCYCLIC PEPTIDES ACTIVE AGAINST THE HEPATITIS C VIRUS

This application claims benefit from U.S. Provisional Application 60/537,863, filed Jan. 21, 2004.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulin treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction (henceforth referred to as NS2/3 protease); the second one is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus. In a two day clinical trial, it has been shown that the HCV NS3 protease inhibitor BILN 2061 is effective in rapidly reducing viral loads in patients infected with the hepatitis C virus (*Nature* (2003) 426, p. 186-189), thus providing proof of principle of the clinical antiviral activity of HCV NS3 protease inhibitors.

The NS3 protease has been found to potentially have an additional impact by blocking the IFN-mediated cellular antiviral activity in the infected cell (Foy et al., *Science,* 17 Apr. 2003). This lends credence to a hypothesis that the NS3/NS4A protease may represent a dual therapeutic target, the inhibition of which may both block viral replication and restore Interferon response of HCV infected cells.

Macrocyclic compounds which inhibit the HCV NS3 protease have been described in WO 00/59929 (U.S. Pat. No. 6,608,027), WO 03/053349, WO 03/064455 and WO 2004/037855.

The present invention now provides novel compounds that are inhibitory to the NS3 protease. Furthermore, compounds being active in cell culture are provided.

An advantage of one aspect of the present invention resides in the fact that compounds according to this invention specifically inhibit the NS3 protease and do not show significant inhibitory activity against other serine proteases such as human leukocyte Elastase (HLE), porcine pancreatic Elastase (PPE), or bovine pancreatic chymotrypsin, or cysteine proteases such as human liver Cathepsin B (Cat B).

SUMMARY OF THE INVENTION

Included in the scope of the invention are compounds of formula (I):

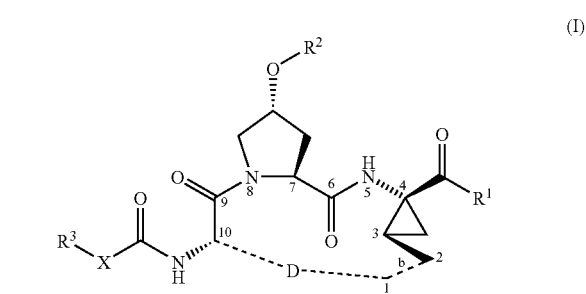

wherein R¹ is hydroxy or NHSO₂R¹¹ wherein R¹¹ is (C₁₋₆)
alkyl, (C₂₋₆)alkenyl, (C₃₋₇)cycloalkyl, (C₃₋₇)cycloalkyl-
(C₁₋₆)alkyl-, aryl, Het, aryl-(C₁₋₄)alkyl-, or Het-(C₁₋₄)
alkyl-;

a) said (C₁₋₆)alkyl, (C₂₋₆)alkenyl, aryl, Het, (C₃₋₇)cy-
cloalkyl-(C₁₋₆)alkyl-, aryl-(C₁₋₄)alkyl-, and Het-(C₁₋₄)
alkyl- optionally being substituted with one, two or three
substituents each independently selected from halogen,
hydroxy, cyano, nitro, (C₁₋₆)alkyl, (C₁₋₆)haloalkyl,
—O—(C₁₋₆)alkyl, —O—(C₁₋₆)haloalkyl, —O-aryl,
—C(=O)—(C₁₋₆)alkyl, —C(=O)—NH₂,
—C(=O)—NH(C₁₋₄)alkyl, —C(=O)—N((C₁₋₄)
alkyl)₂, —NH₂, —NH(C₁₋₄)alkyl and —N((C₁₋₄)
alkyl)₂; and b) said (C₃₋₇)cycloalkyl being optionally substituted with
one or more substituents each independently selected
from nitro, halogen, hydroxy, cyano, —O—(C₁₋₆)alkyl,
(C₂₋₄)alkenyl, —O—(C₁₋₆)haloalkyl, —NH₂, —N
H(C₁₋₄)alkyl, —N((C₁₋₄)alkyl)₂, tri(C₁₋₆)alkylsilyl,
R⁴¹, —C(=O)—R⁴¹, —C(=O)OR⁴¹, —C(=O)N
(R⁴²)R⁴¹, —SO₂R⁴¹, and —OC(=O)—R⁴¹;
wherein R⁴¹ in each case is independently selected from:
i) H, (C₃₋₇)cycloalkyl, (C₄₋₇)cycloalkenyl, Het, or aryl-
(C₁₋₄)alkyl-O—;
ii) aryl or aryloxy, each of which being optionally sub-
stituted with (C₁₋₆)alkyl; and
iii) (C₁₋₆)alkyl optionally substituted with one or more
substituents each independently selected from —O—
(C₁₋₆)alkyl, hydroxy, halogen, (C₂₋₁₀)alkenyl, (C₂₋₁₀)
alkynyl, (C₃₋₇)cycloalkyl, (C₄₋₇)cycloalkenyl, aryl,
Het, aryloxy, and aryl-(C₁₋₄)alkyl-O—, wherein each
of said aryl and aryloxy is optionally substituted with
(C₁₋₆)alkyl; and R⁴² is selected from H and (C₁₋₆)alkyl; or R¹¹ is —N(R¹¹ᵃ)(R¹¹ᵇ), wherein R¹¹ᵃ and R¹¹ᵇ are each inde-
pendently selected from H, (C₁₋₆)alkyl, (C₃₋₇)cycloalkyl,
(C₃₋₇)cycloalkyl-(C₁₋₆)alkyl-, aryl, aryl-(C₁₋₆)alkyl-, Het
and Het-(C₁₋₄)alkyl-; wherein said (C₁₋₆)alkyl, (C₃₋₇)cy-
cloalkyl, (C₃₋₇)cycloalkyl-(C₁₋₆)alkyl-, aryl, aryl-(C₁₋₆)
alkyl-, Het and Het-(C₁₋₄)alkyl- are each optionally substi-
tuted with one or more substituents each independently
selected from halogen, (C₁₋₆)alkyl, hydroxy, cyano, nitro,
(C₁₋₆)haloalkyl, —O—(C₁₋₆)alkyl, —O—(C₁₋₆)haloalkyl,
—NH₂, —NH(C₁₋₄)alkyl, —N((C₁₋₄)alkyl)₂,
—C(=O)—NH₂, —C(=O)—NH(C₁₋₄)alkyl,
—C(=O)—N((C₁₋₄)alkyl)₂, —C(=O)-(C₁₋₆)alkyl,
—COOH, and —COO(C₁₋₆)alkyl; or R¹¹ᵃ and R¹¹ᵇ are linked, together with the nitrogen to
which they are bonded, to form a 3- to 7-membered
monocyclic saturated or unsaturated heterocycle option-
ally fused to at least one other cycle to form a het-
eropolycycle, said heterocycle and heteropolycycle
optionally containing from one to three further heteroa-
toms each independently selected from N, S and O, and
being optionally substituted with one or more substitu-
ents each independently selected from halogen, (C₁₋₆)
alkyl, hydroxy, cyano, nitro, (C₁₋₆)haloalkyl, —O—
(C₁₋₆)alkyl, —O—(C₁₋₆)haloalkyl, —NH₂, —NH
(C₁₋₄)alkyl, —N((C₁₋₄)alkyl)₂, —C(=O)—NH₂,
—C(=O)—NH(C₁₋₄)alkyl, —C(=O)—N((C₁₋₄)
alkyl)₂, —C(=O)—(C₁₋₆)alkyl, —COOH, and —COO
(C₁₋₆)alkyl;

R² is a group of formula:

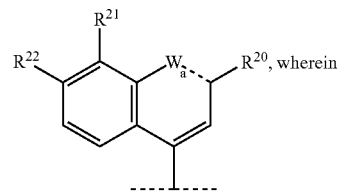

R²⁰ is H, OH, halogen, or Y¹—R²⁰ᵃ wherein Y¹ is a bond,
O, S, or NR²⁰ᵇ and wherein:
R²⁰ᵃ is selected from the group consisting of: (C₁₋₈)
alkyl, (C₁₋₆)alkyl-C=N, (C₂₋₈)alkenyl, (C₂₋₈)alkynyl
and (C₃₋₇)cycloalkyl, each of said alkyl, alkenyl, alky-
nyl and cycloalkyl being optionally substituted with
one, two or three substituents, each independently
selected from:
halogen, (C₁₋₆)alkyl optionally substituted with
—O—(C₁₋₆)alkyl or —O—(C₃₋₆)cycloalkyl,
(C₃₋₇)cycloalkyl, —O—(C₁₋₆)alkyl, Het, —O—
(C₃₋₆)cycloalkyl, —NH₂, —NH(C₁₋₄)alkyl and
—N((C₁₋₄)alkyl)₂; and
R²⁰ᵇ is H, (C₁₋₆)alkyl or (C₃₋₆)cycloalkyl;
and W is N; and the dotted line "a" is a double bond; or
R²⁰ is oxo, and W is NR²³ wherein R²³ is H, (C₁₋₆)alkyl,
(C₂₋₆)alkenyl or (C₂₋₆)alkynyl; and the dotted line "a" is
a single bond;
R²¹ is halogen or Y²—R²¹ᵃ, wherein Y² is a bond, O, S, SO
or SO₂, and R²¹ᵃ is (C₁₋₆)alkyl, (C₂₋₆)alkenyl, (C₂₋₆)
alkynyl, (C₃₋₇)cycloalkyl or (C₃₋₇)cycloalkyl-(C₁₋₆)
alkyl-;
R²² is H, —OH, —O—(C₁₋₄)alkyl, —NH₂, —NH(C₁₋₄)
alkyl or —N((C₁₋₄)alkyl)₂;
or R² is a group of formula:

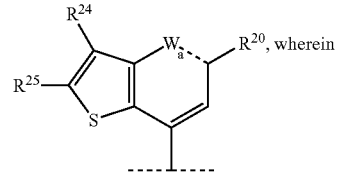

R²⁰, W and the dotted line "a" are as defined above;
R²⁴ is H or R²¹ as defined above; and
R²⁵ is H or (C₁₋₆)alkyl;
X is O or NH;
R³ is (C₁₋₁₀)alkyl, (C₃₋₇)cycloalkyl or (C₃₋₇)cycloalkyl-
(C₁₋₄)alkyl-,
a) wherein the cycloalkyl and cycloalkyl-alkyl- may be
mono-, di- or tri-substituted with (C₁₋₃)alkyl;
b) wherein the alkyl, cycloalkyl and cycloalkyl-alkyl- may
be mono- or di-substituted with substituents each inde-
pendently selected from hydroxy and O—(C₁₋₆)alkyl;
c) wherein each alkyl group may be mono-, di- or tri-
substituted with halogen; and
d) wherein in each cycloalkyl group being 5-, 6- or 7-mem-
bered, one or two —CH₂-groups not being directly
linked to each other may be replaced by —O— such that
the O-atom is linked to the group X via at least two
C-atoms;
D is a 3 to 8 atom saturated or unsaturated alkylene chain; and
the dotted line "b" is a single bond or a double bond;

wherein Het as used herein is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a pharmaceutically acceptable salt or ester thereof;

with the proviso that
when $R^2$ is a group of formula

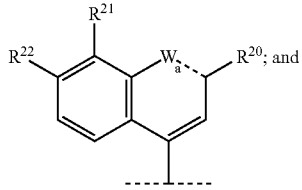

W is N; and the dotted line "a" is a double bond; and
$R^{20}$ is H, halogen, or $Y^1$—$R^{20a}$, wherein $Y^1$ is O and $R^{20a}$ is $(C_{1-6})$alkyl or $(C_{3-6})$cycloalkyl; or $Y^1$ is a bond and $R^{20a}$, is $(C_{1-6})$alkyl; and
$R^{21}$ is halogen or $Y^2$—$R^{21a}$, wherein $Y^2$ is O and $R^{21a}$ is $(C_{1-6})$alkyl or $(C_{3-6})$cycloalkyl; and
$R^{22}$ is H; and
$R^3$ is $(C_{1-6})$alkyl optionally substituted with halo, or $R^3$ is —$(CH_2)_p$—$(C_{3-7})$cycloalkyl wherein p is 0-4, or $R^3$ is a tetrahydrofuran ring linked through the C3 or C4 position of the ring;
then $R^1$ is not $NHSO_2R^{11}$ wherein $R^{11}$ is $(C_{1-6})$alkyl or unsubstituted $(C_{3-7})$cycloalkyl.

Included within the scope of this invention is a pharmaceutical composition comprising an anti-hepatitis C virally effective amount of a compound of formula (I), or a pharmaceutically acceptable salt or ester thereof, in admixture with at least one pharmaceutically acceptable carrier medium or auxiliary agent.

According to a further aspect of this embodiment the pharmaceutical composition as defined above further comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula (I), a pharmaceutically acceptable salt or ester thereof, or a composition as described above, alone or in combination with at least one other antiviral agent, administered together or separately.

Also within the scope of this invention is the use of a compound of formula (I), or a pharmaceutically acceptable salt or ester thereof, as described herein, for the manufacture of a medicament for the treatment or prevention of hepatitis C viral infection in a mammal.

A further aspect of the invention provides the use of a compound of formula (I), or a pharmaceutically acceptable salt or ester thereof, as described herein, in combination with at least one other antiviral agent, for the manufacture of a medicament for the treatment or prevention of hepatitis C viral infection in a mammal.

Still another aspect of this invention relates to a method of inhibiting the replication of hepatitis C virus by exposing the virus to a hepatitis C viral NS3 protease inhibiting amount of the compound of formula (I) according to this invention, or a pharmaceutically acceptable salt thereof.

Yet a further aspect of this invention provides the use of a compound of formula (I), or a pharmaceutically acceptable salt or ester thereof, as described herein, to inhibit the replication of hepatitis C virus.

An additional aspect of this invention refers to an article of manufacture comprising a composition effective to treat an HCV infection or to inhibit the NS3 protease of HCV and packaging material comprising a label which indicates that the composition can be used to treat infection by the hepatitis C virus, wherein said composition comprises a compound of formula (I) according to this invention or a pharmaceutically acceptable salt thereof.

DETAILED DESCRIPTION OF PREFERRED EMBODIMENTS

Definitions

As used herein, the following definitions apply unless otherwise noted: With reference to the instances where (R) or (S) is used to designate the absolute configuration of a substituent or asymmetric center of a compound of formula (I), the designation is done in the context of the whole compound and not in the context of the substituent or asymmetric center alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249-264 (1970)).

As used herein the term "(1R, 2S)-vinyl-ACCA" refers to a compound of formula:

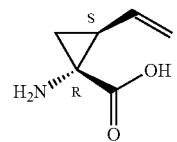

namely, (1R, 2S) 1-amino-2-ethenylcyclopropylcarboxylic acid.

The term "$(C_{x-n})$alkyl" as used herein, either alone or in combination with another substituent, means acyclic, straight or branched chain alkyl substituents containing from x to n carbon atoms, wherein x is 0 (i.e. the alkyl group is absent) or an integer and n is an integer. "$(C_{1-6})$alkyl" (or "lower alkyl") includes, for example, methyl, ethyl, n-propyl, n-butyl, 1-methylethyl (iso-propyl), 1-methylpropyl, 2-methylpropyl, 1,1-dimethylethyl (tert-butyl), pentyl and hexyl. The abbreviation Me denotes a methyl group and, Et denotes ethyl.

The term "$(C_{2-n})$alkenyl" as used herein, either alone or in combination with another substituent, means acyclic, straight or branched chain alkyl substituents containing from 2 to n carbon atoms, wherein n is an integer, at least two of which are linked by a double bond (within the carbon chain or terminal). Examples of $(C_{2-n})$alkenyl include, but are not limited to, ethenyl (vinyl), 1-propenyl, 2-propenyl, and 1-butenyl. The cis and trans isomers, and mixtures thereof, of the $(C_{2-n})$ alkenyl radical can be encompassed by the term. A $(C_{2-n})$ alkenyl radical may be substituted on any of the carbon atoms thereof which would otherwise bear a hydrogen atom.

The term "($C_{2-n}$)alkynyl" as used herein, either alone or in combination with another substituent, means acyclic, straight or branched chain alkyl substituents containing from 2 to n carbon atoms, wherein n is an integer, at least two of which are linked by a triple bond (within the carbon chain or terminal). Examples of such radicals include, but are not limited to, ethynyl, 1-propynyl, 2-propynyl, and 1-butynyl. A ($C_{2-n}$) alkynyl radical may be substituted on any of the carbon atoms thereof which would otherwise bear a hydrogen atom.

The term "($C_{3-m}$)cycloalkyl" as used herein, either alone or in combination with another substituent, means a cycloalkyl substituent containing from 3 to m carbon atoms, wherein m is an integer and includes, but is not limited to, cyclopropyl, cyclobutyl, cyclopentyl, cyclohexyl and cycloheptyl.

The terms "($C_{x-n}$)alkyl-($C_{3-m}$)cycloalkyl" or "($C_{3-m}$)cycloalkyl-($C_{x-n}$)alkyl-" as used herein interchangeably mean an alkylene radical containing from x to n carbon atoms to which a cycloalkyl radical containing from 3 to m carbon atoms, wherein x is 0 (i.e. the alkylene radical is absent) or an integer and n and m are each independently an integer, is directly linked; for example, cyclopropylmethyl, cyclopentylethyl, cyclohexylmethyl, 1-cyclohexylethyl, 2-cyclohexylethyl and cycloheptylpropyl.

The term "aryl" or "($C_{6\ or\ 10}$)aryl" as used herein interchangeably, either alone or in combination with another radical, means either an aromatic monocyclic group containing 6 carbon atoms or an aromatic bicyclic group containing 10 carbon atoms. For example, aryl includes phenyl, 1-naphthyl and 2-naphthyl.

As used herein interchangeably, the terms "($C_{x-n}$)alkyl-($C_{6\ or\ 10}$)aryl" or "($C_{6\ or\ 10}$)aryl-($C_{x-n}$)alkyl-" means an alkyl radical as defined above to which an aryl substituent as defined above is bonded. Examples of ($C_{6\ or\ 10}$)aryl-($C_{1-3}$) alkyl- are benzyl (phenylmethyl), 1-phenylethyl, 2-phenylethyl and phenylpropyl.

The term "O—($C_{1-n}$)alkyl" or "($C_{1-n}$)alkoxy" as used herein interchangeably, either alone or in combination with another radical, means the radical —O—($C_{1-n}$)alkyl wherein alkyl is as defined above containing from 1 to n carbon atoms, and includes methoxy, ethoxy, propoxy, 1-methylethoxy, butoxy and 1,1-dimethylethoxy. The latter radical is known commonly as tert-butoxy. When an —O—($C_{1-n}$)alkyl group is substituted, it is understood to be substituted on the ($C_{1-n}$) alkyl portion thereof.

The term "S—($C_{1-n}$)alkyl" or "($C_{1-n}$)alkylthio" as used herein interchangeably, either alone or in combination with another radical, means the radical —S—($C_{1-n}$)alkyl wherein alkyl is as defined above containing from 1 to n carbon atoms, and includes methylthio, ethylthio, propylthio, 1-methylethylthio, butylthio and 1,1-dimethylethylthio. When an —S—($C_{1-n}$)alkyl group is substituted, it is understood to be substituted on the ($C_{1-n}$)alkyl portion thereof.

The term "halo" or "halogen" as used herein interchangeably, means a halogen substituent selected from fluoro, chloro, bromo or iodo.

The terms "($C_{1-6}$)haloalkyl" or "lower haloalkyl", as used herein interchangeably, mean an alkyl radical containing one to six carbon atoms wherein one or more hydrogen atoms are replaced by a halogen atom (including but not limited to. trifluoromethyl).

The term "oxo" as used herein means an oxygen atom attached as a substituent by a double bond (=O).

As used herein, the term "Het" defines a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic, unless specified otherwise.

As used herein the term "heteroatom" means O, S or N.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms each independently selected from nitrogen, oxygen and sulfur. Examples of such heterocycles include, but are not limited to, azetidine, pyrrolidine, tetrahydrofuran, thiazolidine, pyrrole, thiophene, hydantoin, diazepine, 1H-imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, or the following heterocycles:

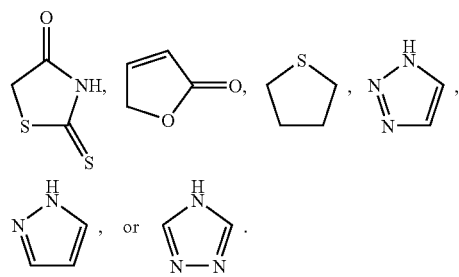

As used herein, the term "heteropolycycle" either alone or in combination with another radical, means a heterocycle as defined above fused to one or more other cycle, be it a heterocycle or any other cycle. Examples of such heteropolycycles include, but are not limited to, indole, benzimidazole, thiazolo[4,5-b]-pyridine, quinoline, isoquinoline, or coumarin, or the following:

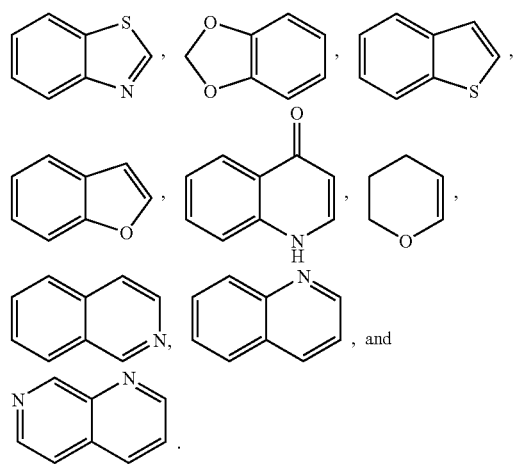

Although generally covered under the term "Het", the term "heteroaryl" as used herein precisely defines an unsaturated heterocycle for which the double bonds form an aromatic system. Suitable examples of "heteroaryl" include but are not limited to: quinoline, indole, pyridine,

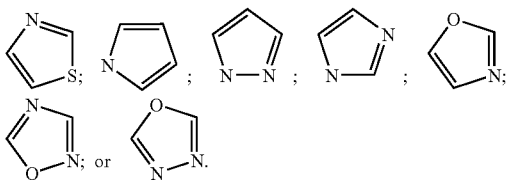

The term "pharmaceutically acceptable ester" as used herein, either alone or in combination with another substituent, means esters of the compound of formula (I) in which any of the carboxyl functions of the molecule, but preferably the carboxy terminus, is replaced by an alkoxycarbonyl function:

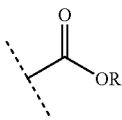

in which the R moiety of the ester is selected from alkyl (e.g. methyl, ethyl, n-propyl, tert-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $(C_{1-4})$alkyl or $(C_{1-4})$alkoxy. Other suitable prodrug esters can be found in Design of prodrugs, Bundgaard, H. Ed. Elsevier (1985). Such pharmaceutically acceptable esters are usually hydrolyzed in vivo when injected in a mammal and transformed into the acid form of the compound of formula (I). With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalene- sulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic non-toxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ-, ω- and τ-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09543, WO 00/09558, WO 00/59929, WO 03/064416, WO 03/064455, WO 03/064456, WO 2004/037855 and co-pending patent application Ser. Nos. 10/850,101 and 60/504,839, herein incorporated by reference in their entirety (all by Boehringer Ingelheim), WO 02/060926, WO 03/053349, WO 03/099316, WO 03/099274, WO 2004/032827 and U.S. 2004/0077551 (all by BMS), WO 2004/072243 (Enanta) and the Vertex clinical candidate identified as VX-950.

The term "inhibitor of HCV polymerase" as used herein means an agent (compound or biological) that is effective to inhibit the function of an HCV polymerase in a mammal. This includes, but is not limited to, non-nucleoside and nucleoside inhibitors of HCV NS5B polymerase.

Examples of inhibitors of HCV polymerase include but are not limited to those compounds described in: WO 02/04425 (Boehringer Ingelheim) WO 03/007945 (Boehringer Ingelheim), WO 03/010140 (Boehringer Ingelheim), WO 03/010141 (Boehringer Ingelheim), WO 2004/064925 (Boehringer Ingelheim), WO 2004/065367 (Boehringer Ingelheim), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates JTK-003 (Japan Tobacco), HCV 086 (ViroPharma/Wyeth), R-803 (Rigel) and NM 283 (Idenix/Novartis).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from a helicase, a NS2/3 protease and an internal ribosome entry site (IRES). Specific examples of inhibitors of another target in the HCV life cycle include ISIS-14803 (ISIS Pharmaceuticals).

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include $\alpha$-, $\beta$-, $\delta$-, $\omega$- and $\tau$-interferons, consensus interferons, asialo-interferons and pegylated forms thereof.

The term "class II interferon" as used herein means an interferon selected from a group of interferons that all bind to receptor type II. Examples of class II interferons include $\gamma$-interferons.

Specific preferred examples of some of these agents are listed below:
  antiviral agents: ribavirin and amantadine;
  immunomodulatory agents: class I interferons, class II interferons and pegylated forms thereof;
  HCV polymerase inhibitors: nucleoside analogs and non-nucleosides;
  inhibitor of another target in the HCV life cycle that inhibits a target selected from: NS3 helicase, NS2/3 protease or internal ribosome entry site (IRES);
  HIV inhibitors: nucleoside inhibitors, non-nucleoside inhibitors, protease inhibitors, fusion inhibitors and integrase inhibitors; or
  HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, an inhibitor of HCV polymerase, another inhibitor of HCV NS3 protease, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood to prevent the appearance of symptoms of the disease and/or to prevent the virus from reaching detectible levels in the blood.

The following sign - - - or → are used interchangeably in sub-formulas to indicate the bond which is connected to the rest of the molecule as defined.

Preferred Embodiments

In the following preferred embodiments, groups and substituents of the compounds according to this invention are described in detail.

Included in the preferred embodiments of the invention are compounds of formula (I) wherein:

$R^1$:

According to one preferred embodiment of the present invention, $R^1$ is hydroxy.

According to an alternative preferred embodiment of the present invention, $R^1$ is $NHSO_2R^{11}$; wherein $R^{11}$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
  a) each of which optionally being mono-, di- or trisubstituted with substituents each independently selected from fluorine and methyl; and
  b) each of which optionally being mono- or disubstituted with substituents each independently selected from hydroxy, trifluoromethyl, methoxy, phenoxy and trifluoromethoxy; and
  c) each of which optionally being monosubstituted with a substituent selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$;
  wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl, and

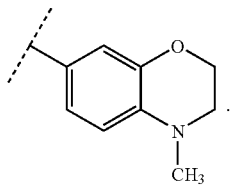

According to another alternative preferred embodiment, $R^1$ is $NHSO_2R^{11}$; wherein $R^{11}$ is selected from cyclopropyl, cyclobutyl, cyclopentyl and cyclohexyl;
  a) each of which optionally being mono-, di- or tri-substituted with fluorine; and
  b) each of which optionally being mono- or disubstituted with substituents selected from hydroxy, methoxy and trifluoromethoxy; and
  c) each of which optionally being monosubstituted with a substituent selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$; and
  d) each of which being optionally substituted with one or more (C$_{1-6}$)alkyl, wherein each (C$_{1-8}$)alkyl is independently optionally substituted with one or more substituents each independently selected from —O—(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O—, wherein each of said aryl and aryloxy is optionally substituted with (C$_{1-6}$)alkyl.

According to yet another alternative preferred embodiment, $R^1$ is $NHSO_2R^{11}$ wherein $R^{11}$ is $N(R^{11a})(R^{11b})$,
  wherein $R^{11a}$ and $R^{11b}$ are each independently selected from H, methyl, ethyl, propyl, 1-methylethyl, cyclopropyl, cyclobutyl, cyclopentyl, cyclohexyl, phenyl and phenylmethyl; wherein said methyl, ethyl, propyl, 1-methylethyl, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or
  $R^{11a}$ and $R^{11b}$ are linked, together with the nitrogen to which they are bonded, to form a 3-4-, 5- or 6-membered monocyclic saturated or unsaturated heterocycle, optionally containing from one to three further heteroatoms each independently selected from N, S and O, and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl.

According to this alternative preferred embodiment, $R^{11a}$ and $R^{11b}$ are more preferably each independently selected from methyl, ethyl, propyl, 1-methylethyl, cyclopropyl, cyclobutyl, cyclopentyl, cyclohexyl, phenyl and phenylmethyl; wherein said methyl, ethyl, propyl, 1-methylethyl, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or
  $R^{11a}$ and $R^{11b}$ are linked, together with the nitrogen to which they are bonded, to form a 3-4-, 5- or 6-membered monocyclic saturated or unsaturated heterocycle, optionally containing from one to three further heteroatoms each independently selected from N, S and O, and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl.

Therefore, more preferably, when $R^1$ is $NHSO_2R^{11}$, the group $R^{11}$ is selected from methyl, ethyl, 1-methylethyl, propyl, ethenyl, cyclopropyl, cyclobutyl, cyclopentyl, phenyl,

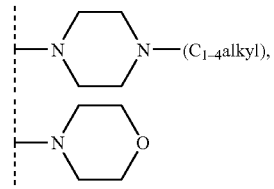

and —N(CH$_3$)$_2$; wherein said phenyl is optionally monosubstituted with halogen and wherein said cyclopropyl is optionally substituted at the 1-position with methyl, ethyl, propyl or butyl, each of said methyl, ethyl, propyl and butyl being optionally further substituted with phenyl, (C$_{3-6}$)cycloalkyl, (C$_{2-6}$)alkenyl or (C$_{1-4}$)alkoxy.

Most preferably, R$^{11}$ is methyl, cyclopropyl, phenyl,

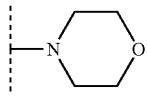

or —N(CH$_3$)$_2$.

R$^2$:

According to a preferred embodiment, R$^2$ is a group of formula:

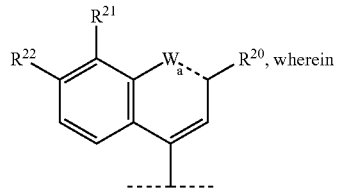, wherein

W, R$^{20}$, R$^{21}$, R$^{22}$ and the dotted line "a" are as defined herein.

According to an alternative preferred embodiment, R$^2$ is a group of formula:

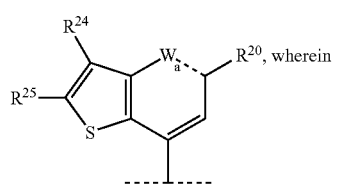, wherein

W, R$^{20}$, R$^{24}$, R$^{25}$ and the dotted line "a" are as defined herein.

W and R$^{20}$:

Preferably, when R$^2$ is a group of formula

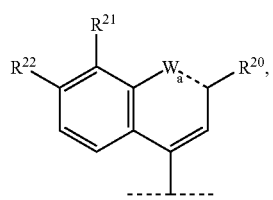

R$^{20}$ is oxo; W is NR$^{23}$ wherein R$^{23}$ is preferably Me, Et, —CH$_2$CH═CH$_2$ or H; and the dotted line "a" is a single bond.

Alternatively preferably, when R$^2$ is a group of formula

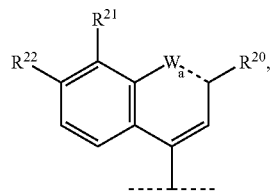

W is N, the dotted line "a" is a double bond; and R$^{20}$ is H, OH, halogen, or Y$^1$—R$^{20a}$, wherein
  Y$^1$ is a bond, O, S, or NR$^{20b}$;
  R$^{20a}$ is selected from the group consisting of: (C$_{1-8}$)alkyl, (C$_{2-8}$)alkenyl, (C$_{2-8}$)alkynyl and (C$_{3-7}$)cycloalkyl, each of said alkyl, alkenyl, alkynyl and cycloalkyl being optionally substituted with one, two or three substituents, each independently selected from:
    halogen, (C$_{1-6}$)alkyl, (C$_{3-7}$)cycloalkyl, Het, —O—(C$_{1-6}$)alkyl, —O—(C$_{3-6}$)cycloalkyl, —NH$_2$, —NH(C$_{1-4}$)alkyl and —N((C$_{1-4}$)alkyl)$_2$; and
  R$^{20b}$ is H, (C$_{1-6}$)alkyl or (C$_{3-6}$)cycloalkyl.

More preferably, when W is N and the dotted line "a" is a double bond, R$^{20}$ is H, (C$_{1-6}$)alkyl, OH, —O—(C$_{1-6}$)alkyl, —S—(C$_{1-6}$)alkyl, —(CH$_2$)$_{0-4}$—CH═CH$_2$, —(CH$_2$)$_{0-4}$—C≡CH, —O—(CH$_2$)$_{0-4}$—CH═CH$_2$, —O—(CH$_2$)$_{0-4}$—C≡CH, —O—(CH$_2$)$_{1-4}$-OMe; —O—(CH$_2$)$_{1-4}$—N(Me)$_2$; —O—(CH$_2$)$_{1-4}$-Het; —S—(CH$_2$)$_{0-4}$—CH═CH$_2$, —S—(CH$_2$)$_{0-4}$—C≡CH, —S—(CH$_2$)$_{1-4}$-OMe; —S—(CH$_2$)$_{1-4}$—N(Me)$_2$, —S—(CH$_2$)$_{1-4}$-Het; (C$_{3-6}$)cycloalkyl, —O—(C$_{3-6}$)cycloalkyl, —O—(C$_{1-6}$)alkyl-(C$_{3-6}$)cycloalkyl, —S—(C$_{3-6}$)cycloalkyl, or —S—(C$_{1-6}$)alkyl-(C$_{3-6}$)cycloalkyl; wherein Het is 5- or 6-membered monocyclic heteroaryl containing from one to three heteroatoms each independently selected from N, O and S;
  each of said (C$_{1-6}$)alkyl, —O—(C$_{1-6}$)alkyl, —S—(C$_{1-6}$)alkyl, —(CH$_2$)$_{0-4}$—CH═CH$_2$, —(CH$_2$)$_{0-4}$—C≡CH, —O—(CH$_2$)$_{0-4}$—CH═CH$_2$, —O—(CH$_2$)$_{0-4}$—C≡CH, —S—(CH$_2$)$_{0-4}$—CH═CH$_2$, —S—(CH$_2$)$_{0-4}$—C≡CH, (C$_{3-6}$)cycloalkyl, —O—(C$_{3-6}$)cycloalkyl, and —S—(C$_{3-6}$)cycloalkyl being optionally substituted with one, two or three substituents, each independently selected from (C$_{1-4}$)alkyl, —O—(C$_{1-4}$)alkyl, and halo;

or R$^{20}$ is NR$^{20a}$R$^{20b}$ wherein R$^{20a}$ is (C$_{1-4}$)alkyl, and R$^{20b}$ is H, (C$_{1-4}$)alkyl or (C$_{3-5}$)cycloalkyl.

Even more preferably R$^{20}$ is H, methyl, ethyl, propyl, 1-methylethyl, butyl, 2-methylpropyl, cyclopropyl, cyclobutyl, cyclopentyl, cyclohexyl, —CH═CH$_2$, —C≡CH, O-methyl, O-ethyl, O-propyl, O—CH(CH$_3$)$_2$, O-cyclopropyl, O-cyclobutyl, O-cyclopentyl, O-cyclohexyl, O—CH$_2$CH$_2$CF$_3$, —O—CH═CH$_2$, —O—CH$_2$—CH═CH$_2$, O—C≡CH, —O—CH$_2$—C≡CH, —O—CH$_2$—C≡CCH$_3$, —O—CH$_2$—CH$_2$-OMe, —O—CH$_2$—CH$_2$—N(Me)$_2$, S-methyl, S-ethyl, S-propyl, S—CH(CH$_3$)$_2$, S-cyclopropyl, S-cyclobutyl, S-cyclopentyl, S-cyclohexyl, —S—CH═CH$_2$, —S—CH$_2$—CH═CH$_2$, S—C≡CH, —S—CH$_2$—C≡CH, —S—CH$_2$—CH$_2$-OMe, —S—CH$_2$—CH$_2$—N(Me)$_2$,

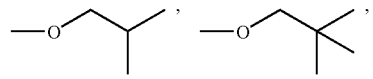

-continued

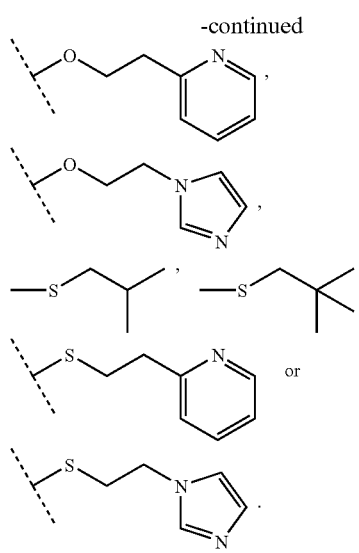

Most preferably R$^{20}$ is H, methyl, ethyl, 1-methylethyl, —C≡CH, O-methyl, O-ethyl, O-propyl, O—CH(CH$_3$)$_2$, O-cyclopentyl, O—CH$_2$CH$_2$CF$_3$, —O—CH=CH$_2$, —O—CH$_2$—CH=CH$_2$, —O—CH$_2$—C≡CH, —O—CH$_2$—C≡CCH$_3$, —O—CH$_2$CH$_2$OMe, —O—CH$_2$CH$_2$N(Me)$_2$, S-methyl, S-ethyl, S-propyl, S—CH(CH$_3$)$_2$,

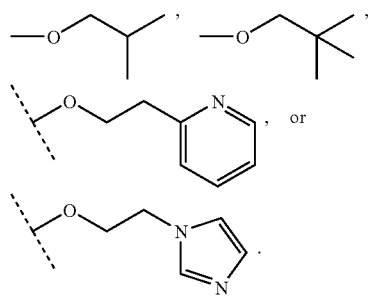

Preferably, when R$^2$ is a group of formula

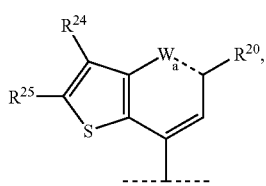

W is N; the dotted line "a" is a double bond; and R$^{20}$ is H, OH, halogen, or Y$^1$—R$^{20a}$ wherein
Y$^1$ is a bond, O, S, or NR$^{20b}$;
R$^{20a}$ is selected from the group consisting of: (C$_{1-8}$)alkyl, (C$_{2-8}$)alkenyl, (C$_{2-8}$)alkynyl and (C$_{3-7}$)cycloalkyl, each of said alkyl, alkenyl, alkynyl and cycloalkyl being optionally substituted with one, two or three substituents, each independently selected from:
halogen, (C$_{1-6}$)alkyl, (C$_{3-7}$)cycloalkyl, Het, —O—(C$_{1-6}$)alkyl, —O—(C$_{3-6}$)cycloalkyl, —NH$_2$, —NH(C$_{1-4}$)alkyl and —N((C$_{1-4}$)alkyl)$_2$; and R$^{20b}$ is H, (C$_{1-6}$)alkyl or (C$_{3-6}$)cycloalkyl.
More preferably, R$^{20}$ is Y$^1$—R$^{20a}$, wherein Y$^1$ is O and R$^{20a}$ is (C$_{1-8}$)alkyl. Most preferably, R$^{20}$ is —O—CH$_2$CH$_3$.
R$^{21}$:
R$^{21}$ is preferably selected from: fluorine, chlorine, bromine, —CH$_3$, —CH$_2$CH$_3$, —CH$_2$CH$_2$CH$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, —(SO)CH$_3$, —(SO)CH$_2$CH$_3$, —(SO)CH$_2$CH$_2$CH$_3$, —(SO$_2$)CH$_3$, —(SO$_2$)CH$_2$CH$_3$, —(SO$_2$)CH$_2$CH$_2$CH$_3$,

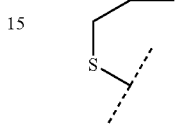

and —C≡CH.
More preferably, R$^{21}$ is selected from: fluorine, chlorine, bromine, —CH$_3$, —OCH$_3$, —SCH$_3$, —SCH$_2$CH$_3$, —(SO)CH$_3$, —(SO$_2$)CH$_3$, —(SO$_2$)CH$_2$CH$_3$,

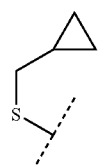

and —C≡CH.
R$^{22}$:
R$^{22}$ is preferably selected from: H, —OH, —OCH$_3$, —OCH$_2$CH$_3$, —OCH$_2$CH$_2$CH$_3$, —NHCH$_3$, —N(CH$_3$)$_2$, —N(CH$_3$)CH$_2$CH$_3$ and —N(CH$_3$)CH$_2$CH$_2$CH$_3$.
More preferably R$^{22}$ is selected from H, —OCH$_3$ and —N(CH$_3$)$_2$.
Most preferably, R$^{22}$ is H or —OCH$_3$.
R$^{24}$:
Preferably, R$^{24}$ is H or (C$_{1-6}$)alkyl. Most preferably, R$^{24}$ is H or CH$_3$.
R$^{25}$:
Most preferably, R$^{25}$ is H.
X:
According to one embodiment of this invention X is O.
According to another embodiment of this invention X is NH.
Preferably, X is O.
R$^3$:
With respect to compounds of formula (I) as defined above, R$^3$ is preferably selected from (C$_{2-8}$)alkyl, (C$_{3-7}$)cycloalkyl and (C$_{3-7}$)cycloalkyl-(C$_{1-3}$)alkyl-,
  a) wherein said cycloalkyl and cycloalkyl-alkyl- may be mono-, di- or tri-substituted with (C$_{1-3}$)alkyl; and
  b) wherein said alkyl, cycloalkyl and cycloalkyl-alkyl- may be mono- or di-substituted with substituents each independently selected from hydroxy and O—(C$_{1-4}$)alkyl; and
  c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O— such that the O-atom is linked to the group X via at least two C-atoms.

R$^3$ is more preferably selected from ethyl, 1-methylethyl, 1,1-dimethylethyl, propyl, 1-methylpropyl, 2-methylpropyl, 1,1-dimethylpropyl, 1,2-dimethylpropyl, 2,2-dimethylpropyl, 1,1,2-trimethylpropyl, 1,2,2-trimethylpropyl, 1-ethylpropyl, 1-ethyl-2-methylpropyl, 1-(1-methylethyl)-2-methylpropyl, 1-ethyl-2,2-dimethylpropyl, butyl, 1-methylbutyl, 2-methylbutyl, 3-methylbutyl, 1,2-dimethylbutyl, 1,1-dimethylbutyl, 1,3-dimethylbutyl, 2,2-dimethylbutyl, 2,3-dimethylbutyl, 3,3-dimethylbutyl, 1,2,2-trimethylbutyl, 1,2,3-trimethylbutyl, 2,3,3-trimethylbutyl and 2,2,3-trimethylbutyl, whereby these alkyl groups may be substituted with chlorine or bromine, or with 1, 2 or 3 fluorine substituents. Examples of preferred fluorinated alkyl groups include, but are not limited to, 2-fluoroethyl, 3-fluoropropyl and 3,3,3-trifluoropropyl.

Alternatively more preferably, R$^3$ is cyclopropyl, cyclobutyl, cyclopentyl, or cyclohexyl or is selected from the following formulas, wherein one or two CH$_2$-groups of a cycloalkyl group is replaced by oxygen:

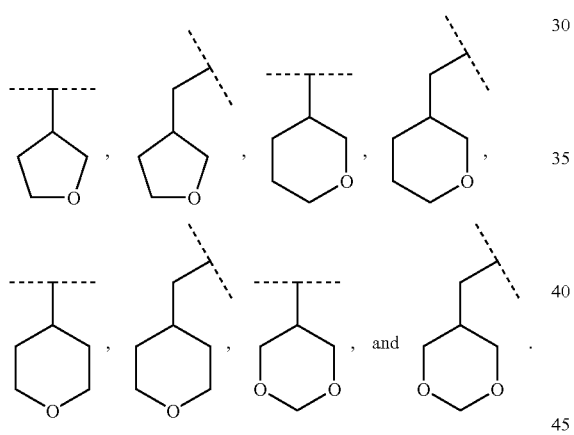

From the above list, cycloalkyl and cycloalkyl-alkyl-groups optionally comprising 1 or 2 O-atoms are optionally substituted with 1, 2 or 3 methyl groups. Especially those cycloalkyl groups, optionally comprising 1 or 2 O-atoms, are preferred, wherein the α-C-atom is substituted with methyl.

Further examples of preferred substituted cyclic groups are

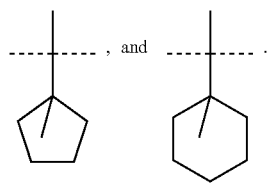

Even more preferred meanings of R$^3$ are cyclopropyl, cyclobutyl, cyclopentyl, cyclohexyl, and a group selected from:

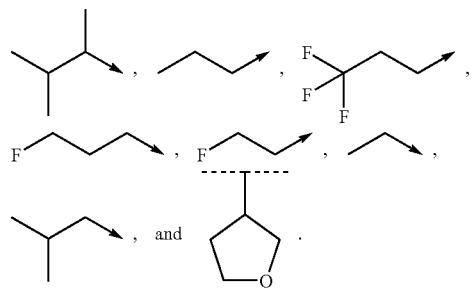

Most preferably R$^3$ is selected from cyclopentyl,

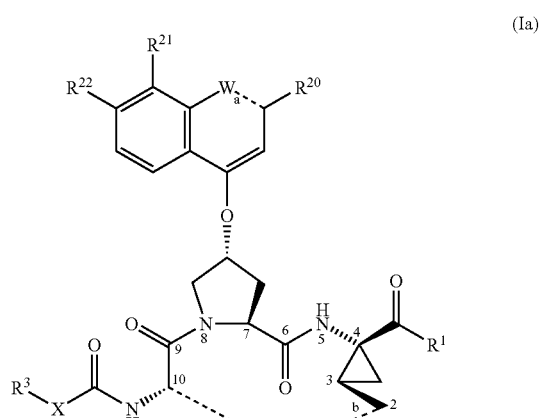

D:

Preferred embodiments of the present invention include compounds of formula (I), wherein linker D is a 3 to 8 atom saturated or unsaturated alkylene chain. More preferably, linker D is a 5 carbon atom chain.

Dotted Line "b":

Preferably the dotted line "b" is a single bond or a double bond. More preferably, the dotted line "b" is a single bond or a double bond in the Z (cis) configuration.

Therefore, according to one embodiment of this invention, compounds are provided of formula (Ia):

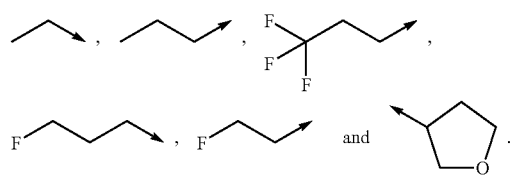

(Ia)

wherein R$^1$ is hydroxy or NHSO$_2$R$^{11}$ wherein R$^{11}$ is (C$_{1-6}$)alkyl, (C$_{3-7}$)cycloalkyl, (C$_{6\ or\ 10}$)aryl, Het, (C$_{3-7}$)cycloalkyl-(C$_{1-6}$)alkyl-, (C$_{6or\ 10}$)aryl-(C$_{1-4}$)alkyl- or Het-(C$_{1-4}$)alkyl-, all of which being optionally mono-, di- or tri-substituted with substituents selected from:
halogen, hydroxy, cyano, nitro, (C$_{1-6}$)alkyl, (C$_{1-6}$)haloalkyl, O—(C$_{1-6}$)alkyl, —O—(C$_{1-4}$)haloalkyl, —C(O)—(C$_{1-6}$)alkyl, —C(O)—NH$_2$, —C(O)—NH(C$_{1-4}$)alkyl, —C(O)—N((C$_{1-4}$)alkyl)$_2$, —NH$_2$, —NH(C$_{1-4}$)alkyl and —N((C$_{1-4}$)alkyl)$_2$;

or R$^{11}$ is —NR$^{11a}$R$^{11b}$ wherein R$^{11a}$ is H or (C$_{1-4}$)alkyl, and R$^{11b}$ is H, (C$_{1-6}$)alkyl, (C$_{3-6}$)cycloalkyl, (C$_{6\,or\,10}$)aryl, Het, (C$_{3-6}$)cycloalkyl-(C$_{1-4}$)alkyl-, (C$_{6\,or\,10}$)aryl-(C$_{1-4}$)alkyl- or Het-(C$_{1-4}$)alkyl-, or R$^{11a}$ and R$^{11b}$ are linked to each other to form a 3 to 7-membered nitrogen-containing ring optionally containing one or two further heteroatoms selected from: O, S or N, all of said R$^{11a}$ and R$^{11b}$ being optionally substituted with:

halogen, hydroxy, cyano, nitro, (C$_{1-6}$)alkyl, (C$_{1-6}$)haloalkyl, O—(C$_{1-6}$)alkyl, —O—(C$_{1-4}$)haloalkyl, —C(O)-(C$_{1-6}$)alkyl, —C(O)—NH$_2$, —C(O)—NH(C$_{1-4}$)alkyl, —C(O)—N((C$_{1-4}$)alkyl)$_2$, —NH$_2$, —NH(C$_{1-4}$)alkyl and —N((C$_{1-4}$)alkyl)$_2$;

R$^{20}$ is H, OH, halogen, or Y$^1$—R$^{20a}$ wherein Y$^1$ is a bond, O, S, or NR$^{20b}$ wherein:

R$^{20a}$ is selected from the group consisting of: (C$_{1-8}$)alkyl, (C$_{1-6}$)alkyl-C≡N, (C$_{2-8}$)alkenyl, (C$_{2-8}$)alkynyl, all of said alkyl, alkenyl and alkynyl being optionally mono- or di-substituted with:

halogen, (C$_{1-6}$)alkyl, —O—(C$_{1-6}$)alkyl, (C$_{1-4}$)alkyl-O—(C$_{1-6}$)alkyl, —O—(C$_{3-6}$)cycloalkyl, (C$_{1-4}$)alkyl-O—(C$_{3-6}$)cycloalkyl, amino, (C$_{1-6}$)alkylamino, or di((C$_{1-6}$)alkyl)amino; and R$^{20b}$ is H, (C$_{1-6}$)alkyl or (C$_{3-6}$)cycloalkyl;

and W is N; and the dotted line "a" is a double bond; or

R$^{20}$ is oxo, and W is NR$^{23}$ wherein R$^{23}$ is H, (C$_{1-6}$)alkyl, (C$_{2-6}$)alkenyl, (C$_{2-6}$)alkynyl; and the dotted line "a" is a single bond;

R$^{21}$ is halogen, (C$_{1-6}$)alkyl, (C$_{2-6}$)alkenyl, (C$_{2-6}$)alkynyl, —O—(C$_{1-6}$)alkyl, —O—(C$_{2-6}$)alkenyl, —O—(C$_{2-6}$)alkynyl, —S—(C$_{1-6}$)alkyl, —S—(C$_{2-6}$)alkenyl, and —S—(C$_{2-6}$)alkynyl, wherein the sulfur is in any oxidized state;

R$^{22}$ is H, —OH, —O—(C$_{1-4}$)alkyl, —NH$_2$, —NH(C$_{1-4}$)alkyl or —N((C$_{1-4}$)alkyl)$_2$;

x is O or NH;

R$^3$ is (C$_{1-10}$)alkyl, (C$_{3-7}$)cycloalkyl, (C$_{3-7}$)cycloalkyl-(C$_{1-4}$)alkyl-,
 a) wherein the cycloalkyl and cycloalkyl-alkyl- may be mono-, di- or tri-substituted with (C$_{1-3}$)alkyl;
 b) wherein the alkyl, cycloalkyl and cycloalkyl-alkyl- may be mono- or di-substituted with substituents selected from hydroxy and O—(C$_{1-6}$)alkyl;
 c) wherein all the alkyl groups may be mono-, di- or tri-substituted with halogen; and
 d) wherein in the cycloalkyl groups, being 5-, 6- or 7-membered, one or two —CH$_2$-groups not being directly linked to each other may be replaced by —O—;

D is a 3 to 8 atom saturated or unsaturated alkylene chain; and the dotted line "b" is a single bond or a double bond;

or a pharmaceutically acceptable salt or ester thereof.

In an alternative preferred embodiment are compounds of formula (I) wherein

R$^1$ is hydroxy or NHSO$_2$R$^{11}$; wherein

R$^{11}$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
 a) each of which optionally being mono-, di- or tri-substituted with substituents each independently selected from fluorine and methyl; and
 b) each of which optionally being mono- or disubstituted with substituents each independently selected from hydroxy, trifluoromethyl, methoxy, phenoxy and trifluoromethoxy; and
 c) each of which optionally being monosubstituted with a substituent selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$;

wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl, and

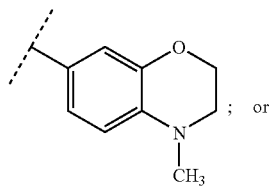

; or

R$^{11}$ is selected from cyclopropyl, cyclobutyl, cyclopentyl and cyclohexyl;
 a) each of which optionally being mono-, di- or tri-substituted with fluorine; and
 b) each of which optionally being mono- or disubstituted with substituents selected from hydroxy, methoxy and trifluoromethoxy; and
 c) each of which optionally being monosubstituted with a substituent selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$; and
 d) each of which being optionally substituted with one or more (C$_{1-8}$)alkyl, wherein each (C$_{1-8}$)alkyl is independently optionally substituted with one or more substituents each independently selected from —O—(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O—, wherein each of said aryl and aryloxy is optionally substituted with (C$_{1-6}$)alkyl; or R$^{11}$ is —N(R$^{11a}$)(R$^{11b}$), wherein R$^{11a}$ and R$^{11b}$ are each independently selected from H, methyl, ethyl, propyl, 1-methylethyl, cyclopropyl, cyclobutyl, cyclopentyl, cyclohexyl, phenyl and phenylmethyl; wherein said methyl, ethyl, propyl, 1-methylethyl, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or R$^{11a}$ and R$^{11b}$ are linked, together with the nitrogen to which they are bonded, to form a 3-4-, 5- or 6-membered monocyclic saturated or unsaturated heterocycle, optionally containing from one to three further heteroatoms each independently selected from N, S and O, and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; and $R^2$ is a group of formula

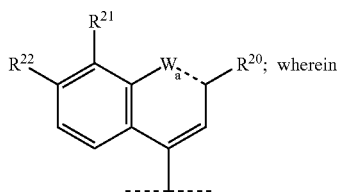

$R^{20}$ is oxo, W is $NR^{23}$ wherein $R^{23}$ is Me, Et, —CH$_2$CH=CH$_2$ or H and the dotted line "a" is a single bond; or W is N, the dotted line "a" is a double bond; and $R^{20}$ is H, OH, halogen, or $Y^1$—$R^{20a}$ wherein $Y^1$ is a bond, O, S, or $NR^{20b}$;

$R^{20a}$ is selected from the group consisting of: $(C_{1-8})$alkyl, $(C_{2-8})$alkenyl, $(C_{2-8})$alkynyl and $(C_{3-7})$cycloalkyl, each of said alkyl, alkenyl, alkynyl and cycloalkyl being optionally substituted with one, two or three substituents, each independently selected from:

halogen, $(C_{1-6})$alkyl, $(C_{3-7})$cycloalkyl, Het, —O—$(C_{1-6})$alkyl, —O—$(C_{3-6})$cycloalkyl, —NH$_2$, —NH$(C_{1-4})$alkyl and —N$((C_{1-4})$alkyl$)_2$; and $R^{20b}$ is H, $(C_{1-6})$alkyl or $(C_{3-6})$cycloalkyl; and $R^{21}$ is selected from: fluorine, chlorine, bromine, —CH$_3$, —CH$_2$CH$_3$, —CH$_2$CH$_2$CH$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, —(SO)CH$_3$, —(SO)CH$_2$CH$_3$, —(SO)CH$_2$CH$_2$CH$_3$, —(SO$_2$)CH$_3$, —(SO$_2$)CH$_2$CH$_3$, —(SO$_2$)CH$_2$CH$_2$CH$_3$,

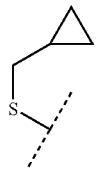

and —C—CH; and $R^{22}$ is selected from: H, —OH, —OCH$_3$, —OCH$_2$CH$_3$, —OCH$_2$CH$_2$CH$_3$, —NHCH$_3$, —N(CH$_3$)$_2$, —N(CH$_3$)CH$_2$CH$_3$ and —N(CH$_3$)CH$_2$CH$_2$CH$_3$;

or R is a group of formula

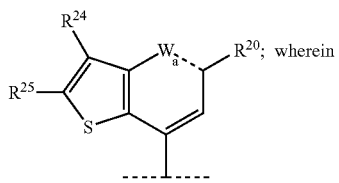

W is N; the dotted line "a" is a double bond; and $R^{20}$ is H, OH, halogen, or $Y^1$—$R^{20a}$ wherein $Y^1$ is a bond, O, S, or $NR^{20b}$;

$R^{20a}$ is selected from the group consisting of: $(C_{1-8})$alkyl, $(C_{2-8})$alkenyl, $(C_{2-8})$alkynyl and $(C_{3-7})$cycloalkyl, each of said alkyl, alkenyl, alkynyl and cycloalkyl being optionally substituted with one, two or three substituents, each independently selected from:

halogen, $(C_{1-6})$alkyl, $(C_{3-7})$cycloalkyl, Het, —O—$(C_{1-6})$alkyl, —O—$(C_{3-6})$cycloalkyl, —NH$_2$, —NH$(C_{1-4})$alkyl and —N$((C_{1-4})$alkyl$)_2$; and $R^{20b}$ is H, $(C_{1-6})$alkyl or $(C_{3-6})$cycloalkyl; and $R^{24}$ is H or $(C_{1-6})$alkyl; and $R^{25}$ is H; and X is O or NH; and $R^3$ is selected from $(C_{2-8})$alkyl, $(C_{3-7})$cycloalkyl and $(C_{3-7})$cycloalkyl-$(C_{1-3})$alkyl-, a) wherein said cycloalkyl and cycloalkyl-alkyl- may be mono-, di- or tri-substituted with $(C_{1-3})$alkyl; and b) wherein said alkyl, cycloalkyl and cycloalkyl-alkyl- may be mono- or di-substituted with substituents each independently selected from hydroxy and O—$(C_{1-4})$alkyl; and c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O— such that the O-atom is linked to the group X via at least two C-atoms; and linker D is a 3 to 8 atom saturated or unsaturated alkylene chain; and the dotted line "b" is a single bond or a double bond.

More preferred are compounds of formula (I) wherein $R^1$ is hydroxy or NHSO$_2$R$^{11}$, wherein $R^{11}$ is selected from methyl, ethyl, 1-methylethyl, propyl, ethenyl, cyclopropyl, cyclobutyl, cyclopentyl, phenyl,

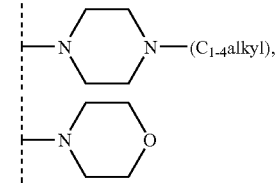

and —N(CH$_3$)$_2$; wherein said phenyl is optionally monosubstituted with halogen and wherein said cyclopropyl is optionally substituted at the 1-position with methyl, ethyl, propyl or butyl, each of said methyl, ethyl, propyl and butyl being optionally further substituted with phenyl, $(C_{3-6})$cycloalkyl, $(C_{2-6})$alkenyl or $(C_{1-4})$alkoxy; and $R^2$ is a group of formula

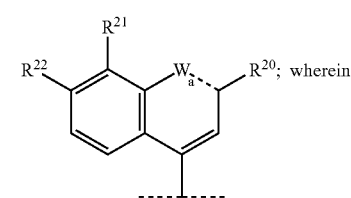

$R^{20}$ is oxo, W is $NR^{23}$ wherein $R^{23}$ is Me, Et, —CH$_2$CH=CH$_2$ or H and the dotted line "a" is a single bond; or W is N; the dotted line "a" is a double bond; and $R^{20}$ is H, $(C_{1-6})$alkyl, OH, —O—$(C_{1-6})$alkyl, —S—$(C_{1-6})$alkyl, —(CH$_2$)$_{0-4}$—CH=CH$_2$, —(CH$_2$)$_{0-4}$—C≡CH, —O—(CH$_2$)$_0$-4-CH=CH$_2$, —O—(CH$_2$)$_{0-4}$-C≡CH, —O—(CH$_2$)$_{1-4}$-OMe; —O—(CH$_2$)$_{1-4}$-N(Me)$_2$; —O—(CH$_2$)$_{14}$-Het; —S—(CH$_2$)$_{0-4}$—CH=CH$_2$, —S—(CH$_2$)$_{0-4}$-C≡CH, —S—(CH$_2$)$_{1-4}$-OMe; —S—(CH$_2$)$_{1-4}$-N(Me)$_2$, —S—(CH$_2$)$_{1-4}$-Het; (C$_{3-6}$)cycloalkyl, —O—(C$_{3-6}$)cycloalkyl, O—(C$_{1-6}$)alkyl-(C$_{3-6}$)cycloalkyl, —S—(C$_{3-6}$)cycloalkyl, or —S—(C$_{1-6}$)alkyl-(C$_{3-6}$)cycloalkyl; wherein Het is 5- or 6-membered monocyclic heteroaryl containing from one to three heteroatoms each independently selected from N, O and S;

each of said (C$_{1-6}$)alkyl, —O—(C$_{1-6}$)alkyl, —S—(C$_{1-6}$)alkyl, —(CH$_2$)$_{0-4}$—CH=CH$_2$, —(CH$_2$)$_{0-4}$C≡CH, —O—(CH$_2$)$_{0-4}$-CH=CH$_2$, —O—(CH$_2$)$_{0-4}$—C≡CH, —S—(CH$_2$)$_{0-4}$—CH=CH$_2$, S—(CH$_2$)$_{0-4}$-C≡CH, (C$_{3-6}$)cycloalkyl, —O—(C$_{3-6}$)cycloalkyl, and —S—(C$_{3-6}$)cycloalkyl being optionally substituted with one, two or three substituents, each independently selected from (C$_{1-4}$)alkyl, —O—(C$_{1-4}$)alkyl, and halo;

or R$^{20}$ is NR$^{20a}$R$^{20b}$ wherein R$^{20a}$ is (C$_{1-4}$)alkyl, and R$^{20b}$ is H, (C$_{1-4}$)alkyl or (C$_{3-5}$)cycloalkyl; and R$^{21}$ is selected from: fluorine, chlorine, bromine, —CH$_3$, —CH$_2$CH$_3$, —CH$_2$CH$_2$CH$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, —(SO)CH$_3$, —(SO)CH$_2$CH$_3$, —(SO)CH$_2$CH$_2$CH$_3$, —(SO$_2$)CH$_3$, —(SO$_2$)CH$_2$CH$_3$, —(SO$_2$)CH$_2$CH$_2$CH$_3$,

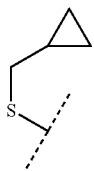

and —C≡CH; and

R$^{22}$ is selected from H, —OCH$_3$ and —N(CH$_3$)$_2$;

or R$^2$ is a group of formula

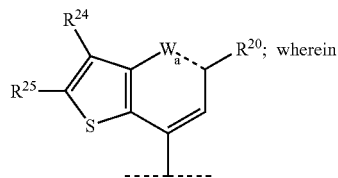

W is N; the dotted line "a" is a double bond;
R$^{20}$ is Y$^1$—R$^{20a}$ wherein Y$^1$ is O and R$^{20a}$ is (C$_{1-8}$)alkyl;
R$^{24}$ is H or (C$_{1-6}$)alkyl; and
R$^{25}$ is H; and X is O or NH: and R$^3$ is selected from cyclopropyl, cyclobutyl, cyclopentyl, cyclohexyl, and a group selected from:

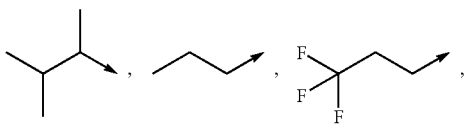

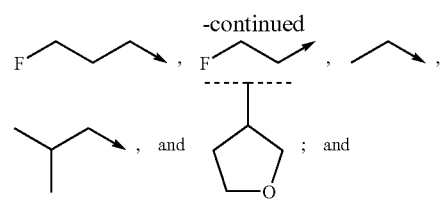

linker D is a 3 to 8 atom saturated or unsaturated alkylene chain; and the dotted line "b" is a single bond or a double bond.

Most preferred are compounds of formula (I) wherein

R$^1$ is hydroxy or NHSO$_2$R$^{11}$, wherein R$^{11}$ is methyl, cyclopropyl, phenyl,

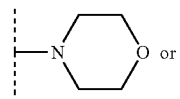

—N(CH$_3$)$_2$; and

R$^2$ is a group of formula

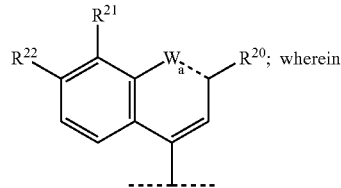

R$^{20}$ is oxo, W is NR$^{23}$ wherein R$^{23}$ is Me, Et, —CH$_2$CH=CH$_2$ or H and the dotted line "a" is a single bond; or W is N, the dotted line "a" is a double bond, and R$^{20}$ is H, methyl, ethyl, 1-methylethyl, —C≡CH, O-methyl, O-ethyl, O— propyl, O—CH(CH$_3$)$_2$, O-cyclopentyl, O—CH$_2$CH$_2$CF$_3$, —O—CH=CH$_2$, —O—CH$_2$—CH=CH$_2$, —O—CH$_2$—C≡CH, —O—CH$_2$—C≡CCH$_3$, —O—CH$_2$CH$_2$OMe, —O—CH$_2$CH$_2$N(Me)$_2$, S-methyl, S-ethyl, S-propyl, S—CH(CH$_3$)$_2$,

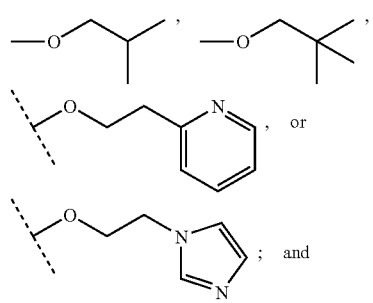

R$^{21}$ is selected from fluorine, chlorine, bromine, —CH$_3$, —OCH$_3$, —SCH$_3$,
—SCH$_2$CH$_3$, (SO)CH$_3$, (SO$_2$)CH$_3$, —(SO$_2$)CH$_2$CH$_3$,

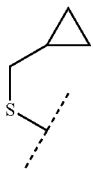

and —C≡CH; and
R$^{22}$ is H or —OCH$_3$; or
R$^2$ is a group of formula

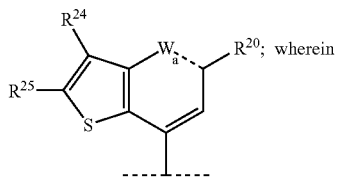; wherein

W is N; the dotted line "a" is a double bond;
R$^{20}$ is —O—CH$_2$CH$_3$;
R$^{24}$ is H or CH$_3$; and
R$^{25}$ is H; and
X is O; and
R$^3$ is selected from cyclopentyl,

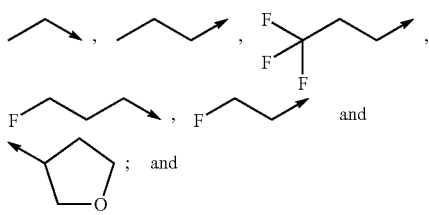

linker D is a 5 carbon atom chain; and
the dotted line "b" is a single bond or a double bond in the Z (cis) configuration.

Specific Examples of Preferred Embodiments

Examples of most preferred compounds according to this invention are each single compound listed in Tables 1 to 5 below.

Pharmaceutical Composition:

Included within the scope of this invention is a pharmaceutical composition comprising an anti-hepatitis C virally effective amount of a compound of formula (I), or a pharmaceutically acceptable salt or ester thereof, in admixture with at least one pharmaceutically acceptable carrier medium or auxiliary agent.

According to a further aspect of this embodiment the pharmaceutical composition as defined above further comprises a therapeutically effective amount of at least one other antiviral agent.

According to an alternate embodiment, the pharmaceutical composition of this invention may additionally comprise at least one other anti-HCV agent. Examples of anti-HCV agents include, α- (alpha), β-(beta), δ- (delta), γ- (gamma), ω- (omega) or τ- (tau) interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula (I) and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds, including their pharmaceutically acceptable salts and esters thereof, are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α- (alpha), β- (beta), δ-(delta), ω- (omega), γ- (gamma) or τ- (tau)-interferon, ribavirin, amantadine; other inhibitors of HCV NS3 protease; inhibitors of HCV polymerase; inhibitors of other targets in the HCV life cycle, which include but are not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula (I), including a pharmaceutically acceptable salt or ester thereof.

In a preferred embodiment, this method is useful in decreasing the NS3 protease activity of the hepatitis C virus infecting a mammal.

Still another embodiment of this invention provides the use of a compound of formula (I), or a pharmaceutically acceptable salt or ester thereof, to inhibit HCV NS3 protease activity.

As discussed above, combination therapy is contemplated wherein a compound of formula (I), or a pharmaceutically acceptable salt or ester thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

A compound of formula (i), or a pharmaceutically acceptable salt or ester thereof, set forth herein may also be used as a laboratory reagent. Furthermore a compound of this invention, including a pharmaceutically acceptable salt or ester thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt or ester thereof, set forth herein may also be used as a research reagent. A compound of formula (I), including a pharmaceutically acceptable salt or ester thereof, may also be used as positive control to validate surrogate cell-based assays or in vitro or in vivo viral replication assays.

Methodology

In general, the compound of formula (I) and intermediates therefore are prepared by known methods using reaction conditions which are known to be suitable for the reactants. Several such methods are disclosed in WO 00/09543, WO 00/09558, WO 00/59929 and in co-pending application Ser. No. 10/945,518, all of which are incorporated herein by reference.

Particularly, the synthesis of the P3 fragment ((2S)-N-protected-amino non-8-enoic acid) and the P1 fragment ((1R, 2S) 1-amino-2-ethenylcyclopropylcarboxylic acid) have been described in detail in WO 00/59929.

I. General Multi-Step Synthetic Method

In general, the present invention is directed to compounds of formula (i) which can be prepared by a general multi-step synthetic method. Specifically, compounds of the following formula (Ib) are prepared by the following process:

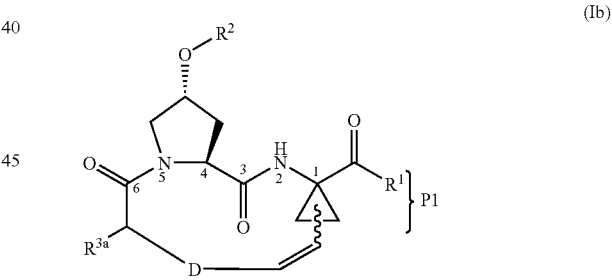

(Ib)

wherein P1, $R^1$, $R^2$, and D are as defined herein and wherein $R^{3a}$ is defined as —NHC(=O)—X—$R^3$, wherein X and $R^3$ are as defined herein, said process comprising the following steps:

(i) reacting a compound of formula (II):

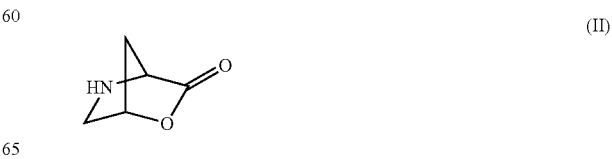

(II)

or a salt thereof, with a compound of formula (III):

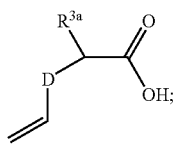
(III)

(ii) reacting the resulting compound of formula (IV) obtained in step (i):

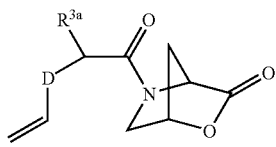
(IV)

with an aminocyclopropane compound of formula (V)

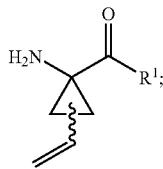
(V)

(iii) reacting the resulting compound of formula (VI) obtained in step (ii):

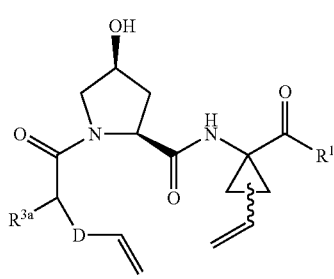
(VI)

with a compound of formula (VII):

LG—SO$_2$—R$^{12}$ (VII)

wherein LG represents a suitable leaving group and R$^{12}$ is selected from p-tolyl, p-bromophenyl, p-nitrophenyl, methyl, trifluoromethyl, perfluorobutyl and 2,2,2-trifluoroethyl;

iv) cyclizing of the resulting diene compound of formula (VIII) obtained in step (iii):

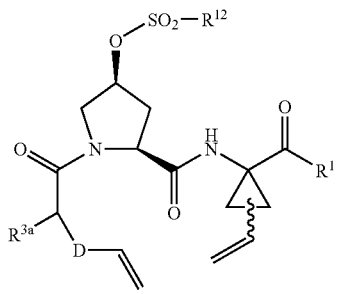
(VIII)

in the presence of a ruthenium catalyst; and (v) reacting the resulting compound of formula (IX) obtained in step (iv):

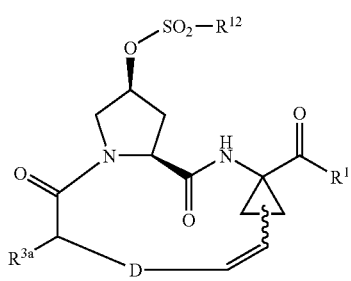
(IX)

with a compound of formula (X):
wherein R$^2$ is selected from

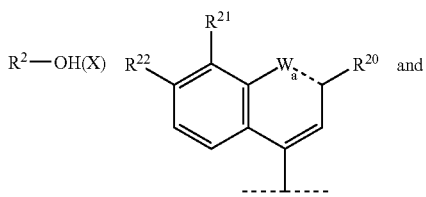 and

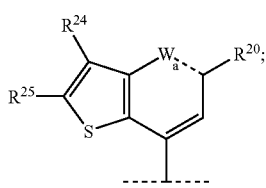

wherein W, $R^{20}$, $R^{21}$, $R^{22}$, $R^{24}$, $R^{25}$ and the dotted line a are as defined herein; to obtain a compound of formula (Ib):

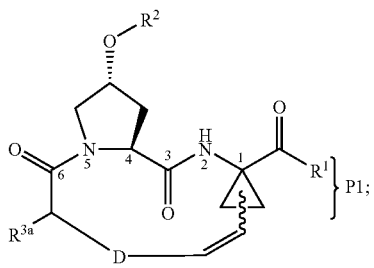

(Ib)

and when $R^1$ is a carboxylic acid ester group in the resulting compound of formula (Ib), optionally subjecting the compound of formula (Ib) to hydrolysis conditions to obtain a compound of formula (I) wherein $R^1$ is a carboxylic acid group.

II. Sulfonamides and Sulfamides

Compounds of formula (I) wherein $R^1$ is $NHSO_2R^{11}$ as defined herein are prepared by coupling the corresponding acid of formula (I) (i.e. $R^1$ is hydroxy) with an appropriate sulfonamide or sulfamide of formula $R^{11}$—$SO_2NH_2$ in the presence of a coupling agent under standard conditions. Although several commonly used coupling agents can be employed, TBTU and HATU have been found to be practical. The sulfonamides are available commercially or can be prepared by known methods.

III. Alternative Methodology

The following scheme provides an alternative process using known methods for preparing a key intermediate of formula 1h from acyclic intermediates:

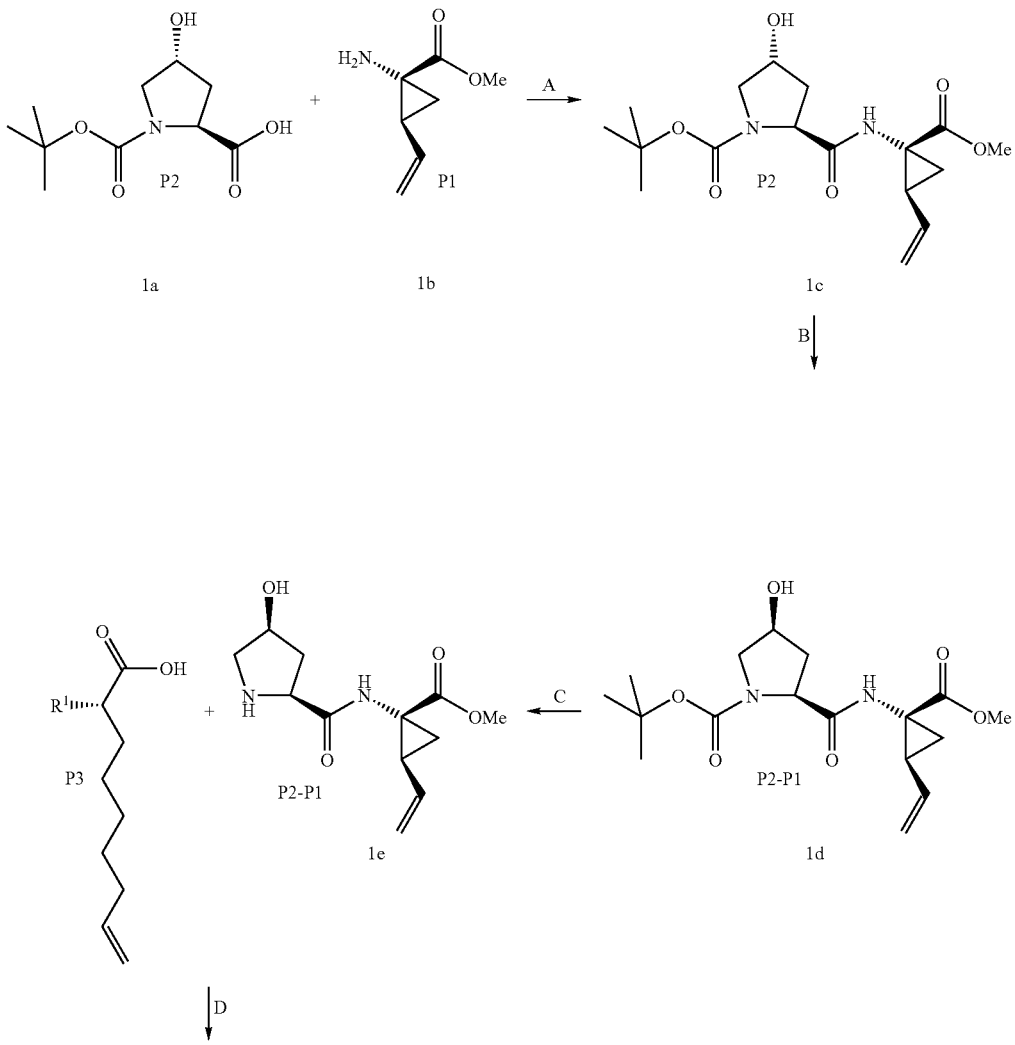

-continued

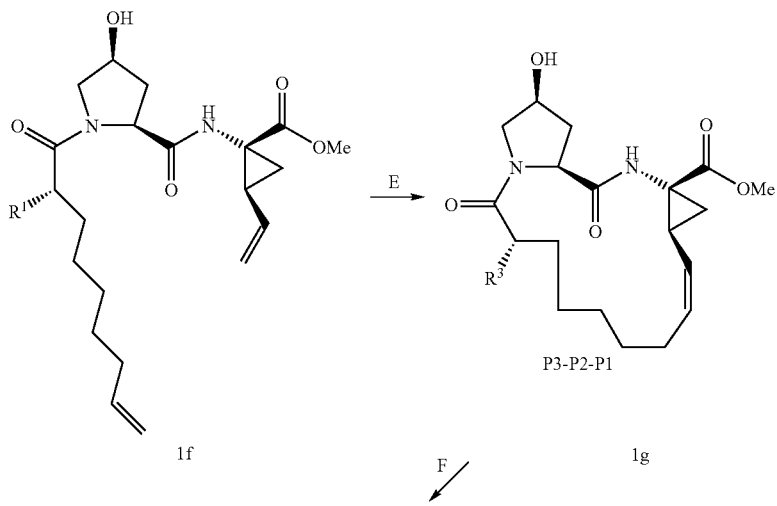

1f     E →     1g (P3-P2-P1)

F ↓

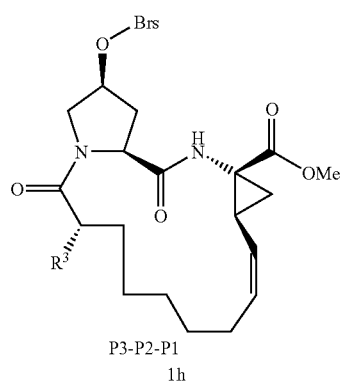

1h (P3-P2-P1)

Scheme I:

Steps A, C, D: Briefly, the P1, P2, and P3 moieties can be linked by well known peptide coupling techniques generally disclosed in WO 00/09543 & WO 00/09558.

Step B: This step involves the inversion of configuration of the 4-hydroxy substituent. There are several ways in which this can be accomplished as will be recognized by persons skilled in the art. One example of a convenient method is the well known Mitsunobu reaction (Mitsunobu *Synthesis* 1981, January, 1-28; Rano et al. *Tet. Lett.* 1994, 36, 3779-3792; Krchnak et al. *Tet. Lett.* 1995, 36, 6193-6196).

Step E: The formation of the macrocycle can be carried out via an olefin metathesis using a Ru-based catalyst such as the one reported by Miller, S. J.; Blackwell, H. E.; Grubbs, R. H. *J. Am. Chem. Soc.* 1996, 118, 9606-9614 (a); Kingsbury, J. S.; Harrity, J. P. A.; Bonitatebus, P. J.; Hoveyda, A. H. *J. Am. Chem. Soc.* 1999, 121, 791-799 (b) and Huang, J.; Stevens, E. D.; Nolan, S. P.; Petersen, J. L.; *J. Am. Chem. Soc.* 1999, 121, 2674-2678 (c) or as described in WO 00/59929. It will also be recognized that catalysts containing other transition metals such as Mo can be used for this reaction.

(a)

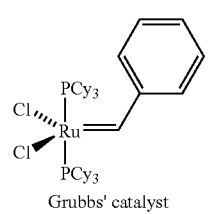

Grubbs' catalyst (b)

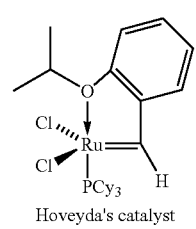

Hoveyda's catalyst

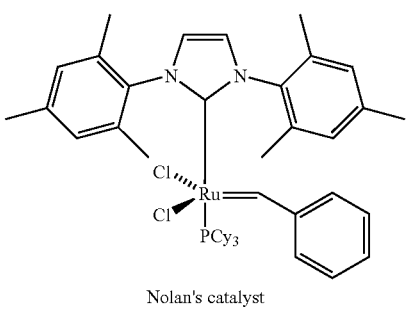

Nolan's catalyst

Step F: Conversion of the hydroxyl group of the proline to a suitable leaving group (i.e. brosylate) was carried out by reacting the free OH with the corresponding halo-derivative (i.e. 4-bromobenzenesulfonyl chloride).

Subsequent conversion of the key intermediate of formula 1 h to the compounds of formula (I) of this invention is disclosed in detail in the examples hereinafter.

IV. Introduction of the $R^2$ Moiety to Form Compounds of General Formula (Ic):

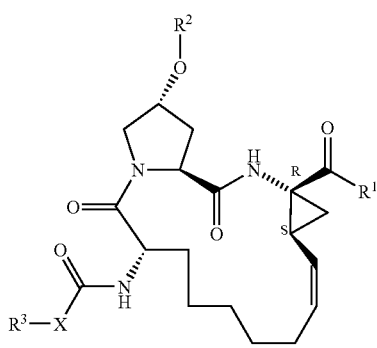

(Ic)

The general process comprises reacting a macrocyclic compound of formula (IXa or 1 h) with a compound of formula (X):

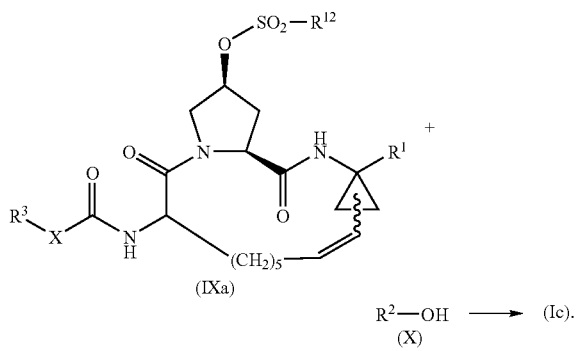

(IXa)

$R^2$—OH ⟶ (Ic).
(X)

Compounds of formula (IXa) and (X) are mixed in a polar non-protic organic solvent (such as THF, dioxane, dichloromethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of reaction. Aqueous workup followed by crystallization from a suitable solvent such as ethyl acetate-heptane or ethyl acetate/methylcyclohexane provides the compounds of formula (Ic).

VI. Synthesis of P2 Substituents:

The compounds of formula (X) used as starting material may be synthesized from commercially available materials using the techniques described in the literature.

General Protocol for the Preparation of 2-alkoxy Substituted 4-hydroxyquinolines (2a):

Compounds of formula X wherein $R^2$ is a group of formula

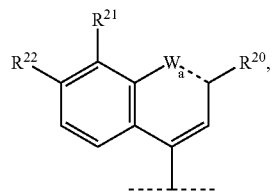

where $R^{20}$ is an alkoxy group, can be prepared according to the following scheme 2:

SCHEME 2

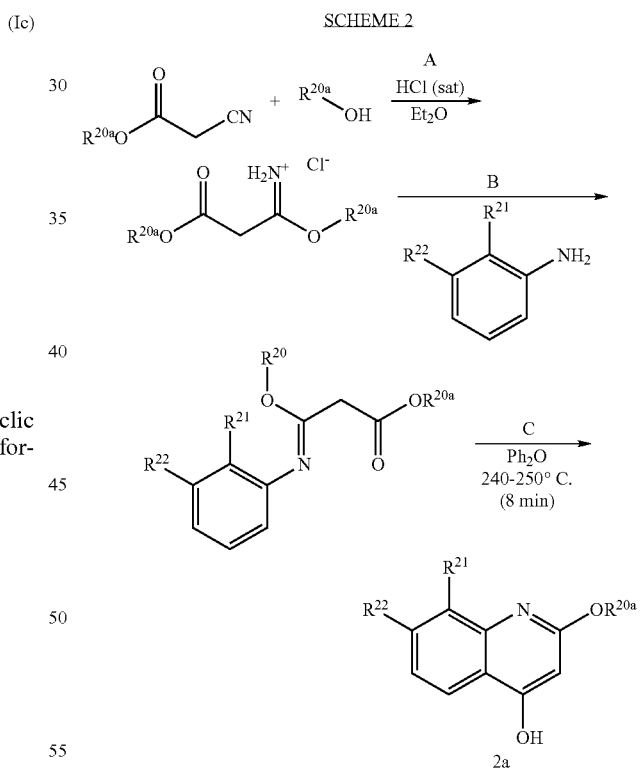

2a

Briefly, following the known Pinner synthesis, a suitably functionalized cyanoester is condensed with the corresponding alcohol using a fully saturated $HCl/Et_2O$ solution [Neilson, in Patai, "The Chemistry of Amidines and Imidates." pp. 385-489, Wiley, NY, 1975.]. The resulting imidate salt is then subsequently condensed with an appropriately substituted aniline to form the aniline derived imidate. Thermal cyclization affords the corresponding 2-alkoxy substituted 4-hydroxyquinolines 2a. For example, when $R^{20a}$=Et in the above scheme, ethyl cyanoacetate and ethanol are used as reagents.

For $R^{20a}$=Me in the above scheme, methyl cyanoacetate and methanol are used as reagents.

Compounds of formula X wherein $R^2$ is a group of formula

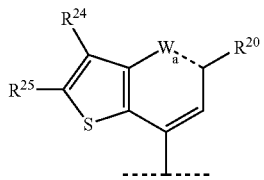

and $R^{20}$ is an alkoxy group can also be prepared according to scheme 2, by using an appropriately substituted aminothiophene in place of the aniline in step B above.

General Protocol for the Preparation of 2-alkyl Substituted 4-hydroxyquinolines (2b):

Compounds of formula X wherein $R^2$ is a group of formula

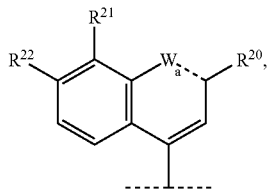

where $R^{20}$ is an alkyl group, can be prepared according to the following scheme 3:

SCHEME 3

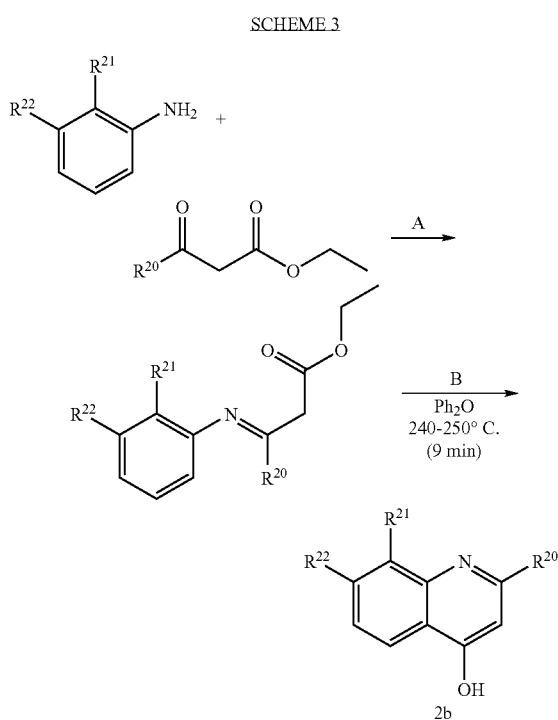

Briefly, appropriately substituted β-ketoesters are condensed with substituted anilines and subsequently thermally cyclized to afford the corresponding 2-alkyl substituted hydroxyquinolines. For example, when the initial condensation reaction with the aniline (step A) is performed with the corresponding methyl ketone ($R^{20}$=$CH_3$), a methyl group is incorporated in the 2-position of the resulting 4-hydroxyquinoline.

General Protocol for the Preparation of 2-thioalkyl Substituted 4-hydroxyquinolines (2c):

In general, the various 2-thioalkyl analogs were prepared as shown in the following scheme 4.

SCHEME 4

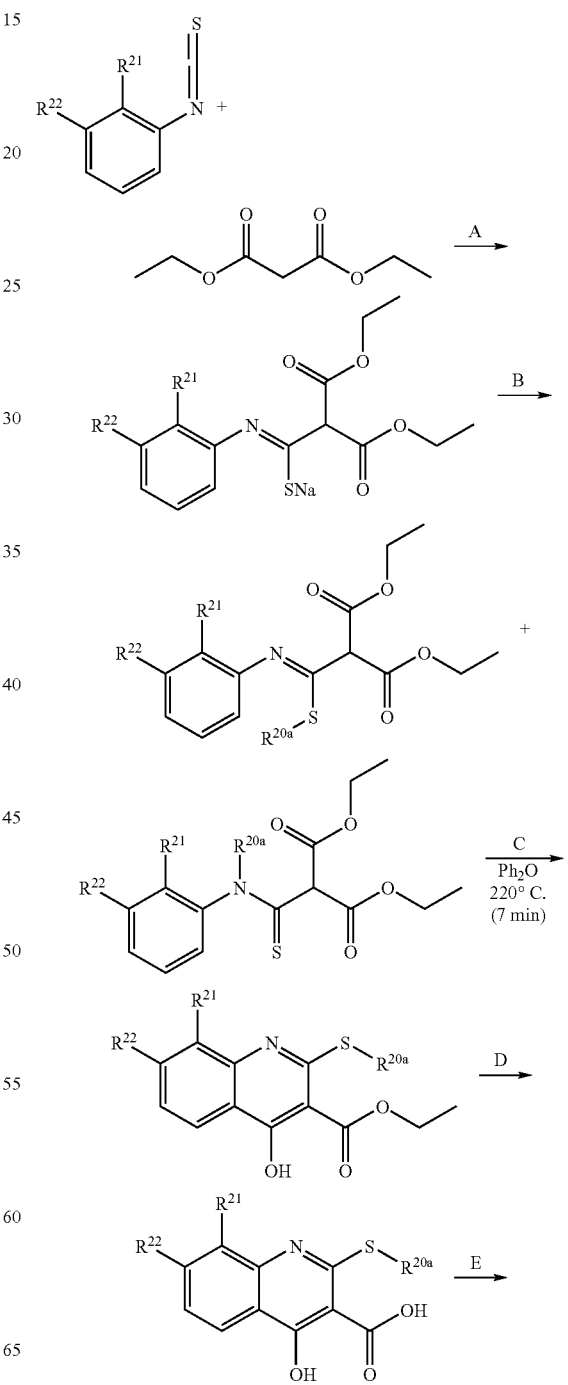

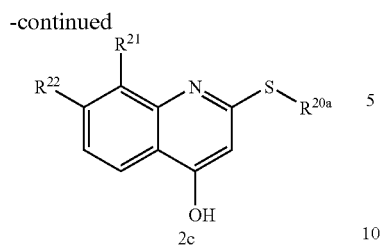

2c

Briefly, condensation of diethyl malonate under basic conditions with a suitably functionalized isothiocyanate produces the malonate adduct as a salt. Treatment of the salt with an alkylating reagent (e.g. EtI: ethyl iodide) produces a mixture of S- and N-alkylated products. Thermal cyclization of this mixture gives the 3-ethyl carboxylate which is saponified and decarboxylated to produce the desired 2-thioalkyl substituted hydroxyquinolines. For example, utilization of EtI in the alkylation step results in the formation of the 2-thioethyl analog ($R^{20a}$=Et).

Alternative Protocol for the Preparation of 2-alkoxy and 2-alkynyl Substituted 4-hydroxyquinolines (2d):

Compounds of formula X wherein $R^2$ is a group of formula

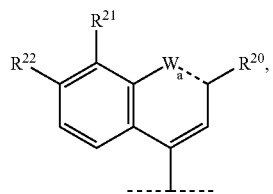

wherein $R^{20}$ is a substituted or unsubstituted alkoxy group or an alkynyl group may be prepared according to the following Scheme 5:

SCHEME 5

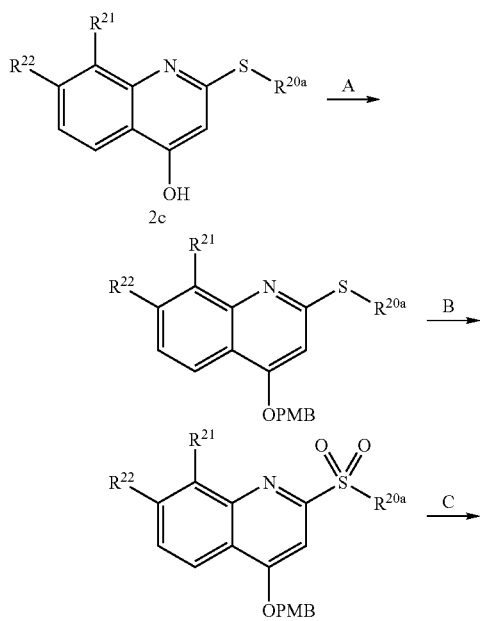

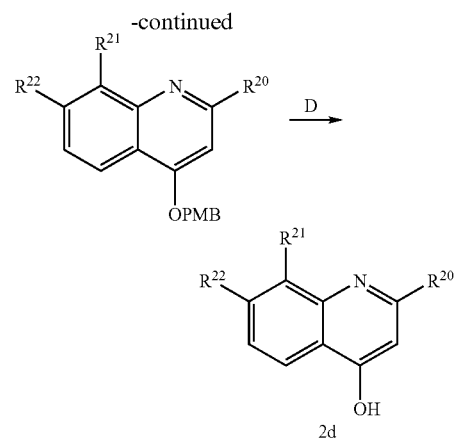

2d

Briefly, a compound of formula 2c (Scheme 4), wherein $R^{20a}$ is a small alkyl group such as ethyl or propyl, is protected at the hydroxy group as, for example, a p-methoxybenzyl (PMB) ether. The protected quinoline is oxidized, using reagents well known in the art, to give a sulfone which is then treated with a suitable nucleophile to introduce the $R^{20}$ group. Examples of suitable nucleophiles include, but are not limited to, appropriately substituted and/or protected alkoxide anions and acetylide anions. Deprotection of the PMB ether, and of the $R^{20}$ substituent if necessary, then gives the desired 4-hydroxyquinoline compounds 2d.

The corresponding anilines are commercially available or may require some well known chemical transformations. For example if the nitro analog is commercially available, it can be converted to the corresponding amine by using any of several reducing agents well known to one skilled in the art. Also, if the carboxylic acid is commercially available, transformation into the corresponding amine is possible via a Curtius rearrangement.

Further details of the invention are illustrated in the following examples which are understood to be non-limiting with respect to the appended claims. Other specific ways of synthesis or resolution of the compounds of this invention can be found in WO 99/07733, WO 00/09543; WO 00/09558 & WO 00/59929 and in co-pending application Ser. No. 10/945,518, all of which are hereby incorporated by reference.

EXAMPLES

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million and are referenced to the internal deuterated solvent unless otherwise indicated. The NMR spectra of all final compounds (inhibitors) was recorded in DMSO-$d_6$. Flash column chromatography was carried out on silica gel ($SiO_2$) according to Still's flash chromatography technique (W. C. Still et al., *J. Org. Chem.*, 1978, 43, 2923). Analytical HPLC was carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations used in the examples include Boc: tert-butyloxycarbonyl [Me$_3$COC(O)]; BSA: bovine serum albumin; Brs: brosyl (p-bromobenzenesulfonyl); CDI: N,N'-carbonyldiimidazole; CHAPS: 3-[(3-cholamidopropyl)-dimethylammonio]-1-propanesulfonate; DABCO: 1,4-diazabicyclo[2.2.2]octane; DBU: 1,8-diazabicyclo[5.4.0]undec-7-ene; DCM: dichloromethane (CH$_2$Cl$_2$; methylene chloride); DCE: dichloroethane; DCHA: dicyclohexylamine; DEAD: diethylazodicarboxylate; DIAD: diisopropylazodicarboxylate; DIPEA: diisopropylethylamine; DMAP: dimethylaminopyridine; DMF: N,N-dimethylformamide; DMSO: dimethylsulfoxide; EDCl: 1-ethyl-3-[3-(dimethylamino)propyl]-carbodiimide hydrochloride; (S,S)-Et-DUPHOS Rh (COD) OTf: (+)-1,2-bis (2S,5S)-2,5-diethylphospholano) benzene (cyctooctadiene) rhodinium (1) trifluoromethanesulfonate; Et: ethyl; EtOH: ethanol; EtOAc: ethyl acetate; ESMS: electrospray mass spectrometry; FAB: Fast Atom Bombardment; HATU: O-(7-azabenzotriazol-1-yl)-1,1,3,3-tetramethyluronium hexafluorophosphate; HPLC: high performance liquid chromatography; MS: mass spectrometry; MALDI-TOF: Matrix Assisted Laser Disorption Ionization-Time of Flight; MCH: methylcyclohexane; Me: methyl; MeOH: methanol; MIBK: methyl isobutyl ketone; NMP: N-methylpyrrolidinone; PMB: para-methoxy benzyl; Pr: propyl; R.T.: room temperature (18° C.-22° C.); TBTU: 2-(1H-benzotriazole-1-yl)-1,1,3,3-tetramethyluronium tetrafluoroborate; TFA: trifluoroacetic acid; THF: tetrahydrofuran; THP: tetrakishydroxymethyl phosphonium chloride; TLC: thin layer chromatography; Tris/HCl: tris(hydroxymethyl)aminomethane hydrochloride; SEH: sodium 2-ethylhexanoate; PTSA: para-toluenesulfonic acid.

Example 1

Synthesis of INRF12 Brosylate Intermediate

Step 1: Introduction of the Boc-protecting Group: Synthesis of INRF2

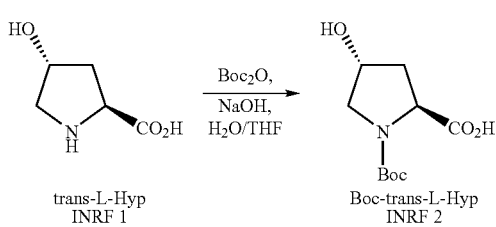

The amino-protection was done with the Boc-protecting-group. INRF 1 (trans-4-hydroxy L-proline) (249.8 g, 1.905 mol) was dissolved in water (375 mL) and 45% sodium hydroxide solution (203 g, 2.286 mol). To ensure good phase transfer, tert-butanol (106 g) was added. In an alternative procedure, acetone was used instead of THF/tert-butanol. The reaction mixture was heated to 50° C. and the anhydride Boc$_2$O (424 g, 1.943 mol), dissolved in THF (425 mL), or acetone, was slowly added. The reaction is exothermic and generates gas (CO$_2$) as the Boc$_2$O was added. If the reaction does not proceed as desired, catalytic amounts of DMAP (2.3 g, 19 mmol) can be added. After the addition of the Boc$_2$O, the reaction mixture was kept 0.5-1 h at 50° C., and the THF was removed by partial distillation. The pH of the remaining solution was adjusted to about pH 3 with concentrated HCl (204 g, 2.076 mol) and the product was then extracted with MIBK (1 liter) and again with MIBK (375 mL). The organic layer was heated and some of the solvent was distilled off to remove traces of water. The product was crystallized from this solution by adding MCH (1.25 L), isolated by filtration, washed twice with MCH (375 mL) and dried overnight at 40° C.

Yield: 77-78%, colorless crystals, $F_p$=126-128° C.

Step 2: Formation of the Lactone: Synthesis of PDIG0016

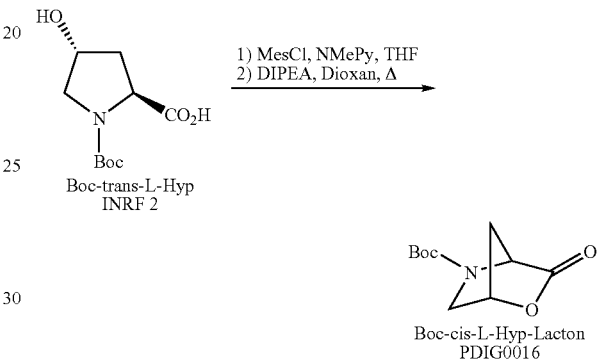

INRF 2 (416.3 g, 1.8 mol) is dissolved in THF (2.08 L) and cooled with ice to a temperature from about −5 to −10° C. Mesylchloride (392 g, 3.4 mol) and N-methylpyrrolidine (429 g, 5 mol) is added and the mixture stirred for about 1½ h at about −5° C. The mixture is washed with water and heated to reflux. Dioxane (2.08 L) is added and the THF is distilled off. After cooling down to room temperature, DIPEA (233 g, 1.8 mol) is added and the mixture is heated to reflux. After 1 h, part of the solvent (830 mL) is distilled off. The remaining solution is cooled to ambient temperature, a KHSO$_4$-solution (14.4 g in 2.08 l water) is added and the solution is allowed to cool down to room temperature. The resulting crystals (PDIG0016) are isolated by filtration, washed with water and dried overnight at 45° C.

Yield: 78-82%, colorless needles, $F_p$=111° C.

Step 3: Deprotection of the Lactone: Synthesis of PDIG0017MS

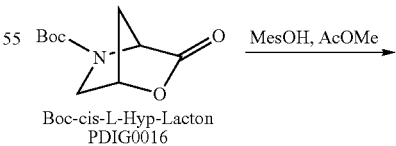

The lactone PDIG0016 (267 g, 1.25 mol) is dissolved in methyl-isobutylketone (1467 mL). The suspension is heated up to 50° C. until the lactone is completely dissolved and a part of the solvent (130 mL) is distilled off to remove traces of water. Methanesulfonic acid (240 g, 2.5 mol) is added slowly to the reaction mixture. During the addition, gas is evolved (CO$_2$, isobutene). The reaction mixture is allowed to cool to room temperature and the resulting crystals are isolated by filtration, washed twice with acetone (each 400 mL) and dried overnight at 40° C.

Yield: 93-98%, colorless crystals, 208-210C.

Step 4: Coupling with INRF 15; Synthesis of the Dipeptide PDIG0027

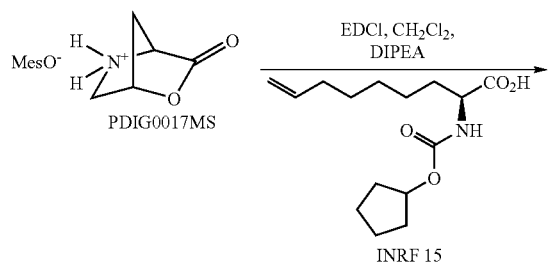

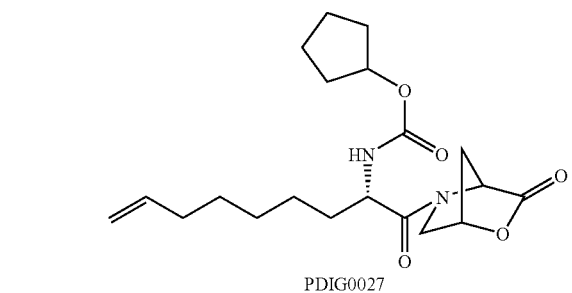

First, INRF15.DCHA has to be released. Therefore, INRF15.DCHA (61.4 g, 132 mmol) is dissolved in toluene (160 mL) and the resulting solution is washed with diluted sulfuric acid (5.3 g in 80 mL water) and water (80 mL). After phase separation, the solution is treated with charcoal and filtered and the resulting solution stored at room temperature.

The deprotected lactone PDIG0017MS (24.9 g, 119 mmol) and EDCl.HCl (26.8 g, 140 mmol) are suspended in dichloromethane (140 mL) and cooled to room temperature. The suspension is treated with the INRF15-solution previously generated. To this suspension, di-isopropylethylamine (Hünigs-Base, 16.3 g, 130 mmol) is slowly added while the reaction is kept under nitrogen at temperatures below 20° C. The suspension is filtered, and the resulting solution is washed with water (80 mL), diluted acetic acid (1.3 g in 80 mL water), 5% sodium bicarbonate solution (80 mL) and again with water (80 mL). After phase separation, dichloromethane is distilled off under reduced pressure. The resulting solution can directly be used for the next step. Otherwise, the product can be isolated by crystallization from MCH.

Yield: 95% (GC), yellowish solution, F$_p$=58-60° C.

Step 5: Synthesis of INRF 16-OH

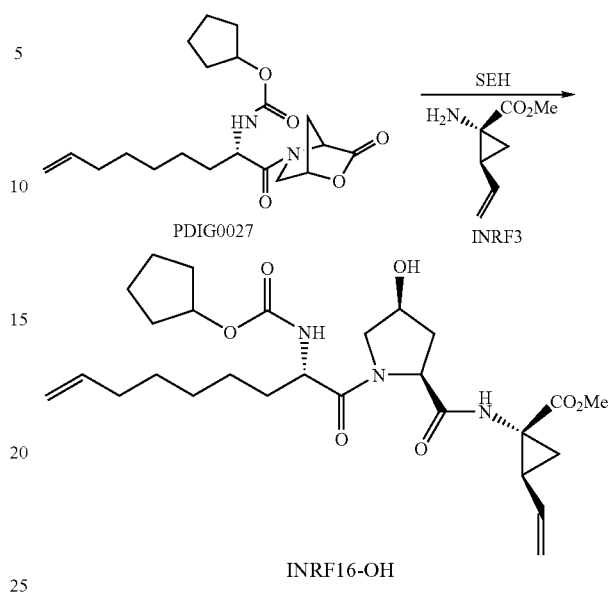

A mixture of PDIG0027 (10.0 g, 23.7 mmol, 1.0 eq.), INRF3 (7.6 g, 24.2 mmol, 1.02 eq.) and sodium 2-ethylhexanoate (SEH) (5.9 g, 35.6 mmol, 1.5 eq.) in water (43 mL) and toluene (12 mL) is stirred at 80° C. for 2 h. For work-up, toluene (75 mL) is added at 80° C. After stirring and separation of the aqueous layer, the organic layer is washed with 1M Na$_2$CO$_3$ (3×30 mL), 0.5M HCl (30 mL) and water (2×30 mL). The solvent is removed under vacuum.

Yield of INRF16-OH: 11.7 g, 22.5 mmol, 95%; purity: >95% (peak-area HPLC) as a slightly yellow oil.

Step 6. Brosylation of INRF16-OH: Synthesis of INRF16-Brs

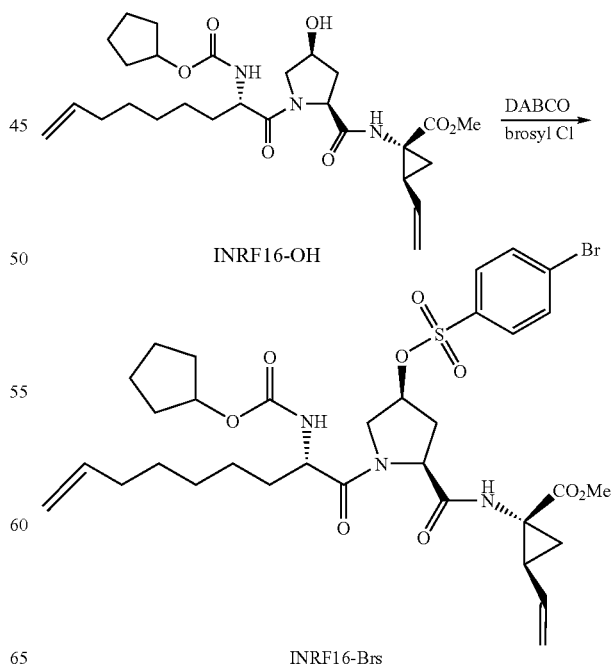

To a mixture of INRF16-OH (10.7 g, 18.5 mmol, 1.0 eq.) and DABCO (3.3 g, 29.7 mmol, 1.6 eq.) and toluene (23 mL) a solution of 4-bromobenzenesulfonyl chloride (brosyl chloride, 6.6 g, 26.0 mmol, 1.4 eq.) in toluene (15 mL) is added slowly at room temperature. The mixture is stirred for 2 h. For work-up the organic layer is washed with 1M $Na_2CO_3$ (2×21 mL), diluted with THF (21 mL) and washed with 0.5M HCl (21 mL) and water (2×21 mL). The solvent is removed under vacuum. Yield of INRF16-Brs: 12.3 g, 16.7 mmol, 90%; purity: >95% (peak-area HPLC) as a slightly orange oil. A charcoal treatment of the crude product is possible.

Step 7: Metathesis of INRF16Brs to INRF12Brs

INRF16Brs are dissolved in 70 mL of degassed toluene and added into the reaction flask. The solution is heated up to 80° C. and 3 mol % of Hoveyda's catalyst is added under nitrogen in four portions over a period of 3 hours. After stirring for a further 60 min at the same temperature the conversion is checked by HPLC. In the case that the conversion is below 95%, additional Hoveyda's catalyst is added and the mixture is stirred until the conversion is >95% (during the reaction a slight stream of nitrogen is bubbled through the reaction mixture).

After cooling to 50° C. the THP solution is added to the reaction mixture. After stirring for 8.5 h at 50° C. the mixture

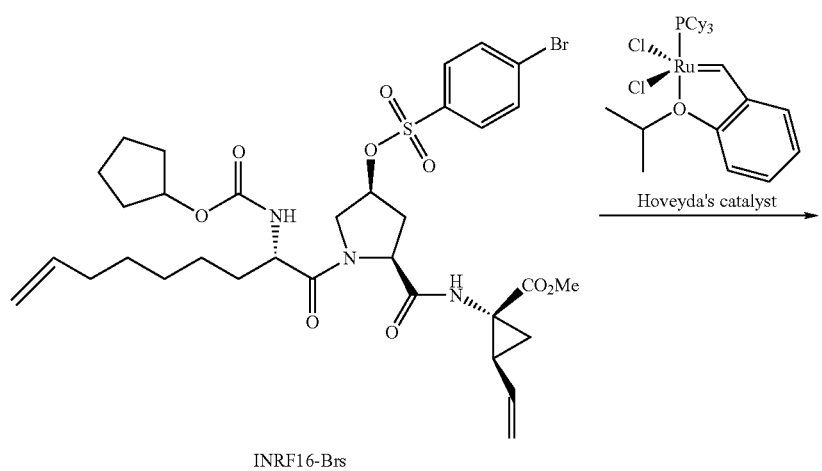

INRF16-Brs

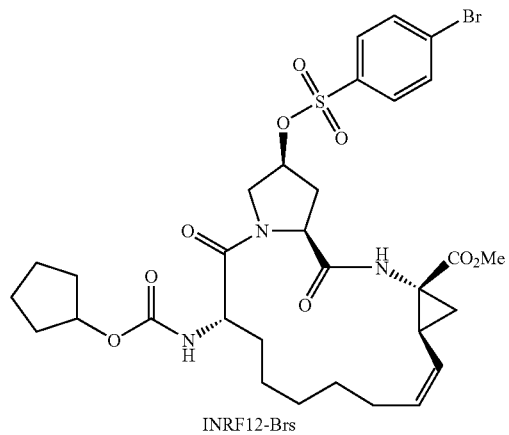

INRF12-Brs

Preparation of the THP-solution (for an experiment with 35.4 g INRF16Brs): 23.5 g of tetrakis(hydroxymethyl)phosphonium chloride (80% in water, 98.7 mmol) is dissolved in isopropanol (35 mL) under a nitrogen atmosphere. Then 12.1 g (98.7 mmol) of a 45% KOH solution is added within 5 min while the solution is cooled (temperature 20-25° C.). After stirring the suspension for another 30 min under nitrogen, the mixture is filtered and the inorganic residue is washed with 20 mL of degassed isopropanol. The combined isopropanol solution is stored under a nitrogen atmosphere until use.

Metathesis Reaction:

In a reaction flask 3500 mL of toluene is degassed by bubbling nitrogen through the toluene. 35.2 g (47.7 mmol) of is cooled to room temperature and extracted twice with 188 mL of degassed water, 188 mL of 0.5 M HCl, 188 mL of 0.5 M $NaHCO_3$ solution, and 188 mL of water.

Approximately 2800 mL of toluene are distilled off at 50° C. under partial reduced pressure and the remaining solution is treated at 50° C. with 6.8 g of activated charcoal which is then removed by filtration.

The remaining liquid filtrate (approx. 130 mL) is added over a period of 1 hour to 1.5 liters of pre-cooled MCH (5° C.). After stirring for a further 30 min at 5C the precipitate is filtered and washed with 100 mL of MCH (several portions). The white solid is dried in vacuo at 25° C.

Yield (by weight): 38 g of an almost white powder.

Example 1A

Synthesis of Brosylate Intermediate with a Saturated Linker for the Syntheis of Compounds of Table 2

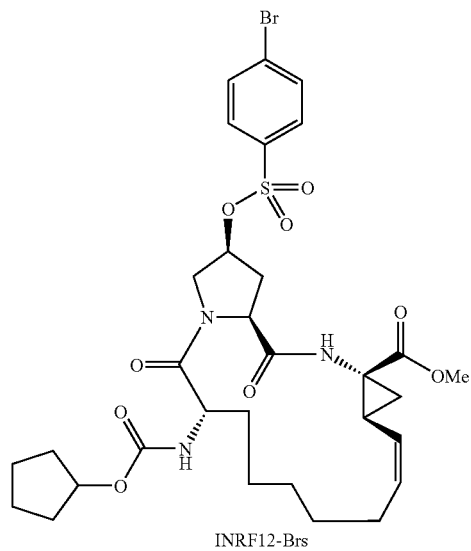

Example 2A

Synthesis of 1-methyl-2-methoxy Aniline (2A2)+

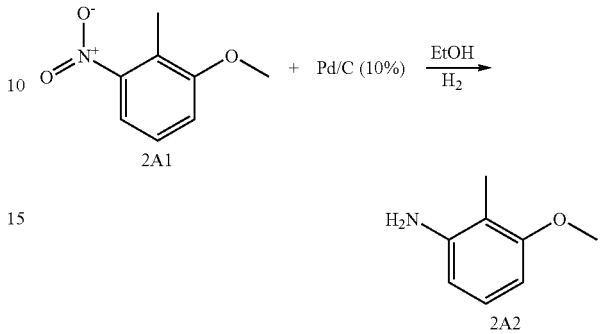

To a solution of 2-methyl-3-nitro anisole (2A1) (5.1 g; 30.33 mmol; requires ~30 min. to dissolve) in absolute ethanol (85 mL) was added 10% Pd/C catalyst (500 mg). The solution was hydrogenated under a hydrogen filled balloon at atmospheric pressure and room temperature for 19 h. The reaction mixture was filtered through a Celite pad, rinsed and evaporated to dryness to obtain the compound 2A2 as a deep mauve oil (4.1g; 29.81 mmol; 98% yield).

MS 137 (MH)+. Reverse Phase HPLC Homogeneity @ 220 nm (0.06% TFA; $CH_3CN:H_2O$): 99%.

Example 2B

Synthesis of 2-bromo-3-methoxy aniline (2B4)

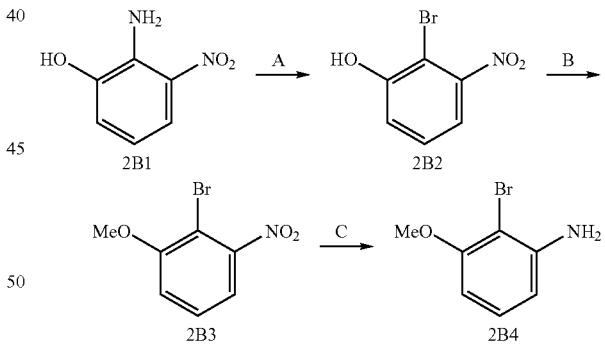

Step A: To brosylate INRF12-Brs (1.0 g, 1.41 mmol, 1 eq.) dissolved in EtOAc (30 mL) was added 5% Rh/Al (300 mg, 30% w/w). The atmosphere was saturated with $H_2$ gas and stirred at RT for 10 h until complete conversion by HPLC analysis. The suspension was filtered through Celite to remove the catalyst and the solvent removed in vacuo to afford a white solid. Purification ($SiO_2$, (1:1) EtOAc/hexanes) afforded after concentration the saturated macrocycle 1A1 (467 mg, 47%) as a white solid.

Step A:

2-Amino-3-nitrophenol 2B1 (5 g; 32.4 mmol) was dissolved in $H_2O$ (29.5 mL) and 1,4-dioxane (14.7 mL). The mixture was heated to reflux and hydrobromic acid (48%; 16.7 mL; 147 mmol) was added dropwise over a period of 20 min. Upon completion of the addition, the reflux was maintained an additional 15 min. The reaction was cooled to 0° C. (ice bath), and sodium nitrite (2.23 g; 32.3 mmol) in $H_2O$ (20 mL) was added over a period of 30 min. The stirring was continued for 15 min. at 0° C., the mixture transferred to a jacketed dropping funnel (0° C.) and added dropwise to a stirred mixture of Cu(I)Br (5.34 g; 37.2 mmol) in $H_2O$ (29.5 mL) and HBr (48%; 16.7 mL; 147 mmol) at 0° C. The reaction was stirred for 15 min. at 0° C., warmed to 60° C., stirred for an additional 15 min., cooled to room temperature, and left to stir overnight. The reaction mixture was transferred to a separatory funnel and extracted with ether (3×150 mL). The organic layers were combined, washed with brine (1×), dried ($Na_2SO_4$), filtered and concentrated to afford the crude product (7.99 g) as a red-brown oil. The crude material was purified by flash column chromatography (1:25 ultra pure silica gel, 230-400 mesh, 40-60 mm, 60 angstroms; $CH_2Cl_2$ as the solvent) to afford pure 2-bromo-3-nitro-phenol 2B2 (45%; 3.16 g) as an orange-brown solid.

MS 217.8 $(MH)^-$. Homogeneity by HPLC (TFA) @ 220 nm: 97%.

Step B:

The nitrophenol starting material 2B2 (3.1 g; 14.2 mmol) was dissolved in DMF (20 mL) and to the solution was added ground cesium carbonate (5.58 g; 17.1 mmol) followed by MeI (2.6 mL; 42.5 mmol). The mixture was stirred at room temperature overnight. The DMF was evaporated, the residue taken up in ether (1×200 mL), washed with water (1×200 mL), brine (4×100 mL), dried ($MgSO_4$), filtered and evaporated to afford the crude 2-bromo-3-nitroanisole 2B3 (94%; 3.1 g) as an orange solid.

MS 234 $(M+2H)^+$; Homogeneity by HPLC (TFA) @ 220 nm: 98%

Step C:

2-Bromo-3-nitroanisole 2B3 (1.00 g; 4.31 mmol) was dissolved in glacial acetic acid (11.0 mL)/ethanol (11.0 mL) and to the solution was added iron powder (0.98 g; 17.5 mmol). The mixture was stirred at reflux for 3.5 h and worked up. The reaction mixture was diluted with water (35 mL), neutralized with solid $Na_2CO_3$ and the product extracted with $CH_2Cl_2$ (3×50 mL). The extracts were dried ($Na_2SO_4$), filtered and concentrated in vacuo to afford the crude product, 2-bromo-3 methoxyaniline 2B4 (91%; 0.79 g) as a pale yellow oil.

MS 201.8 $(MH)^+$; Homogeneity by HPLC (TFA) @ 220 nm: 95%

Example 2C

Synthesis of 2-chloro-3-methoxy aniline (2C3)

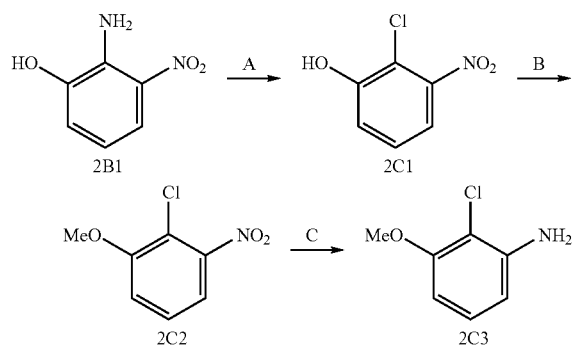

Step A:

2-Amino-3-nitrophenol 2B1 (5 g; 32.4 mmol) was dissolved in concentrated HCl (75 mL) and 1,4-dioxane (14.7 mL). The mixture was heated to 70C until most of the solids were in solution. The reaction mixture was cooled to 0° C. (ice bath), and sodium nitrite (2.23 g; 32.3 mmol) in $H_2O$ (5.4 mL) was added over a period of 3 hours to the brown solution. The temperature was maintained below 10C during the addition and the stirring was continued for an additional 15 min. at 0° C. This diazonium intermediate was poured into a solution of Cu(I)Cl (3.8 g; 38.9 mmol) in $H_2O$ (18.5 mL) and conc. HCl (18.5 mL) at 0° C. The reaction was stirred for 15 min. at 0° C., warmed to 60° C., and stirred for an additional 15 min. The reaction mixture was then brought to room temperature, and left to stir overnight. The reaction mixture was transferred to a separatory funnel and extracted with ether (3×150 mL). The organic layers were combined, washed with brine (1×), dried ($Na_2SO_4$), filtered and concentrated to afford the crude product (5.83 g) as a red-brown oil. The crude material was purified by flash column chromatography (1:25 ultra pure silica gel, 230-400 mesh, 40-60 mm, 60 angstroms; 3:1 hexane/EtOAc as the solvent) to afford pure 2-chloro-3-nitrophenol 2C1 (48%; 2.7 g) as an orange solid. MS 171.8 $(MH)^-$: Homogeneity by HPLC (TFA) @ 220 nm: 96%.

Relevant literature for the Sandmeyer Reaction: *J. Med. Chem*, 1982, 25(4), 446-451.

Step B:

The nitrophenol starting material 2C1 (1.3 g; 7.49 mmol) was dissolved in DMF (10 mL) and to this solution was added ground cesium carbonate (2.92 g; 8.96 mmol), followed by MeI (1.4 mL; 22.5 mmol). The mixture was stirred at room temperature overnight. The DMF was evaporated in vacuo and the residue taken up in ether (150 mL), washed with water (150 mL), brine (4×100 mL), and then dried over ($MgSO_4$). The organic phase was filtered and evaporated to afford the crude 2-chloro-3-nitroanisole 2C2 (98%; 1.38 g) as an orange solid.

Homogeneity by HPLC (TFA) @ 220 nm: 93%.

Step C:

2-Chloro-3-nitroanisole 2C2 (1.38 g; 7.36 mmol) was dissolved in a mixture of glacial acetic acid (19 mL)/ethanol (19 mL). To this solution was added iron powder (1.64 g; 29.4 mmol). The mixture was stirred at reflux for 3.5 h and worked up. The reaction mixture was diluted with water (70 mL), neutralized with solid $Na_2CO_3$ and the product extracted with $CH_2Cl_2$ (3×150 mL). The extracts were combined and washed with sat. brine and then dried over ($Na_2SO_4$), filtered and concentrated in vacuo to afford the crude product, 2-chloro-3-methoxyaniline 2C3 (100%; 1.2 g) as a yellow oil. This material was used as such in the following steps.

MS 157.9 $(MH)^+$; Homogeneity by HPLC (TFA) @ 220 nm: 86%.

Example 3A

Preparation of 2-ethoxy-4-hydroxy-8chloroquinoline (3A5)

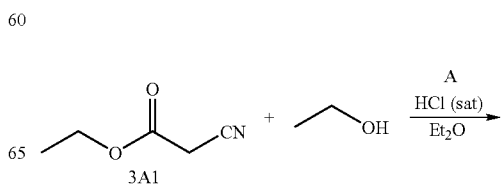

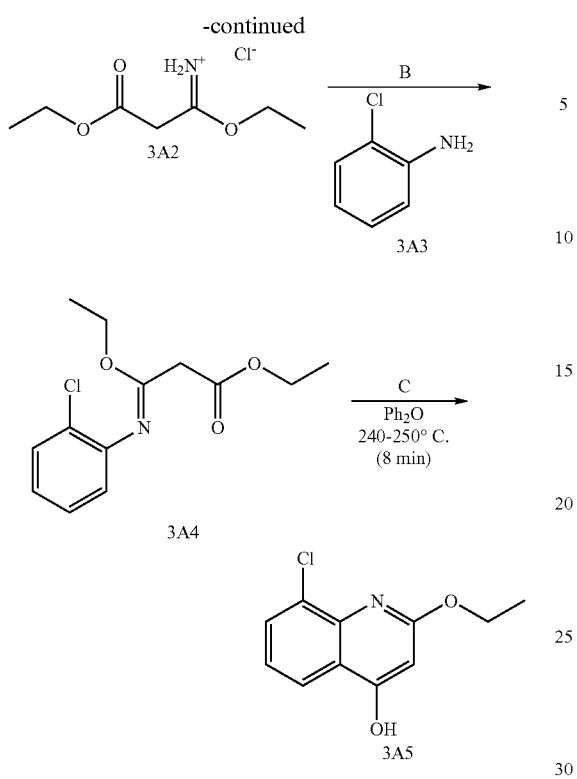

Step A: To ethyl cyanoacetate 3A1 (23 g, 0.203 mol) was added absolute ethanol (10 g, 12.7 mL, 0.22 mol) in diethyl ether (20 mL). The solution was cooled to 0° C. in an ice bath before being treated with HCl gas (bubbled through solution for 12 minutes resulted in an increase in weight of 12 g (~0.33 mol)).

This solution was stirred at 0° C. for 6 h and then was allowed to warm to R.T. and was stirred for 16 h. The resultant solid was broken up and washed several times with ether and then placed in vacuo for several hours. The imidate salt 3A2 was obtained as a white solid (36.4 g, 92%) and was stored under a nitrogen atmosphere. The $^1$H NMR is consistent with the desired product.

Step B: The imidate salt 3A2 (1.47g, 7.5 mmol, 1 eq.) was combined with 2-chloroaniline 3A3 (0.96g, 7.50 mmol, 1 eq.) in ethanol (15 mL) under an $N_2$ atmosphere. The reaction mixture was stirred at R.T. (16 h) and monitored by HPLC. The reaction mixture was concentrated and then purified directly over silica gel (eluent: 10% EtOAc/hexanes) to afford the condensation product 3A4 as a clear oil (1.73 g, 86%). MS electrospray: (MH)+; 270 and (M−H)−; 268. TLC (UV) Rf=0.50 (10% EtOAc/hexane).

Step C: The condensation product 3A4 (1.73g, 6.41 mmol) was dissolved in diphenyl ether (10 mL) and placed in a sand bath (300° C.). The internal temperature was monitored and maintained between 240-250° C. for 8 minutes. The mixture was cooled and then directly loaded on a silica gel column and eluted first with hexanes, then with 30% EtOAc/hexanes and finally 50% EtOAc/hexanes. The product was concentrated and dried in vacuo to give the corresponding 4-hydroxyquinoline derivative 3A5 as a beige crystalline solid (0.76 g, 53%). MS electrospray: (M+H)$^+$; 224 and (M−H)$^-$; 222.

Example 3B

Preparation of 4-hydroxy-8-chloroquinoline (3B3)

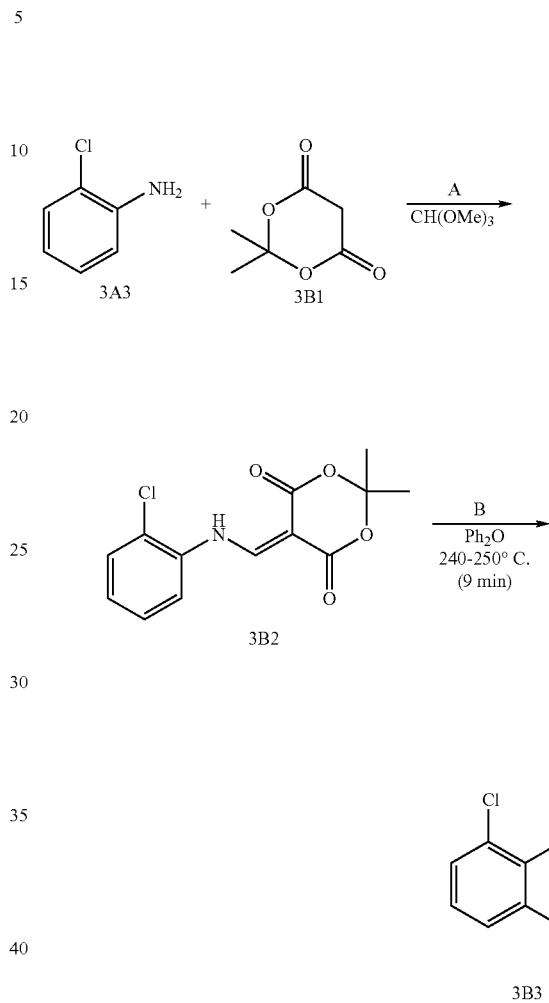

Step A: To 2-chloroaniline 3A3 (1.6 mL, 15.2 mmol, 1 eq) dissolved in anhydrous acetonitrile (50 mL) at R.T. was added Meldrum's acid 3B1 (2.41 g, 16.73 mmol, 1.1 eq), followed by trimethyl orthoformate (2.0 mL, 18.25 mmol, 1.2 eq). The resulting mixture was heated to reflux (95° C.) for 2 h and monitored by analytical HPLC until complete. The resulting solution was cooled to R.T. and evaporated to dryness to afford a beige solid that was recrystallized from boiling MeOH. After drying in vacuo adduct 3B2 was obtained as a bright yellow solid (2.29 g, 53%).

Step B: In a pre-heated sand bath (300-350° C.), diphenyl ether (6 mL) was heated until the internal temperature reached 220° C. Adduct 3B2 (981 mg, 3.48 mmol) was added portionwise over ca. 4 min period (gas evolution) to the heated solvent. The temperature (220° C.) was maintained for another 5 min after which the solution was allowed to cool.

Upon cooling, the product precipitated out of solution and was filtered and washed with diethyl ether. After drying in vacuo (16 h), product 3B3 was obtained as a beige solid (417 mg, 67%). MS: (M+H)−; 180.

Example 3C

Preparation of 8-chloro-4-hydroxy-2-methylquinoline (3C3)

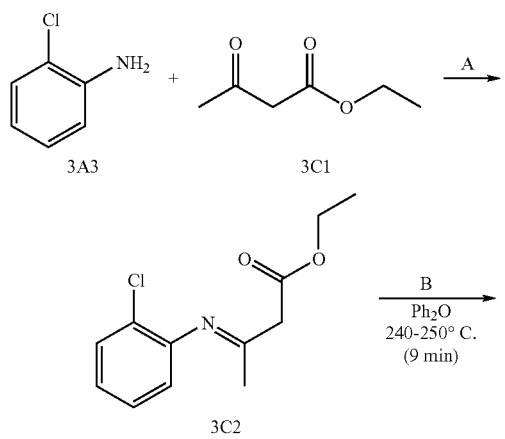

Step A: To a solution of ethyl acetoacetate 3C1 (1.21 mL, 9.51 mmol; 1 eq) in benzene (20 mL) was added 2-chloroaniline 3A3 (1.0 mL; 9.51 mmol; 1 eq) followed by catalytic PTSA (13 mg). The reaction flask was equipped with a Dean-Stark apparatus and heated to reflux for 2 hours. The solvent was removed and the residue purified by column chromatography using silica gel (eluent: 10% EtOAc/hexanes; $R_f$=0.48) to give compound 3C2 (1.46 g, 64%) as a clear oil. MS: (M+H)+; 240, HPLC homogeneity=99.5%.

Step B: In a pre-heated sand bath (300-350° C.), compound 3C2 (730 mg, 3.0 mmol) in diphenyl ether (8 mL) was heated until the internal temperature reached 220° C. and that temperature was maintained for 7 minutes after which the solution was allowed to cool. Upon cooling, a beige solid precipitated out and was filtered and washed with diethyl ether. After drying, the desired quinoline 3C3 was obtained as a beige solid (452 mg, 77%). MS: (M+H)+; 194, HPLC homogeneity=99%.

Example 3D

Preparation of 2-thioethyl-8chloro-4-hydroxyquinoline (3D7):

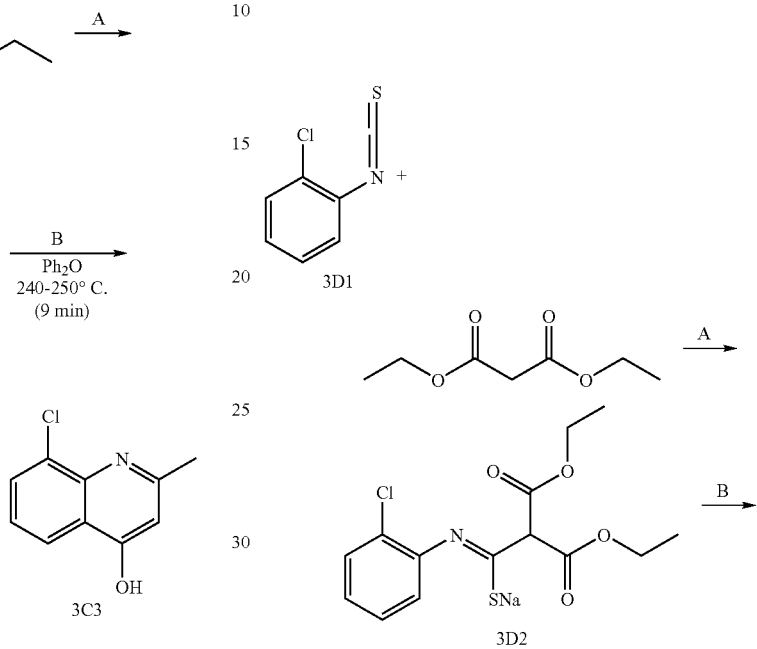

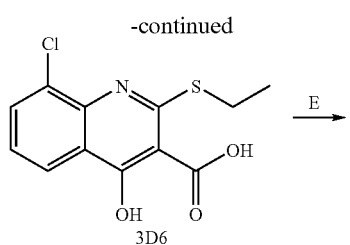

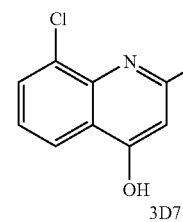

Step A: To THF (30 mL) was added sodium hydride (60% in oil, 920 mg, 23 mmol, 1.2 eq) before being cooled to 0° C. Diethyl malonate (2.91 mL, 19.15 mmol, 1.0 eq) was then added dropwise (gas evolution) and this solution was allowed to warm to R.T. and was stirred for 1 h. This mixture was cooled down to 0° C. before the addition of 2-chlorophenyl isothiocyanate 3D1 (2.5 mL, 19.15 mmol, 1.0eq). The resulting mixture was again allowed to warm to R.T. for 3 h until the SM was consumed. The orange solution was concentrated down and dried in vacuo to afford the sodium salt adduct 3D2 (6.73 g, 100%) as an orange crystalline solid. This material can be used as is for subsequent experiments.

Step B: A solution of adduct 3D2 (6.0 g, 17.06 mmol, 1 eq) in DMF (50 mL) was cooled down to −45° C. Ethyl iodide (1.64 mL, 20.5 mmol, 1.2 eq) was then slowly added and the solution was stirred at −45° C. for 2 h and then at R.T. (16 h). Water was added and the mixture was extracted twice with a mixture of ether/hexanes (1:1, 3×150 mL). The combined organic fractions were washed with water (2×), dried over $MgSO_4$, filtered and concentrated to afford approximately a 1:1 mixture of 3D3 and 3D4 (S versus N alkylation) (6.1g, 100%) as a yellow oil. This mixture is used in the following step since only the S-alkylated analog cyclizes.

Step C: In a pre-heated sand bath (350° C.) a solution of compounds 3D3 and 3D4 (6.1 g, 17.05 mmol, 1 eq.) in diphenyl ether (60 mL) was heated until the internal temperature reached 220° C., which was maintained for 7 minutes. The solution was cooled to R.T. and the mixture loaded directly on a silica gel column, being eluted first with hexanes (1 L) to remove the diphenyl ether, and then 3% EtOAc/hexanes to afford the desired quinoline 3D5 (2.76 g, 52%) as a pale yellow solid. The product was suitable for use in the next step.

Step D: To a solution of quinoline 3D5 (2.76 g crude; 8.85 mmol; 1 eq) in THF (10 mL) and methanol (10 mL) at R.T. was added 1N NaOH (45 mL; 45 mmol; 5.1 eq). The reaction was allowed to stir at reflux (85° C.) for 24 h (monitored by HPLC). The mixture was acidified with 4N HCl and extracted with methylene chloride (3×). The organic fractions were dried over $MgSO_4$, filtered and concentrated to afford the quinoline acid 3D6 (2.43 g, 97%) as a pale yellow solid. MS: (M+H)+; 284. This material was used as is for the following reaction.

Step E: Compound 3D6 (2.43 g, 8.56 mmol) was put in diphenyl ether (20 mL) and the heterogeneous mixture was heated to 250° C. for 12 minutes before being cooled. The mixture was directly transferred to a silica gel column and eluted first with hexanes (to remove diphenyl ether), and then with 30% and 50% EtOAc/hexanes (Rf=0.48 in EtOAc/hexanes (1:1)). Evaporation of the solvent afforded the desired 2-thioethyl-8-chloro-4-hydroxyquinoline 3D7 (1.25g, 61%) as a pale yellow solid. MS: (M+H)+; 240, HPLC homogeneity=99%.

Example 3E

Preparation of 2-(2-methylpropyl)-8-chloro-4-hydroxyquinoline (3E4)

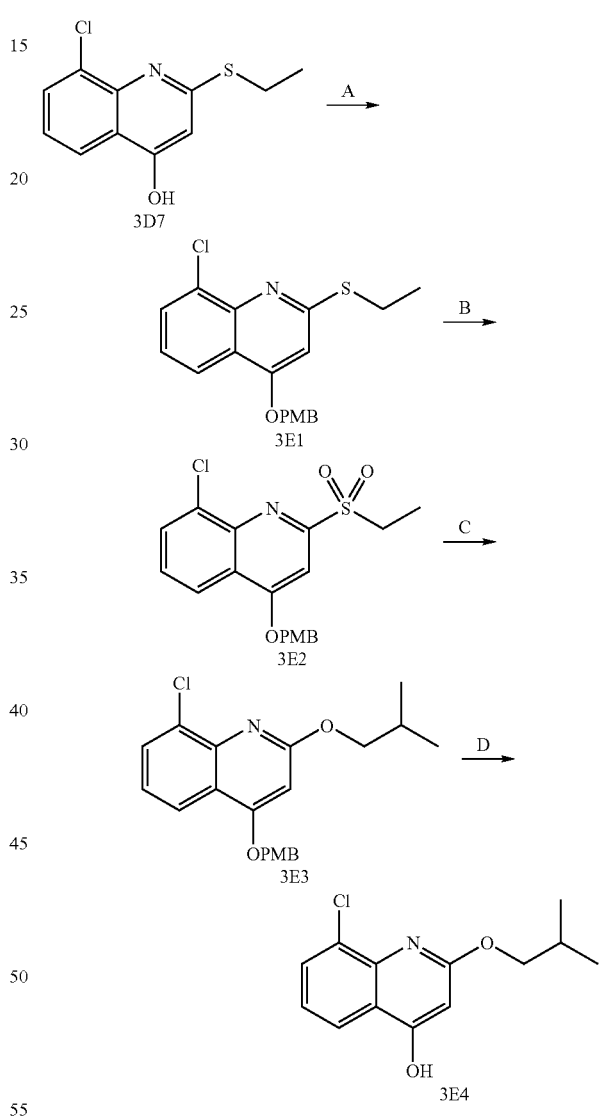

Step A: Quinoline 3D7 (75 mg, 0.31 mmol, 1 eq) was dissolved in anhydrous DMF (6 mL) and then treated with $K_2CO_3$ (138 mg, 1 mmol, 3.2 eq), To this suspension was added p-methoxybenzyl chloride (0.063 mL, 0.47 mmol, 1.5 eq) and the mixture stirred at R.T. for 24 hours. The reaction mixture was diluted with $H_2O$ (20 mL) and extracted using a mixture of diethyl ether/hexanes ((1:1), 3×40 mL). The organic phase was dried ($MgSO_4$), filtered and concentrated to afford a pale yellow oil that was purified on a silica gel column (eluent: 20% EtOAc/hexanes) to give the protected quinoline 3E1 (110 mg, 98%) as a clear oil.

Step B: To a solution of quinoline 3E1 (110 mg, 0.31 mmol, 1 eq) in methanol (3 mL) and diether ether (1 mL) was added water (1 mL). Oxone (564 mg, 0.92 mmol, 3 eq) was then added and the mixture was stirred at R.T. for 2 h. The reaction mixture was diluted in water (20 mL) and extracted with methylene chloride (3×20 mL) and finally washed with brine. The organic phase was dried (MgSO$_4$), filtered and concentrated to afford sulfone 3E2 (116 mg, 97%) as a pale yellow oil.

Step C: To a solution of sulfone 3E2 (116 mg, 0.296 mmol, 1 eq) in THF (3.0 mL) was added 2-methyl-1-propanol (2.0 mL, 10.83 mmol, 39 eq). The mixture was then treated with NaH (24 mg, 60%/oil, 0.592 mmol, 2 eq) and allowed to stir 45 min at R.T. The reaction was quenched by careful addition of H$_2$O (10 mL) and then extracted with diethyl ether (3×20 mL). The organic phases were combined, dried (MgSO$_4$), filtered and concentrated. The product was purified over a silica gel column (eluent: 5% EtOAc/hexanes) to afford the isobutoxy derivative 3E3 (87 mg, 79%) as a white solid.

Step D: To a solution of quinoline 3E3 (87 mg, 0.234 mmol) in methylene chloride (5 mL) was added slowly trifluoroacetic acid (5 mL) and the mixture allowed to stir for 15 min at R.T. The mixture was concentrated and then purified over silica gel column (eluent: 10% EtOAc/hexanes to afford after drying hydroxyquinoline 3E4 (56 mg, 95%) as a white solid. MS: 252 (M+H)+.

Example 3F

Preparation of 2-ethoxy-8-thiomethyl-4-hydroxyquinoline (3F4)

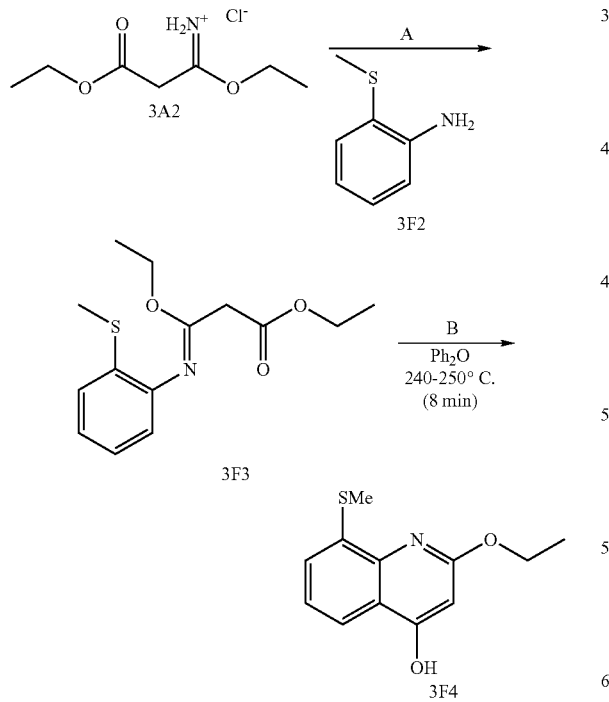

Step A: The imidate salt 3A2 (1.4 g, 7.2 mmol, 1 eq.) was combined with 2-(methylthio)aniline 3F2 (0.96 g, 7.50 mmol, 1 eq.) in ethanol (15 mL) under an N$_2$ atmosphere. The reaction mixture was stirred at R.T. (1 h) and monitored by HPLC. The reaction mixture was concentrated and then ether was added and the mixture filtered. The solids were washed with ether and the combined ether washes concentrated in vacuo. The resulting adduct 3F3 was obtained as a yellow oil (1.66 g, 82%) and used as is in the next step. MS electrospray: (M+H)+; 282 and (M−H)−; 280.

Step B: The condensation product 3F3 (1.66 g, 5.90 mmol) was dissolved in diphenyl ether (10 mL) and placed in a sand bath (300° C.). The internal temperature was monitored and maintained between 240-250° C. for 10 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 3F4 as a yellow solid (0.735 g, 53%). MS electrospray: (M+H)+; 236 and (M−H)−; 234.

Example 3G

Preparation of 2-ethoxy-8-(trimethylsilylethynyl)-4-hydroxyquinoline (3G3).

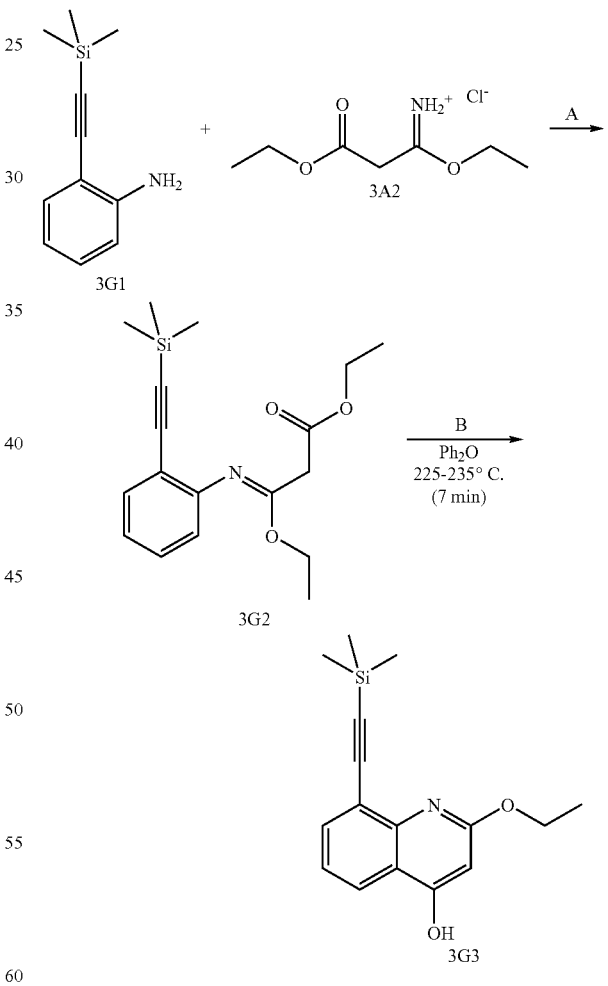

Step A: To 2-[(trimethylsilylethynyl)aniline] 3G1 (1.0 mL, 4.97 mmol, 1 eq) was added imidate 3A2 (0.972 g, 4.97 mmol, 1 eq) in abs. ethanol (15 mL) under a N$_2$ atmosphere. The mixture was stirred at R.T. for 48 h at which point the reaction was concentrated. The residue was taken up into diethyl ether and the salts removed by filtration. The concentrated mixture was purified on a silica gel column (eluent: EtOAc/hexanes (5:95)) to afford adduct 3G2 (1.28 g, 78%) as an oil. MS: 332 (M+H)+.

Step B: Adduct 3G2 (928 mg, 2.79 mmol) was dissolved in diphenyl ether (10 mL) and placed in a pre-heated sand bath (300° C.). The internal temperature was monitored and allowed to stay between 225° C.-235° C. for 7 minutes. The mixture was cooled and directly loaded on a silica gel column and eluted with hexanes to remove diphenyl ether, followed by a gradient of 30% to 50% EtOAc/hexanes. Concentration and drying in vacuo afforded the desired quinoline 3G3 (463 mg, 58%) as a beige solid. MS: 286 (M+H)+.

Note: Subsequent brosylate displacement with this TMS protected ethynyl quinoline 3G3 on the macrocyclic tripeptide gives directly the desired hydroxyquinoline analog with loss of the TMS group in situ.

Example 3H

Preparation of 2-ethoxy-8-methoxy-4-hydroxyquinoline (3H3)

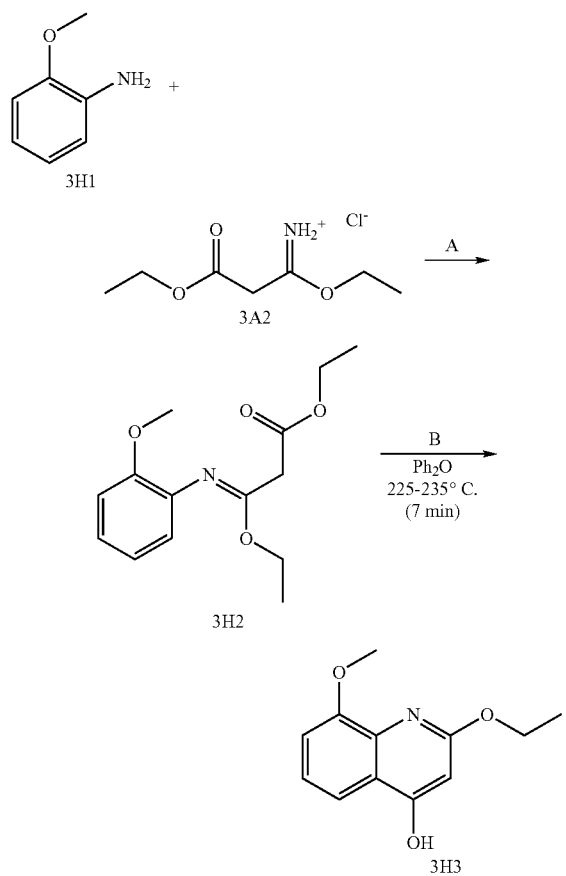

Step A and B: Beginning with ortho-anisidine 3H1 and following the same protocol as outlined in previous examples 3F and 3G, the desired 8-methoxyquinoline derivative 3H3 was obtained in 38% overall yield as a pale yellow solid. MS: 220 (M+H)+.

Example 3I

Preparation of 2-ethoxy-8-bromo-7-methoxy-4-hydroxyquinoline (3I2)

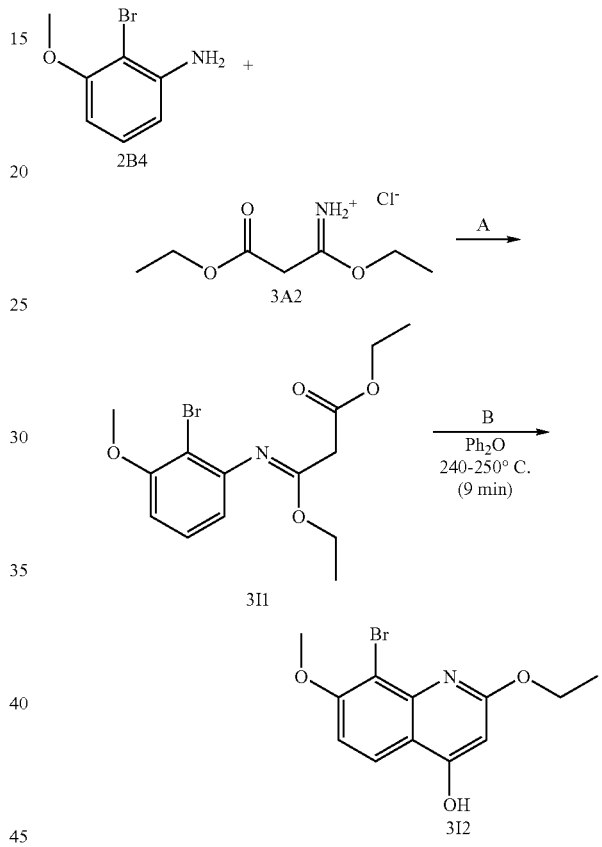

Step A: To 2-bromo-3-aminoanisole 2B4 (750 mg, 3.7 mmol, 1 eq) was added imidate 3A2 (0.73 g, 3.7 mmol, 1 eq) in ethanol (7 mL) under a $N_2$ atmosphere. The mixture was stirred at R.T. for 24 h at which point the reaction was concentrated and purified directly on a silica gel column (eluent: EtOAc/Hexanes (1:9)) to afford adduct 3I1 (1.12 g, 88%) as a pale yellow oil. MS: 344 (M+H)+ and 346 (MH+2)+.

Step B: Adduct 3I1 (1.12 g, 3.25 mmol) was dissolved in diphenyl ether (10 mL) and placed in a pre-heated sand bath (300° C.). The internal temperature was monitored and allowed to stay between 240° C.-250° C. for 8 minutes. The mixture was directly loaded on a silica gel column and eluted with hexanes to remove diphenyl ether, followed by a gradient of 30% to 50% EtOAc/hexanes: (Rf=0.25 in 1:1 EtOAc/hexanes). Concentration and drying in vacuo afforded the

Example 3J

Preparation of
8-bromo-7-methoxy-4-hydroxyquinolone (3J1)

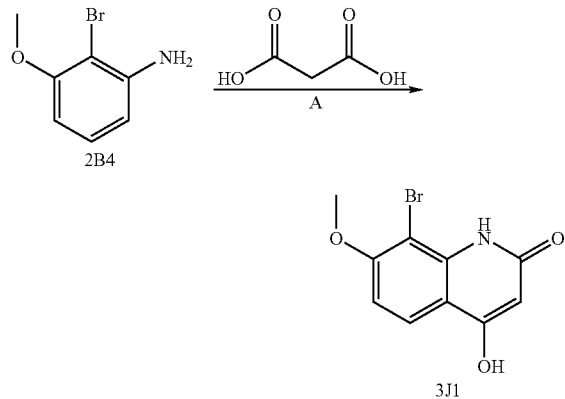

Step A: To 2-bromo-3-aminoanisole 2B4 (378 mg, 1.87 mmol, 1 eq) and malonic acid (194 mg, 1.87 mmol) was added phosphorous oxychloride (175 μL, 1.87 mmol). The reaction was placed in a pre-heated bath (95° C.) and stirred for 30 minutes. The mixture was cooled, and diluted with ice water and stirred ca. 2 h to afford a grey solid. This was filtered and washed with water until free of acid and then taken up into 1N NaOH. Insoluble material was removed by filtration and the resulting aqueous solution was treated with EtOH (8 mL) before adjusting the pH to 5-6 with 1N HCl (aq). The desired product was filtered and dried to afford quinolone 3J1 (0.12 g, 24%) as a yellow solid. MS: 270.0 (M+H)+ and 291.9 (M+Na)+.

Example 3K

Preparation of 5-ethoxythieno[3.2-b]pyridin-7-ol (3K3)

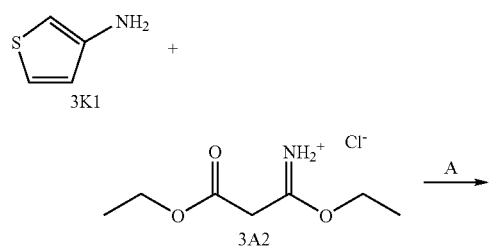

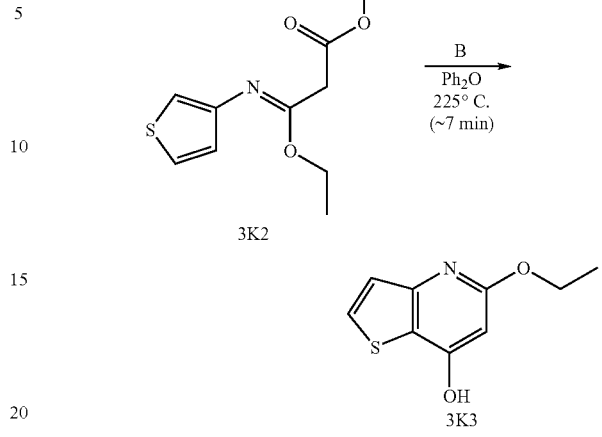

Step A: To available thiophen-3-ylamine 3K1 (0.50 g, 5.04 mmol) was added imidate 3A2 (1.08g, 5.5 mmol) in ethanol (10 mL) under a $N_2$ atmosphere. The mixture was stirred at R.T. for 3 h at which point the reaction was concentrated. To the residue was added ether, and the suspension filtered and washed with ether to afford adduct 3K2 (1.0g, 82%). This material was sufficiently clean to be used in the subsequent step. MS: 242.1 (MH)+.

Step B: Adduct 3K2 (1.0g, 4.14 mmol) was dissolved in diphenyl ether (5 mL) and placed in a pre-heated sand bath (300° C.). The internal temperature was monitored and allowed to stay between 210° C.-225° C. for 7 minutes. The mixture was directly loaded on a silica gel column and eluted with hexanes to remove diphenyl ether, followed by a gradient of 30% EtOAc/hexane to neat EtOAc. Concentration and drying in vacuo afforded the desired thieno[3.2-b]pyridinol 3K3 (200 mg, 25%) as a brown solid. MS: 196 (MH)+.

Example 3L

Preparation of
5-ethoxy-3-methylthieno[3.2-b]pyridin-7-ol (3L4)

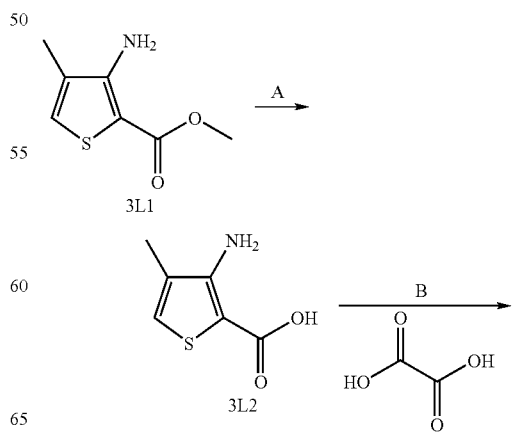

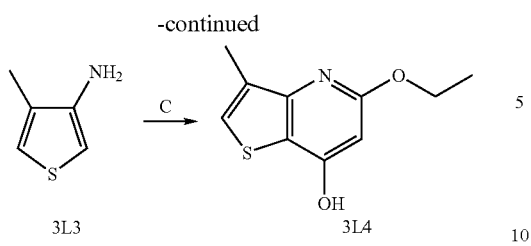

The method of J. M. Barker, P. R. Huddleston, M. L. Wood, Synth. Commun. (1995) 25(23): 3729 was followed for steps A and B.

Step A: 1M NaOH (20 mL) was added to compound 3L1 (1.5 g, 8.76 mmol). The mixture was heated at reflux for 3h, then cooled to RT, acidified to pH=1 with conc. HCl. The solution was filtered and rinsed once with minimal amount of hexanes. The solid that was obtained was dissolved in acetone/MeOH and dried over sodium sulfate, filtered and concentrated to obtain compound 3L2 as an off-white solid (1.37 g, 99%) which was immediately employed in subsequent step. LC-MS $t_R$=2.88 min, ES–=155.9.

Step B: To a suspension of amino acid 3L2 (1.38 g, 8.78 mmol) in i-PrOH (20 mL) was added oxalic acid (1.00 g, 11.11 mmol). This opaque solution was gently warmed to about 40° C. for 1 h until no starting material was observed by LC-MS. The mixture was cooled to RT, the solvent removed and the crude residue purified by flash column chromatography (4:1 to 1:1 to 1:4 hex:ETOAc) to yield the desired amine 3L3 (350 mg, 27%). $^1$H NMR (400 MHz, CDCl$_3$); 7.20 (br s, 2H), 6.86 (s, 1H), 6.00 (s, 1H), 1.99 (s, 3H).

Step C: Amine 3L3 was converted to compound 3L4 using a procedure analogous to that described in Example 3K.

Example 4

Synthesis of Compound 104 from Table 1

Step A: To a solution of the macrocyclic brosylate intermediate INRF12Brs (50 mg, 0.070 mmol, 1.0 eq.), dissolved in NMP (4 mL) was added the hydroxyquinoline 3A5 (15.7 mg, 0.070 mmol, 1.0 eq.) and cesium carbonate (25.09 mg, 0.077 mmol, 1.1 eq.). The mixture was heated at 70° C. for 16 hours. After the complete conversion of starting material to products, the reaction mixture was diluted with EtOAc and washed with H$_2$O (2×), saturated aq. NaHCO$_3$ (2×), and brine (1×). The organic layer was dried over anhydrous MgSO$_4$, filtered and evaporated to dryness. Product 41 (48.8 mg, 100%) was sufficiently pure to be used directly in the following step.

Step B: The methyl ester 41 (47.8 mg, 1.0 mmol) was dissolved in a solution of TH F/MeOH/H$_2$O(2:1:1, 1.2 mL) and saponified with 1N NaOH (0.56 mL, 0.56 mmol, 8 eq.). The hydrolysis reaction was carried out over 5 h at RT. Thereafter, the solution was evaporated to dryness to give an off-white solid. This material was dissolved in acetic acid and purified by preparative HPLC (AcCN/H$_2$O/TFA). Pure fractions were combined, frozen, and lyophilized to afford compound 104 as a white solid (12.3 mg; 26% yield), 97% homogeneity by analytical HPLC.

$^1$H NMR (400 MHz, DMSO-d$_6$): δ 8.51 (s, 1H), 7.93(d, J=8 Hz, 1H), 7.73(d, J=8 Hz, 1H), 7.21-7.15(m, 2H), 6.56 (s,

1H), 5.50-5.35 (m, 2H), 5.20 (bdd, J=9.4, 9.4 Hz, 1H), 4.50-4.40 (m, 4H), 4.40-4.30 (m, 1H), 4.1-3.8 (m, 2H underwater), 2.30-2.18 (m, 1H), 2.15-2.05 (m,1H), 1.75-1.60 (m,2H), 1.60-1.35 (m, 11H), 1.34 (t, J=7.1 Hz, 3H), 1.32-1.0 (m, 8H).

Example 5

Synthesis of Compounds 118 and 124 from Table 1

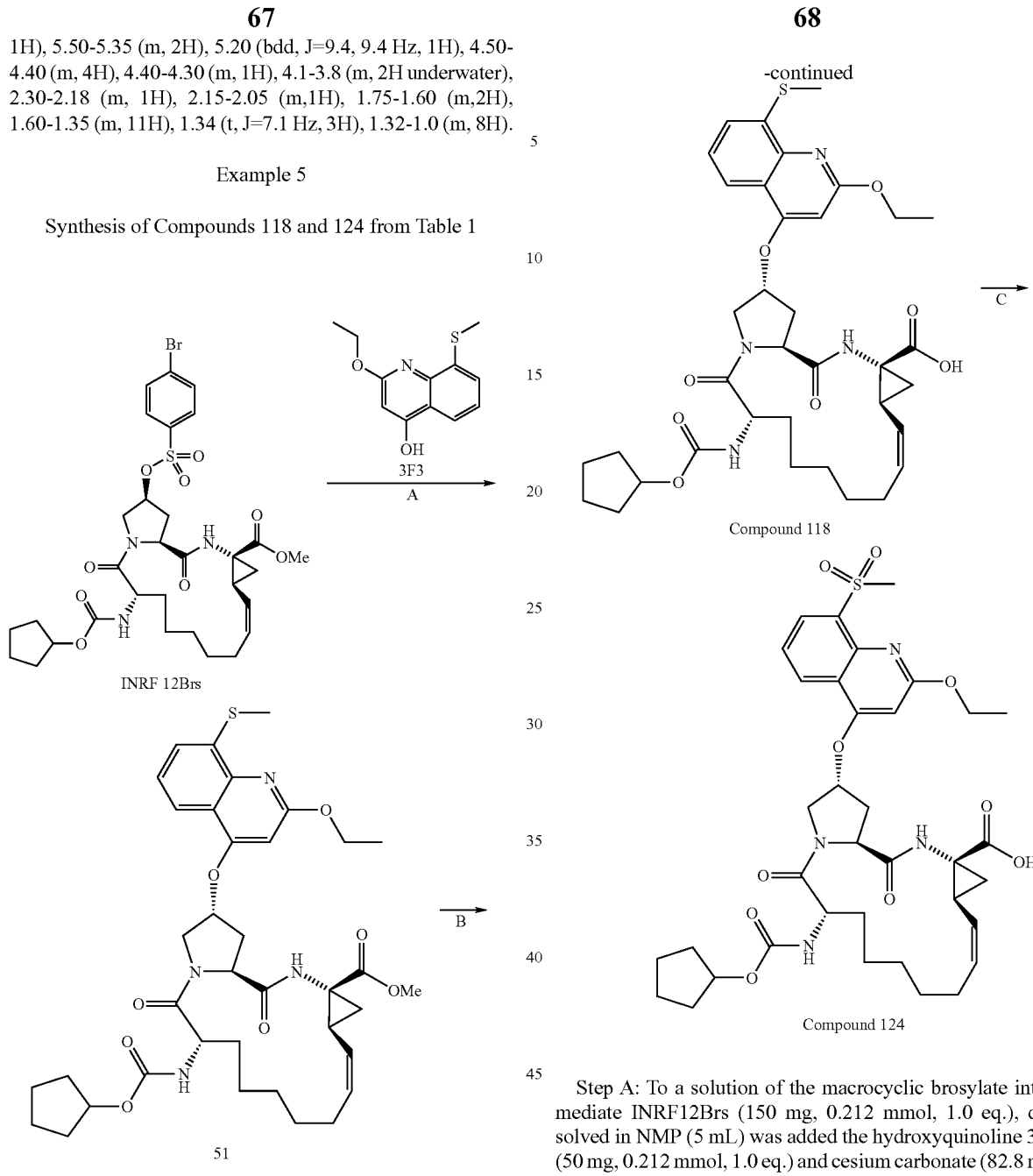

Step A: To a solution of the macrocyclic brosylate intermediate INRF12Brs (150 mg, 0.212 mmol, 1.0 eq.), dissolved in NMP (5 mL) was added the hydroxyquinoline 3F3 (50 mg, 0.212 mmol, 1.0 eq.) and cesium carbonate (82.8 mg, 0.254 mmol, 1.2 eq.). The mixture was heated at 70° C. for 16 hours. After the complete conversion of starting material to products, the reaction mixture was diluted with EtOAc and washed with H$_2$O (2×), saturated aq. NaHCO$_3$ (2×), and brine (1×). The organic layer was dried over anhydrous MgSO$_4$, filtered and evaporated to dryness. Product 51 (88 mg, 59%) was sufficiently clean to be used directly in the following step. MS: (MH)+; 709.3, (M−H)−; 707.3.

Step B: The methyl ester 51 (88 mg, 0.124 mmol) was dissolved in a solution of THF/MeOH (2 mL each) and then treated with 1N NaOH (2.0 mL, 2.0 mmol). The hydrolysis reaction was carried out over 18 h at RT. Thereafter, the solution was evaporated to dryness to give an off-white solid. This material was dissolved in acetic acid and purified by preparative HPLC (AcCN/H$_2$O/TFA). Pure fractions were combined, frozen, and lyophilized to afford compound 118 as a beige solid (57 mg; 66% yield). $^1$H NMR(400 MHz, DMSO-d$_6$): δ 8.57 (s, 1H), 7.76 (d, 1H, J=8 Hz), 7.35 (d, 1H, J=8 Hz), 7.27-7.20 (m, 2H), 6.55(s, 1H), 5.54-5.47(m, 1H), 5.41 (brs, 1H), 5.26 (t, 1H, J=9 Hz), 4.60-4.38 (m, 4H), 4.09 (brs, 1H), 3.84 (brd, 1H, J=9 Hz), 3.16 (s, 1H), 2.55(m, 1H), 2.43 (s, 3H), 2.31-2.14(m, 2H), 1.80-1.05(m, 23H); MS (MH)+; 695.4, (M−H)−; 693.3, analytical HPLC homogeneity=98.7%.

Step C: To a solution of compound 118 (35 mg, 0.050 mmol) in a 1:1 mixture of MeOH/water (1.5 mL each) was added Oxone® (0.154 g, 0.25 mmol) all at once. The reaction was stirred at RT for 7 h before being concentrated. The residue was taken up into methylene chloride (20 mL) and washed with water (2×20 mL) and sat. brine (3×20 mL). The organic phase was dried over MgSO$_4$, filtered and concentrated to give the desired crude product. The material was dissolved in AcOH and purified by preparative HPLC (Combiprep ODS-AQ, 20×50 mm) to give the desired compound 124 (2.5 mg, 7%) as a white solid. MS (MH)+; 727.3, (M−H)−; 725.3, analytical HPLC homogeneity=100%.

$^1$H NMR (400 MHz, DMSO-d$_6$): δ 8.59 (s, 1H), 8.36 (d, J=8 Hz, 1H), 8.25 (d, J=7 Hz, 1H), 7.49 (dd, J=8 Hz, 1H), 7.25 (d, J=7 Hz, 1H), 6.73 (s, 1H), 5.55-5.47 (m, 2H), 5.25 (dd, J=9 Hz, 1H), 4.58-4.47 (m, 3H), 4.46-4.39 (m, 1H), 4.10-4.01 (m, 2H), 3.83 (d, J=9 Hz, 1H), 3.53 (s, 3H), 2.35-2.26 (m, 1H), 2.19-2.10 (m, 1H), 1.77-1.66 (m, 2H), 1.56-1.38 (m, 13H), 1.38-1.25 (m, 7H), 1.24-1.08 (m, 2H).

Example 6

Synthesis of Cyclopropylsulfonamide Intermediate 64

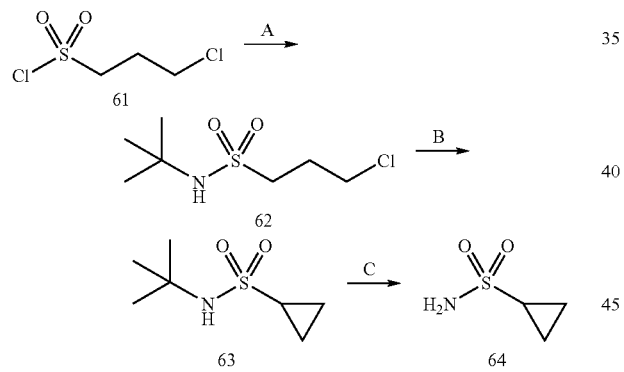

Step A: A dry 3 L 3-neck flask equipped with a magnetic stir bar, addition funnel and argon inlet was flushed with argon, then charged with 3-chloropropanesulfonyl chloride 61 (100.48 g, 0.57 mol, 1.0 eq). Anhydrous dichloromethane (900 mL) was transferred into the flask via cannula, the mixture was cooled in an ice/water bath and tert-butylamine (72 mL, 0.68 mol, 1.2 eq) was added. The mixture was stirred 15 minutes then a solution of triethylamine (158 mL, 1.13 mol, 2.0 eq) in anhydrous dichloromethane (100 mL) was added dropwise over 45 minutes and stirring was continued for 1 h. The mixture was diluted with dichloromethane (500 mL) and washed with 1N HCl (3×400 ml) and brine. The organic layer was dried over sodium sulfate, filtered and evaporated to dryness to give compound 62 as an orange-beige solid (107.04 g, 88% yield). $^1$H NMR (CDCl$_3$, 400 MHz): δ 4.46 (s, 1H), 3.71 (tr, 2H), 3.25 (tr, 2H), 2.31 (m, 2H), 1.41 (s, 9H).

Step B: A dry 5 L 3-neck flask equipped with a magnetic stir bar, argon inlet and 2 addition funnels was flushed with argon and anhydrous THF (1.5 L) was transferred into the flask via cannula and cooled to −78° C. Compound 62 (96.73 g, 0.453 mol, 1.0 eq) was dissolved in anhydrous THF (390 mL) and the solution was transferred into one of the addition funnels. n-Butyllithium solution (2.5 M in hexanes, 390 mL, 0.975 mol, 2.15 eq) was transferred to the other addition funnel and the solutions in the addition funnels were added to the flask simultaneously over 4 hours. When addition was complete, the mixture was allowed to warm to room temperature. Once the internal temperature reached ~0° C., the reaction was quenched by dropwise addition of saturated NH$_4$Cl solution (200 mL). The THF was removed under vacuum and the residue was diluted with CH$_2$Cl$_2$ (2 L) and water (1 L). The layers were separated and the organic layer was washed with water (2×1 L) and brine (800 mL), dried over sodium sulfate, filtered and evaporated to dryness. Compound 63 was obtained as an orange-beige solid (77.32 g, 96% yield). $^1$H NMR (CDCl$_3$, 400 MHz): δ 4.25 (s, 1H), 2.48 (m, 1H), 1.42 (s, 9H), 1.19 (m), 1.01 (m).

Step C: A 2L flask equipped with a magnetic stir bar and condenser was charged with Compound 63 (82.53 g, 0.466 mol, 1.0 eq), dichloromethane (400 mL) and trifluoroacetic acid (460 mL, 5.97 mol, 13 eq). The mixture was heated to reflux for 2 h, allowed to cool, and evaporated and co-evaporated several times with CH$_2$Cl$_2$ to remove most of the TFA. The crude product was dissolved in 95:5 CH$_2$Cl$_2$:MeOH and NH$_4$OH and was purified by silica gel column chromatography (94:5:1 CH$_2$Cl$_2$:MeOH:NH$_4$OH). Compound 64 was obtained as a beige solid (46.38 g, 78% yield). $^1$H NMR (DMSO-d$_6$, 400 MHz): δ 6.79 (s, 2H), 2.54 (1H, under DMSO peak), 0.92 (4H).

Example 7

Synthesis of Compound 136 from Table 1.

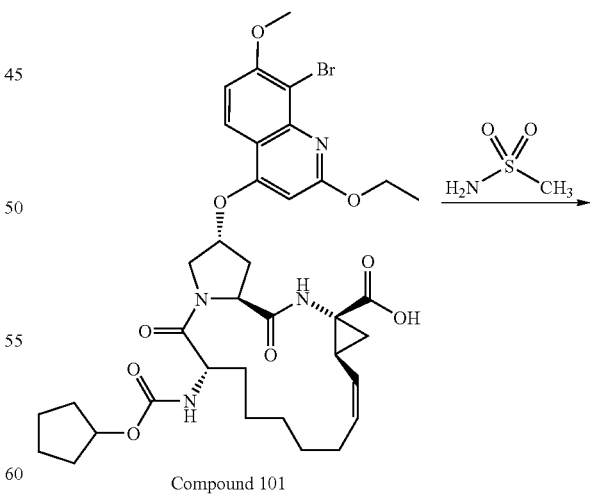

Compound 101

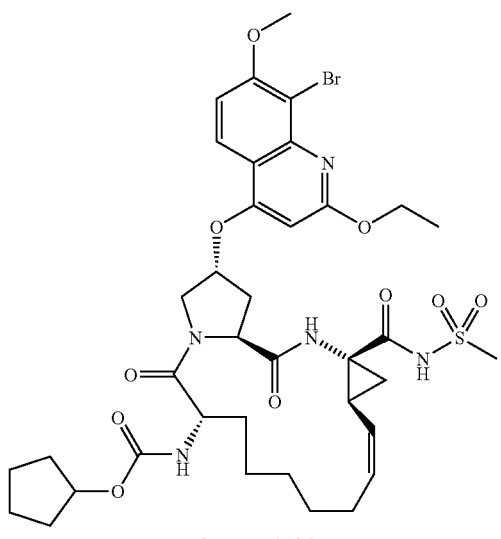

Compound 136

Compound 101 (Table 1) (24 mg, 0.032 mmol), prepared from INRF12Brs and 2-ethoxy-8-bromo-7-methoxy-4-hydroxy quinoline (312; Example 31) using a procedure analogous to the one described in Example 4, was combined with HATU (14 mg, 0.038 mmol) in anhydrous DMF (4 mL). The solution was stirred at R.T. before DIPEA (22 µL, 0.13 mmol) was added dropwise over ca. 1 min. The mixture was stirred for 1 h at R.T. and analyzed by analytical HPLC for the formation of the activated ester. A solution of methanesulfonamide (12 mg, 0.13 mmol), DMAP (15 mg, 0.12 mmol) and DBU (19 µL, 0.13 mmol) were added in DMF (1 mL). The reaction mixture was stirred 48 h at R.T. before being concentrated. The reaction mixture was poured into EtOAc (50 mL) and washed with sat. NaHCO$_3$ (aq) and sat. brine, before being dried over Na$_2$SO$_4$, filtered and concentrated. The residue was reconstituted in DMSO and purified by preparative HPLC. Lyophilization of pure fractions gave the Compound 136 (7.8 mg, 29%) as a white amorphous solid. MS: 834.2 (M+H)+ and 836.2 (MH+2)+.

$^1$H NMR (400 MHz, DMSO-d$_6$) δ 11.17 (s, 1H), 8.95 (s, 1H), 7.99 (d, J=9 Hz, 1H), 7.33 (d, J=7 Hz, 1H), 7.15 (d, J=9 Hz, 1H), 6.49 (s, 1H), 5.57 (dd, J=9 Hz, 1H), 5.46 (bs, 1H), 5.14 (dd, J=9.5, 9.5 Hz, 1H), 4.63-4.55 (m, 1H), 4.50 (q, J=7 Hz, 2H), 4.44-4.33 (m, 2H), 4.09-3.99 (m, 2H), 3.94 (s, 3H), 3.83 (d, J=8.6 Hz, 1H), 3.16 (s, 3H), 2.65-2.53 (m, 1H), 2.35-2.25 (m, 1H), 1.77-1.45 (m, 14H), 1.39 (t, J=7 Hz, 3H), 1.38-1.08 (m, 7H).

Compounds of formula (I) wherein R$^1$ is NHSO$_2$R$^{11}$ and R$^{11}$ is cyclopropyl may be prepared by the method of Example 7 but using cyclopropylsulfonamide 64 in place of methanesulfonamide.

Example 8

Synthesis of Compound 135 (Table 1):

Preparation of Sulfamide Intermediate 83:

Step A: Reagent 81 (0.3 g, 0.99 mmol) [prepared according to Winum, J-Y; Toupet, L; Barragan, V; Dewynter, G; Montero, J-L., Org. Left., 14(3), 2241-2243 (2001)] was suspended in CH$_2$Cl$_2$, morpholine (0.086 mL, 0.99 mmol) was added and the mixture was stirred for 5 h. The reaction was followed by TLC. On completion the reaction mixture was directly adsorbed on silica gel and the product was eluted with 6% MeOH in CHCl$_3$ to afford 0.258 g (98%) of compound 82 as a white solid.

Step B: Compound 82 (0.150 g, 0.56 mmol) was dissolved in CH$_2$Cl$_2$ (5 mL) and treated with TFA (1 mL). The reaction was stirred for 4 h and monitored by TLC. Upon completion, the solvent was evaporated and the residue directly adsorbed on the silica gel and eluted with 5% MeOH in CHCl$_3$ to afford 0.075 g (80.2%) of compound 83 as a white solid.

Synthesis of Compound 135 (Table 1)

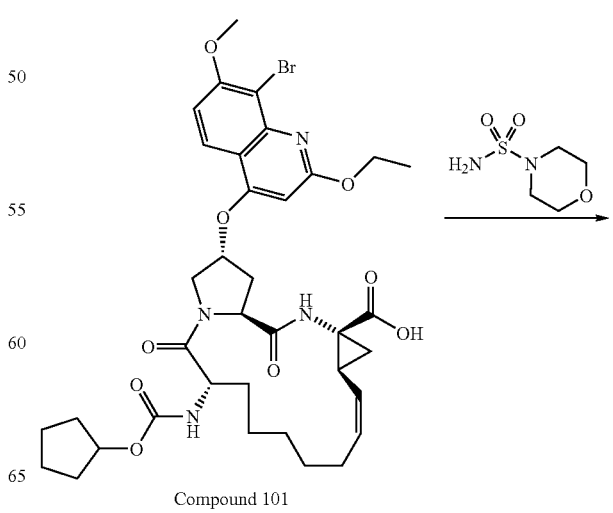

Compound 101

-continued

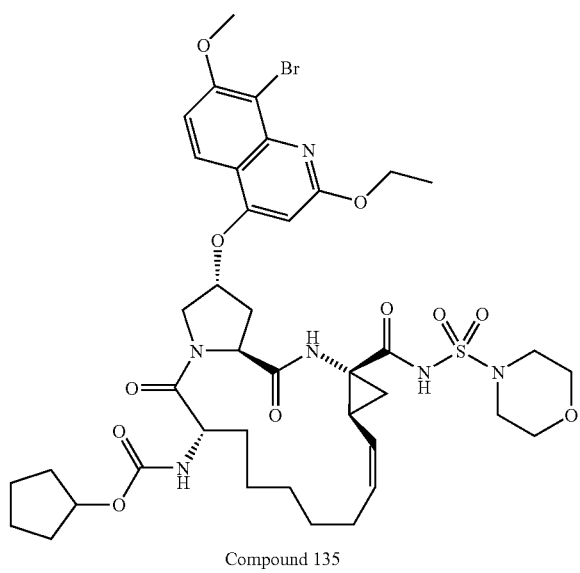

Compound 135

Compound 101 (24 mg, 0.032 mmol) (described in Example 7) was combined with HATU (14 mg, 0.038 mmol) in anhydrous DMF (4 mL). The solution was stirred at R.T. before DIPEA (22 µL, 0.13 mmol) was added dropwise over ca. 1 min. The mixture was stirred for 1 h at R.T. and analyzed by analytical HPLC for the formation of the activated ester. A solution of compound 83 (21 mg, 0.13 mmol), DMAP (15 mg, 0.12 mmol) and DBU (19 µL, 0.13 mmol) were added in DMF (1 mL). The reaction mixture was stirred 48 h at R.T. before being concentrated. The reaction mixture was poured into EtOAc (50 mL) and washed with sat. NaHCO$_3$ (aq) and sat. brine, before being dried over Na$_2$SO$_4$, filtered and concentrated. The residue was reconstituted in DMSO and purified by preparative HPLC. Lyophilization of pure fractions gave the sulfamide derivative Compound 135 (7.5 mg, 26%) as a white amorphous solid. MS: 905.3 (M+H)$^+$ and 907.3 (MH+2)$^+$.

$^1$H NMR (400 MHz, DMSO-d$_6$) δ 10.93 (s, 1H), 8.85 (s, 1H), 7.99 (d, J=9 Hz, 1H), 7.33 (d, J=6.5 Hz, 1H), 7.15 (d, J=9 Hz, 1H), 6.48 (s, 1H), 5.68-5.56 (m, 1H), 5.50-5.42 (m, 1H), 5.13-5.10 (m, 1H), 4.59 (bd, J=8 Hz, 1H), 4.55-4.43 (m, 3H), 4.40 (dd, J=7.0, 7.0 Hz, 1H), 4.10-4.0 (m, 1H), 3.94 (s, 3H), 3.84 (bd, J=9 Hz, 1H), 3.60-3.53 (m, 4H), 3.17-3.06 (m, 4H), 2.70-2.57 (m, 1H), 2.35-2.23 (m, 1H), 1.78-1.48 (m, 14H), 1.39 (t, 3H), 1.34-1.10 (m, 7H).

Example 9

Parallel Synthesis of Compounds Exemplified in Table 2:

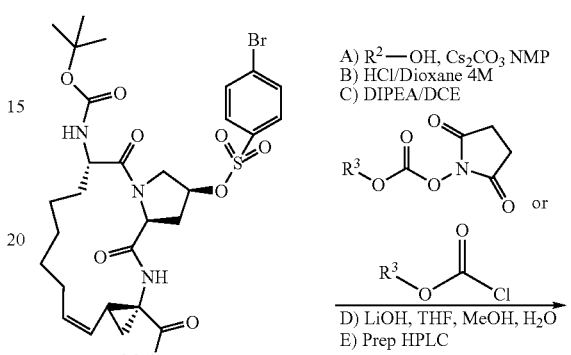

91

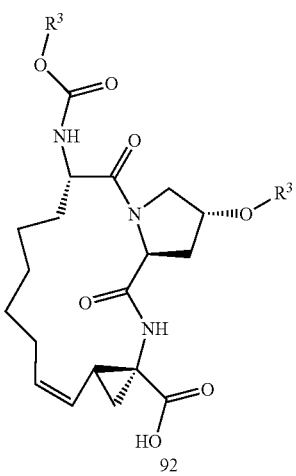

92

Step A: A series of 8-mL vials were disposed in a reaction block. In each vial was successively added the brosylate (0.07 mmol, 48.9 mg), NMP (1 mL), the building block R$^2$—OH (0.08 mmol) and cesium carbonate (0.12 mmol, 37.6 mg). The closed vials were placed in an oil bath at 70° C. for 18 h. Each reaction mixture was diluted with EtOAc (10 mL) and successively washed with water, saturated aqueous NaHCO$_3$ and brine. After the usual treatment (MgSO$_4$, filtration and concentration), the crude materials were purified by flash chromatography (SiO$_2$, elution with hexane-EtOAc, 1:1 to 4:6 for diverse 4-hydroxy quinolines). The purified compounds were transferred into 8-mL vials, vacuum centrifuged to remove the solvent and weighed (the amount of desired material varied between 0.02 and 0.025 mmol).

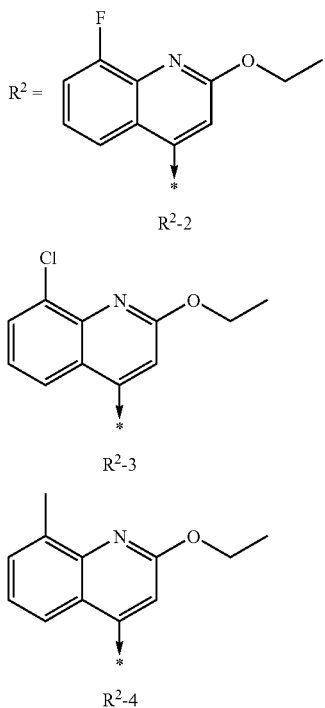

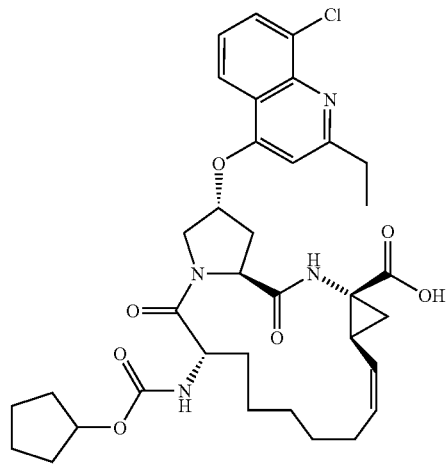

Example 10

Compound 116 (Table 1)

Step B: Removal of the Boc protecting group. All the vials were treated with 4M HCl in dioxane (1 mL) for 1 h and vacuum centrifuged to remove the volatiles.

Step C: In vials was added the corresponding R³-carbonate (approximately 2 eq. based on the yield of the first step) (0.04 mmol) and DIPEA (0.09 mmol, 16 µL) in DCE (500 µL) or the corresponding R³-chloroformate (approximately 3 eq. based on the yield of the first step) (0.06 mmol) and DIPEA (0.09 mmol, 16 µL) in DCE (500 µL). The reactions were allowed to proceed overnight. All vials were then vacuum centrifuged to remove the volatiles.

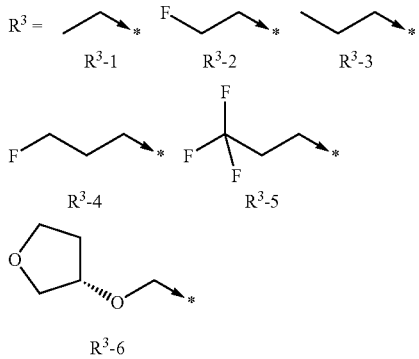

Step D: All reactions were diluted with 1 mL of THF and 500 µL of MeOH. A solution of 500 µL of 2N aq. LiOH (1 mmol) was then added and the solutions were allowed to react overnight. The reaction mixtures were then vacuum centrifuged to remove the volatile material, diluted with 500 µL of DMSO and neutralized by the addition of 400 µL of AcOH.

Step E: All compounds were purified by semi-prep reversed-phase HPLC (Symmetry column 5 cm×19 cm, $CH_3CN/H_2O$ 0.06% TFA gradient).

$^1$H NMR (400 MHz, DMSO-$d_6$) δ 12.25 (bs, 1H), 8.57 (s, 1H), 8.12 (d, J=8 Hz, 1H), 7.88 (d, J=7 Hz, 1H), 7.38 (dd, J=8, 8 Hz, 1H), 7.24 (d, J=7 Hz, 1H), 7.14 (s, 1H), 5.62-5.45 (m, 2H), 5.26 (dd, J=9, 9 Hz, 1H), 4.70-4.53 (m, 2H), 4.41 (dd, J=8 Hz, 1H), 4.13-4.04 (m, 2H), 3.86 (m, 2H), 2.95 (q, J=8 Hz, 2H), 2.62-2.50 (m, 1H), 2.37-2.25 (m, 1H), 2.22-2.12 (m, 1H), 1.80-1.60 (m, 3H), 1.60-1.36 (m, 13H), 1.34 (t, 3H), 1.25-1.08 (m, 2H).

Compound 205 (Table 2)

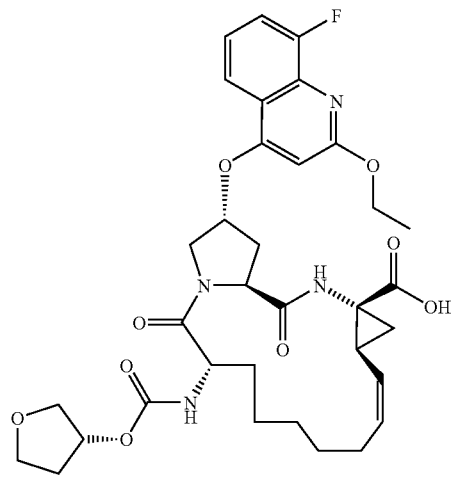

$^1$H NMR (400 MHz, DMSO-$d_6$) δ 12.2(bs, 1H), 8.58 (S, 1H), 7.81 (d, J=8 Hz, 1H), 7.50-7.42 (m, 2H), 7.31-7.23 (m, 1H), 6.92 (s, 1H), 5.55-5.50 (m, 1H), 5.48-5.43 (m, 1H), 5.26 (dd, J=8, 8 Hz, 1H), 4.71-4.65 (m, 1H), 4.45 (q, J=7 Hz, 2H), 4.45-4.35 (m, 1H), 4.13-4.05 (m, 1H), 3.85 (dd, J=8, 8 Hz,

1H), 3.65-3.52 (m, 4H), 3.48(d, J=10 Hz, 1H), 2.62-2.53 (m, 1H), 2.48-2.42 (m, 1H), 2.35-2.25 (m, 1H), 2.16 (dd, J=9 Hz, 1H), 1.93-1.80 (m, 1H), 1.79-1.65 (m, 3H), 1.60-1.51 (m, 1H), 1.50-1.42 (m, 3H), 1.37 (t, J=7 Hz, 3H), 1.36-1.05 (m, 5H).
Compound 306 (Table 3)
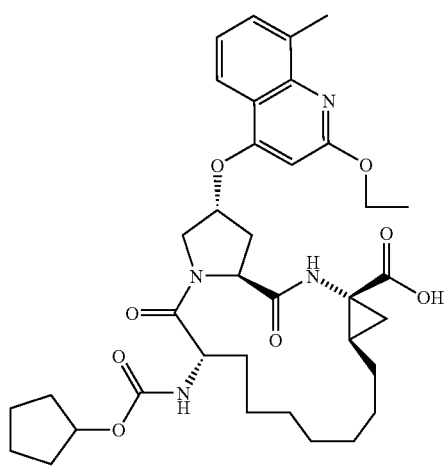
(306)
$^1$H NMR (400 MHz, DMSO-d$_6$) δ 12.4 (bs, 1H), 8.46 (s, 1H), 7.84 (d, J=8 Hz, 1H), 7.49 (d, J=7 Hz, 1H), 7.18 (dd, J=7.5, 7.5 Hz, 1H), 7.075 (d, J=7 Hz, 1H), 6.50 (s, 1H), 5.37 (bs, 1H), 4.71-4.6 (m, 2H), 4.47 (q, J=7 Hz, 2H), 4.44-4.35 (m, 2H), 4.26-4.15 (m, 1H), 3.82 (bd, J=8 Hz, 1H), 2.57 (s, 3H), 2.45-2.35 (m, 1H), 2.35-2.23 (m, 1H), 1.80-1.00 (m, 25H), 1.39 (t, J=7 Hz, 3H).
Example 11
Synthesis of Compound 402 (Table 4)
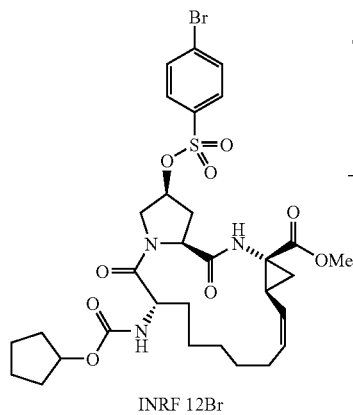
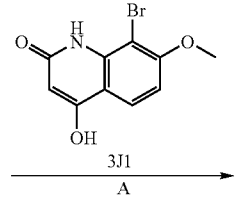
INRF 12Br
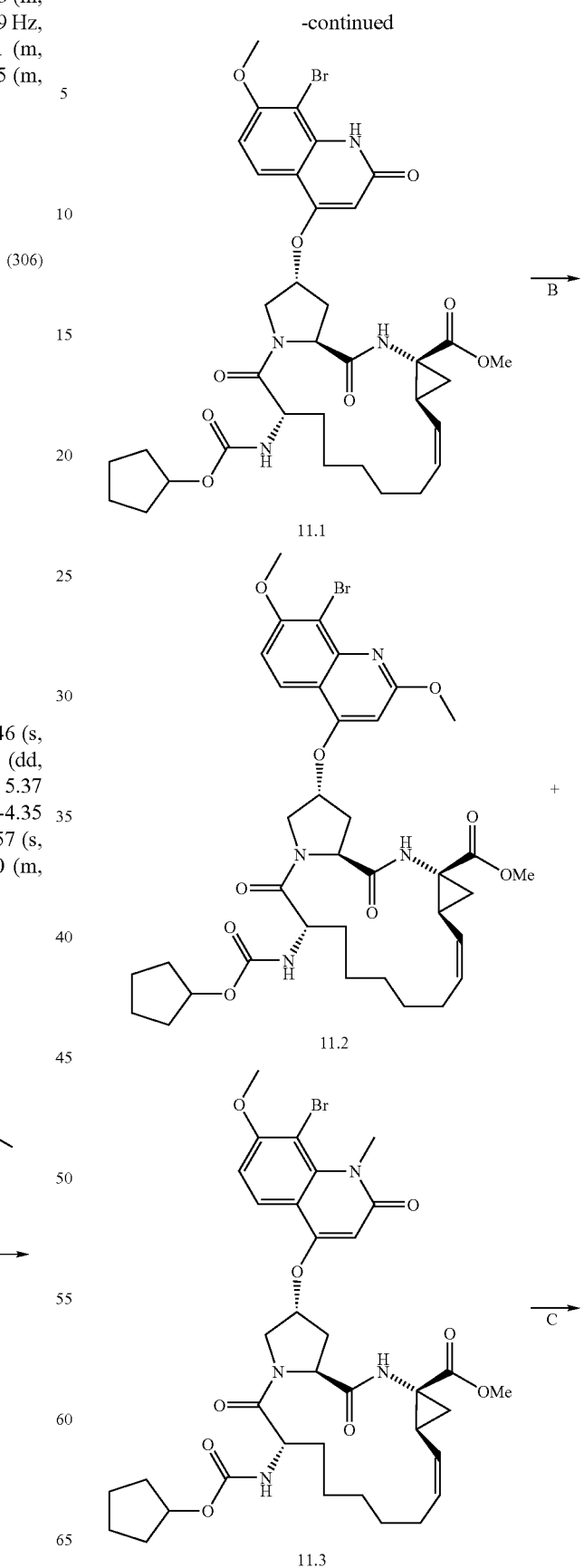

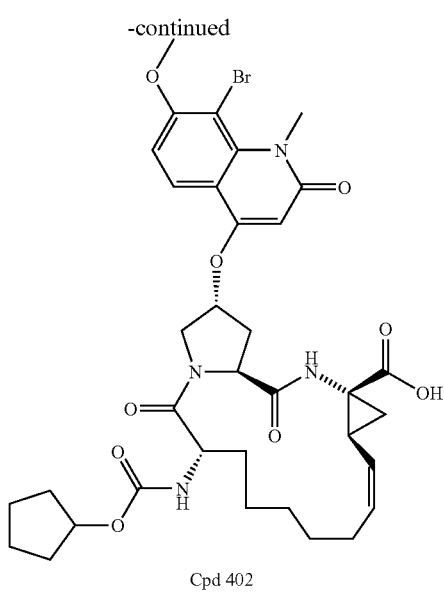

Cpd 402

Step A. To a solution of the macrocyclic brosylate intermediate INRF12Br (318 mg, 0.448 mmol, 1.0 eq.), dissolved in NMP (10 mL) was added the hydroxyquinolone 3J1 (121 mg, 0.448 mmol, 1.0 eq.) and cesium carbonate (153 mg, 0.47 mmol, 1.1 eq.). The mixture was heated at 70° C. for 24 hours. After the complete conversion of starting material to products, the reaction mixture was diluted with EtOAc and washed with $H_2O$ (2×), saturated aq. $NaHCO_3$ (2×), and brine (1×). The organic layer was dried over anhydrous $Na_2SO_4$, filtered and evaporated to dryness. The crude reaction material was purified by chromatography ($SiO_2$, EtOAc) to give product 11.1 (143 mg, 43%) as a white solid. MS: 743.3 (M+H)+ and 745.3 (MH+2)+.

Step B. Alkylation of the quinolone adduct 11.1 (70 mg, 0.094 mmol) was 15 accomplished in acetonitrile (5 mL) with MeI (58 µL, 0.93 mmol) with potassium carbonate (26 mg). The reaction was stirred at 70° C. for 5 h before a second amount of MeI was added (58 µL, 0.93 mmol). The mixture was stirred a further 16h before being concentrated. The residue was suspended in chloroform, filtered to remove salts, and concentrated to give a mixture of compounds 11.2 and 11.3 as a white solid. MS: 757.3 (M+H)+, (MH+2)+, 759.3. This mixture was used as such in the next step.

Step C. The methyl esters 11.2 and 11.3 (71 mg, 0.094 mmol) were dissolved in a solution of THF/MeOH/$H_2O$ (2:1:1, 2 mL) and saponified with 1N NaOH (0.75 mL, 0.75 mmol, 8 eq.). The hydrolysis reaction was carried out over 5h at RT. Thereafter, the solution was evaporated to dryness to give an off-white solid. This material was dissolved in acetic acid and purified by preparative HPLC (AcCN/$H_2O$/TFA). Pure fractions were combined, frozen, and lyophilized to afford the cyclic tripeptide Cpd 402 as a white solid (4.3 mg; 22% yield), 98% homogeneity by analytical HPLC. MS: 743.2 (M+H)+ and 745.2 (MH+2)+.

$^1$H NMR (400 MHz, DMSO-$d_6$) δ 12.21 (bs, 1H), 8.57 (s, 1H), 7.88 (d, J=9 Hz, 1H), 7.21 (d, J=7 Hz, 1H), 6.98 (d, J=9 Hz, 1H), 6.03 (s, 1H), 5.50 (dd, J 8,8 Hz, 1H), 5.34 (bs, 1H), 5.26 (dd, J=10 Hz, 1H), 4.53-4.36 (m, 3H), 4.09-4.00 (m, 1H), 3.92 (s, 3H), 3.80-3.73 (m, 1H), 3.70 (s, 3H), 2.47-2.39 (m, 1H), 2.33-2.20 (m, 1H), 2.19-2.09 (dd, J=9, 9 Hz, 1H), 1.79-1.56 (m, 3H), 1.56-1.23 (m, 15H), 1.23-1.05 (m, 2H).

Example 12

NS3—NS4A Protease Assay

The enzymatic assay used to evaluate the present compound is described in WO 00/09543 and WO 00/59929.

Example 13

Cell-based Luciferase Reporter HCV RNA Replication Assay

The cell-based HCV RNA replication assay used to evaluate the present compounds is described as follows:

Cell Culture:

Huh-7 cells that stably maintained a subgenomic HCV replicon containing the luciferase-FMV2A-neomycin phosphotransferase fusion gene were established as previously described (Lohman et al., 1999. Science 285: 110-113) and designated as MP-1 cells. MP-1 cells are maintained in Dulbecco's Modified Earle Medium (DMEM) supplemented with 10% FBS and 0.25 mg/mL neomycin (standard medium). The cells are passaged by trypsinization and frozen in 90% FBS/10% DMSO. During the assay, DMEM medium supplemented with 10% FBS, containing 0.5% DMSO and lacking neomycin used (Assay medium). The day of the assay, MP-1 cells are trypsinized and diluted to 100 000 cells/mL in assay medium. 100 uL is distributed into each well of a black 96-well ViewPlate™ (Packard). The plate is then incubated at 37° C. with 5% $CO_2$ for two hours.

| Reagents and Materials | | | |
|---|---|---|---|
| Product | Company | Catalog # | Storage |
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Geneticin (G418) | Gibco-BRL | 10131-027 | −20° C./4° C. |
| Trypsin-EDTA | Gibco-BRL | 25300-054 | −20° C./4° C. |
| ViewPlate ™-96, Black | Packard | 6005182 | RT |
| Backing tape, Black | Packard | 6005189 | RT |
| PVDF 0.22 µm Filter Unit | Millipore | SLGV025LS | RT |
| Deep-Well Titer Plate Polypropylene | Beckman | 267007 | RT |

Preparation of Test Compound:

The test compound in 100% DMSO was first diluted in assay medium to a final DMSO concentration of 0.5%. The solution was sonicated for 15 min and filtered through a 0.22 µM Millipore Filter unit. Into column 3 of a Polypropylene Deep-Well Titer Plate, the appropriate volume is transferred into assay medium to obtain the starting concentration (2×) to be tested. In columns 2 and, 4 to 12 add 200 µL of assay medium (containing 0.5% DMSO). Serial dilutions (1/2) are prepared by transferring 200 µL from column 3 to column 4, then from column 4 to column 5, serially through to column 11. Columns 2 and 12 are the no inhibition controls.

Addition of Test Compound to Cells:

A volume of 100 µL from each well of the compound dilution plate is transferred to a corresponding well of the Cell Plate (Two columns will be used as the "No inhibition control"; ten [10] columns are used for the dose response). The cell culture plate was incubated at 37° C. with 5% $CO_2$ for 72 hours.

Luciferase Assay:

Following the 72h incubation period, the medium is aspirated from the 96-well assay plate and a volume of 100 μL of 1× Glo Lysis Buffer (Promega) previously warmed to room temperature was added to each well. The plate was incubated at room temperature for 10 min with occasional shaking. A black tape was put at the bottom of the plate. 100 μL of Bright-Glo luciferase substrate (Promega) previously warmed to room temperature was added to each well followed by gentle mixing. The luminescence was determined on a Packard TopCount instrument using the Data Mode Luminescence (CPS) with a count delay of 1 min and a count time of 2 sec.

| Product | Company | Catalog # | Storage |
| --- | --- | --- | --- |
| Glo Lysis Buffer | Promega | E266A | 4° C. |
| Bright-Glo Luciferase Assay System | Promega | E2620 | −20° C. |

The luminescence determination (CPS) in each well of the culture plate was a measure of the amount of HCV RNA replication in the presence of various concentrations of inhibitor. The % inhibition was calculated with the following equation:

% inhibition=100−[CPS (inhibitor)/CPS (control)× 100]

A non-linear curve fit with the Hill model was applied to the inhibition-concentration data, and the 50% effective concentration ($EC_{50}$) was calculated by the use of SAS software (Statistical Software; SAS Institute, Inc. Cary, N.C.).

When the compounds of this invention are evaluated in the preceding enzymatic and cell based assays, the compounds are found to be highly active. More specifically, the compounds have $IC_{50}$ values below 100 nM in the NS3-NS4A protease assay, and $EC_{50}$ values below 100 nM in the cell-based luciferase reporter HCV RNA replication assay.

Example 14

Specificity Assays

The specificity assays used to evaluate the selectivity of this compound are described in WO 00/09543.

When the compounds are evaluated in the specificity assays, the compounds of formula 1 are found to be selective in that they do not show significant inhibition (no measurable activity at concentrations up to 30 pM) in the Human Leukocyte Elastase and Cathepsin B assays.

Tables of Compounds

The following tables list compounds representative of the invention. All compounds listed in Tables 1 to 5 were found to have $IC_{50}$ values below 100 nM in the NS3-NS4A protease assay of Example 12. In addition, many of the compounds listed in Table 1 have $EC_{50}$ values below 100 nM in the cell-based luciferase reporter HCV RNA replication assay of Example 13. Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

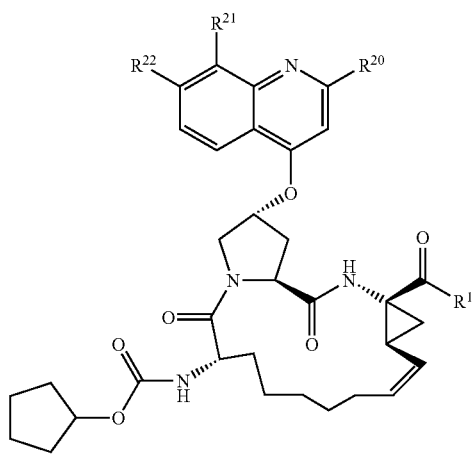

| Cpd | $R^{22}$ | $R^{21}$ | $R^{20}$ | $R^1$ | $t_R$ | $(MH)^+$ | $(MH + 2)^+$ |
| --- | --- | --- | --- | --- | --- | --- | --- |
| 101 | OMe | Br | OEt | OH | 6.9 | 757.3 | 759.3 |
| 102 | OMe | Me | OEt | OH | 5.6 | 693.4 | |
| 103 | H | Br | OEt | OH | 7.4 | 725.2 | 727.2 |
| | | | | | | $(M − H)^-$ | $(M − H + 2)^-$ |
| 104 | H | Cl | OEt | OH | 7.2 | 685.3 | 685.3 |
| 105 | H | Br | OMe | OH | 6.0 | 713.2 | 715.2 |

TABLE 1-continued

| Cpd | R22 | R21 | R20 | R1 | $t_R$ | (MH)+ | (MH + 2)+ |
|---|---|---|---|---|---|---|---|
| 106 | H | Cl | OMe | OH | 5.8 | 669.3 | 671.3 |
| 107 | H | F | OMe | OH | 5.2 | 653.3 | |
| 108 | OMe | Me | OMe | OH | 4.6 | 679.3 | |
| 109 | OMe | Me | H | OH | 4.3 | 649.3 | |
| 110 | H | Cl | H | OH | 4.7 | 639.2 | 641.2 |
| 111 | H | Br | H | OH | 5.1 | 683.2 | 685.2 |
| 112 | H | Cl | Me | OH | 5.1 | 653.3 | 655.3 |
| 113 | H | F | OEt | OH | 7.4 | 667.3 | |
| 114 | H | Me | OEt | OH | 6.8 | 663.4 | |
| 115 | H | Br | Me | OH | 5.2 | 697.3 | 699.3 |
| 116 | H | Cl | Et | OH | 5.4 | 667.3 | 669.3 |
| 117 | H | Cl | —CH(CH3)2 | OH | 5.7 | 681.3 | 683.3 |
| 118 | H | SMe | OEt | OH | 8.0 | 695.4 | |
| 119 | H | Me | O—CH(CH3)2 | OH | 7.0 | 677.3 | |
| 120 | OMe | Me | O—CH(CH3)2 | OH | 6.5 | 707.4 | |
| 121 | H | Cl | O—CH(CH3)2 | OH | 8.4 | 697.4 | 699.4 |
| 122 | H | Br | O—CH(CH3)2 | OH | 8.6 | 741.3 | 743.3 |
| 123 | H | F | O—CH(CH3)2 | OH | 7.7 | 681.4 | |
| 124 | H | SO2Me | OEt | OH | 6.8 | 727.3 | |
| 125 | H | Cl | SMe | OH | 8.0 | 685.3 | 687.3 |
| 126 | OMe | Br | OMe | OH | 7.5 | 743.3 | 745.3 |
| 127 | H | SMe | H | OH | 5.7 | 651.3 | |
| 128 | H | SOMe | H | OH | 5.3 | 667.2 | |
| 129 | H | SO2Me | H | OH | 5.6 | 683.2 | |
| 130 | H | Cl | SEt | OH | 8.1 | 699.3 | 701.3 |
| 131 | H | Cl | OCH2CH(CH3)2 | OH | 8.5 | 711.3 | 713.3 |
| 132 | H | Cl | OCH2CH2CH3 | OH | 8.1 | 697.3 | 699.3 |
| 133 | H | OMe | OEt | OH | 5.3 | 679.4 | |
| 134 | H | —C≡CH | OEt | OH | 7.1 | 673.4 | |
| 135 | OMe | Br | OEt | ![morpholine sulfonamide] | 8.1 | 905.3 | 907.3 |
| 136 | OMe | Br | OEt | ![methyl sulfonamide] | 7.9 | 834.2 | 836.2 |
| 137 | H | Cl | SCH2CH2CH3 | OH | 8.3 | 713.3 | 715.3 |
| 138 | H | Cl | SCH(CH3)2 | OH | 8.3 | 713.3 | 715.3 |
| 139 | H | Cl | OCH2C(CH3)3 | OH | 8.5 | 725.3 | 727.3 |
| 140 | H | Cl | OCH2CH2CF3 | OH | 8.0 | 751.3 | 753.3 |
| 141 | H | Cl | ![cyclopentyloxy] | OH | 8.4 | 723.3 | 721.3 |

TABLE 1-continued

| Cpd | R²² | R²¹ | R²⁰ | R¹ | $t_R$ | (MH)⁺ | (MH + 2)⁺ |
|---|---|---|---|---|---|---|---|
| 142 | H | Cl | —O—CH₂C≡CH (propargyloxy) | OH | 7.6 | 693.2 | 695.2 |
| 143 | H | Cl | —O—CH₂CH=CH₂ (allyloxy) | OH | 7.9 | 695.2 | 697.2 |
| 144 | H | Cl | —O—CH₂CH₂N(CH₃)₂ | OH | 5.7 | 726.3 | 728.3 |
| 145 | H | Cl | —C≡CH | OH | 6.0 | 663.2 | 665.2 |
| 146 | OMe | Br | —OCH₂C≡CH | OH | 7.4 | 767.2 | 769.2 |
| 147 | OMe | Br | —OCH₂CH=CH₂ | OH | 7.6 | 769.2 | 771.2 |
| 148 | H | Cl | —O—CH₂CH₂-(2-pyridyl) | OH | 5.9 | 760.3 | |
| 149 | OMe | CH₃ | —OCH₂PK CH=CH2 | OH | 6.6 | 705.3 | 707.3 |
| 150 | OMe | CH₃ | —OCH₂C≡CH | OH | 7.2 | 703.3 | 705.3 |
| 151 | OMe | Cl | —OEt | OH | 6.9 | 713.3 | 715.3 |
| 152 | OMe | Cl | —O—CH(CH₃)₂ | OH | 7.2 | 727.3 | |
| 153 | OMe | Cl | —OMe | OH | 6.7 | 699.3 | 701.3 |
| 154 | OMe | Cl | —OCH₂CH=CH₂ | OH | 7.4 | 725.3 | |
| 155 | OMe | Cl | —OCH₂C≡CH | OH | 7.3 | 723.3 | 725.3 |
| 156 | OMe | Br | —OCH₂C≡CCH₃ | OH | 7.6 | 781.2 | 783.2 |
| 157 | H | Cl | —O—CH₂CH₂-(1-imidazolyl) | OH | 5.8 | 749.2 | |
| 158 | H | Cl | —O—CH₂CH₂OMe | OH | 7.3 | 713.3 | 715.3 |
| 159 | H | Cl | —OCH=CH₂ | OH | 7.6 | 681.3 | 683.3 |
| 160 | OMe | Br | —O—CH(CH₃)₂ | OH | 7.5 | 771.2 | 773.2 |
| 161 | H | —SEt | —OEt | OH | 7.0 | 709.3 | |
| 162 | H | —SO₂Et | —OEt | OH | 5.9 | 741.3 | |

TABLE 1-continued

| Cpd | R²² | R²¹ | R²⁰ | R¹ | $t_R$ | (MH)⁺ | (MH + 2)⁺ |
|---|---|---|---|---|---|---|---|
| 163 | H | cyclopropylmethyl-S- | —OEt | OH | 7.1 | 735.2 | |
| 164 | H | Cl | —OCH₂CH₂N(CH₃)₂ | —NH-SO₂-phenyl | 6.8 | 865.1 | |
| 165 | H | Cl | —SCH₂CH₂CH₃ | —NH-SO₂-cyclopropyl | 9.5 | 816.3 | |
| 166 | H | SEt | —OEt | —NH-SO₂-N(CH₃)₂ | 7.2 | 815.3 | |

TABLE 2

| Cpd | R³ | R²² | R²¹ | R²⁰ | R¹ | $t_R$ | (MH)⁺/ (MH + 2)⁺ |
|---|---|---|---|---|---|---|---|
| 201 | Et | H | F | OEt | OH | 5.8 | 627.4 |
| 202 | F-CH₂CH₂-C(CH₃)- | H | F | OEt | OH | 5.6 | 645.4 |
| 203 | —CH₂CH₂CH₃ | H | F | OEt | OH | 6.3 | 641.4 |
| 204 | CF₃-CH₂CH₂-C(CH₃)- | H | F | OEt | OH | 6.5 | 695.4 |
| 205 | tetrahydrofuran-3-yl | H | F | OEt | OH | 5.2 | 669.4 |
| 206 | F-CH₂CH₂-C(CH₃)- | H | Cl | OEt | OH | 6.5 | 661.4/ 663.4 |
| 207 | —CH₂CH₂CH₃ | H | Cl | OEt | OH | 6.9 | 711.4/ 713.4 |
| 208 | CF₃-CH₂CH₂-C(CH₃)- | H | Cl | OEt | OH | 6.9 | 685.4/ 687.4 |
| 209 | tetrahydrofuran-3-yl | H | Cl | OEt | OH | 6.1 | 687.4 |
| 210 | Et | H | Me | OEt | OH | 5.2 | 623.4 |
| 211 | F-CH₂CH₂-C(CH₃)- | H | Me | OEt | OH | 4.9 | 641.4 |
| 212 | —CH₂CH₂CH₃ | H | Me | OEt | OH | 5.6 | 637.5 |
| 213 | CF₃-CH₂CH₂-C(CH₃)- | H | Me | OEt | OH | 5.8 | 691.4 |
| 214 | tetrahydrofuran-3-yl | H | Me | OEt | OH | 4.6 | 665.5 |
| 215 | F-CH₂CH₂CH₂-C(CH₃)- | H | Cl | OEt | OH | 6.6 | 675.3/ 677.3 |

TABLE 2-continued

| Cpd | R³ | R²² | R²¹ | R²⁰ | R¹ | $t_R$ | (MH)⁺/(MH + 2)⁺ |
|---|---|---|---|---|---|---|---|
| 216 | F-(CH)-CH₃ | H | Me | OEt | OH | 5.0 | 665.4 |
| 217 | F-(CH)-CH₃ | H | Me | OEt | -NH-SO₂-N(CH₃)₂ | 5.2 | 761.3 |

TABLE 3

| Cmp | R²² | R²¹ | R²⁰ | R¹ | $t_R$ | (MH)⁺ | (MH + 2)⁺ |
|---|---|---|---|---|---|---|---|
| 301 | OMe | Br | OEt | OH | 7.6 | 759.2 | 761.2 |
| 302 | H | Br | OEt | OH | 8.1 | 729.2 | 731.2 |
| 303 | H | Cl | OEt | OH | 7.9 | 685.3 | 687.3 |
| 304 | H | F | OEt | OH | 7.3 | 669.3 | |
| 305 | OMe | Me | OEt | OH | 6.4 | 695.4 | |
| 306 | H | Me | OEt | OH | 6.9 | 665.3 | |
| 307 | H | F | OMe | OH | 7.2 | 655.3 | |
| 308 | OMe | Me | OMe | OH | 6.2 | 681.3 | |
| 309 | H | Cl | SEt | OH | 8.4 | 701.3 | 703.3 |
| 310 | H | CH₃ | —OEt | -NH-SO₂-Ph | 8.5 | 804.4 | |

TABLE 3-continued
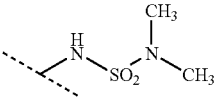
| Cmp | $R^{22}$ | $R^{21}$ | $R^{20}$ | $R^1$ | $t_R$ | $(MH)^+$ | $(MH+2)^+$ |
|---|---|---|---|---|---|---|---|
| 311 | OMe | $CH_3$ | —OEt | (N(H)SO2N(CH3)2) | 5.8 | 801.4 | |
TABLE 4
| Cpd | $R^{22}$ | $R^{21}$ | $R^{23}$ | $t_R$ | $(MH)^+$ | $(MH+2)^+$ |
|---|---|---|---|---|---|---|
| 401 | OMe | Br | H | 6.4 | 729.2 | 731.2 |
| 402 | OMe | Br | Me | 6.8 | 743.2 | 745.2 |
| 403 | OMe | Br | Et | 6.9 | 757.3 | 759.3 |
| 404 | OMe | Cl | Me | 6.3 | 699.3 | 701.3 |
| 405 | OMe | Cl | —$CH_2CHCH_2$ | 6.6 | 725.3 | 727.3 |
| 406 | OMe | $CH_3$ | H | 5.9 | 665.3 | 667.3 |
TABLE 5
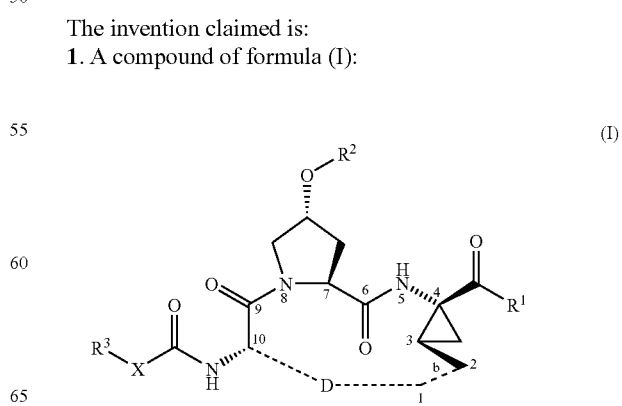
| Cpd | $R^{24}$ | $t_R$ | $(MH)^+$ |
|---|---|---|---|
| 501 | H | 5.6 | 655.3 |
| 502 | $CH_3$ | 6.2 | 669.3 |
The invention claimed is:
1. A compound of formula (I):
(I)

wherein R¹ is NHSO₂R¹¹ wherein R¹¹ is (C₁₋₆)alkyl, (C₂₋₆)alkenyl, (C₃₋₇)cycloalkyl, (C₃₋₇)cycloalkyl-(C₁₋₆)alkyl-, aryl, Het, aryl-(C₁₋₄)alkyl-, or Het-(C₁₋₄)alkyl-;

a) said (C₁₋₆)alkyl, (C₂₋₆)alkenyl, aryl, Het, (C₃₋₇)cycloalkyl-(C₁₋₆)alkyl-, aryl-(C₁₋₄)alkyl-, and Het-(C₁₋₄)alkyl- optionally being substituted with one, two or three substituents each independently selected from halogen, hydroxy, cyano, nitro, (C₁₋₆)alkyl, (C₁₋₆)haloalkyl, —O—(C₁₋₆)alkyl, —O—(C₁₋₆)haloalkyl, —O-aryl, —C(=O)—(C₁₋₆)alkyl, —C(=O)—NH₂, —C(=O)—NH(C₁₋₄)alkyl, —C(=O)—N((C₁₋₄)alkyl)₂, —NH₂, —NH(C₁₋₄)alkyl and —N((C₁₋₄)alkyl)₂; and b) said (C₃₋₇)cycloalkyl being optionally substituted with one or more substituents each independently selected from nitro, halogen, hydroxy, cyano, —O—(C₁₋₆)alkyl, (C₂₋₄)alkenyl, —O—(C₁₋₆)haloalkyl, —NH₂, —NH(C₁₋₄)alkyl, —N((C₁₋₄)alkyl)₂, tri(C₁₋₆)alkylsilyl, R⁴¹, —C(=O)—R⁴¹, —C(=O)OR⁴¹, —C(=O)N(R⁴²)R⁴¹, —SO₂R⁴¹, and —OC(=O)—R⁴¹;

wherein R⁴¹ in each case is independently selected from:

i) H, (C₃₋₇)cycloalkyl, (C₄₋₇)cycloalkenyl, Het, or aryl-(C₁₋₄)alkyl-O—;

ii) aryl or aryloxy, each of which being optionally substituted with (C₁₋₆)alkyl; and iii) (C₁₋₈)alkyl optionally substituted with one or more substituents each independently selected from —O—(C₁₋₆)alkyl, hydroxy, halogen, (C₂₋₁₀)alkenyl, (C₂₋₁₀)alkynyl, (C₃₋₇)cycloalkyl, (C₄₋₇)cycloalkenyl, aryl, Het, aryloxy, and aryl-(C₁₋₄)alkyl-O—, wherein each of said aryl and aryloxy is optionally substituted with (C₁₋₆)alkyl; and R⁴² is selected from H and (C₁₋₆)alkyl; or R¹¹ is —N(R¹¹ᵃ)(R¹¹ᵇ), wherein R¹¹ᵃ and R¹¹ᵇ are each independently selected from H, (C₁₋₆)alkyl, (C₃₋₇)cycloalkyl, (C₃₋₇)cycloalkyl-(C₁₋₆)alkyl-, aryl, aryl-(C₁₋₆)alkyl-, Het and Het-(C₁₋₄)alkyl-; wherein said (C₁₋₆)alkyl, (C₃₋₇)cycloalkyl, (C₃₋₇)cycloalkyl-(C₁₋₆)alkyl-, aryl, aryl-(C₁₋₆)alkyl-, Het and Het-(C₁₋₄)alkyl- are each optionally substituted with one or more substituents each independently selected from halogen, (C₁₋₆)alkyl, hydroxy, cyano, nitro, (C₁₋₆)haloalkyl, —O—(C₁₋₆)alkyl, —O—(C₁₋₆)haloalkyl, —NH₂, —NH(C₁₋₄)alkyl, —N((C₁₋₄)alkyl)₂, —C(=O)—NH₂, —C(=O)—NH(C₁₋₄)alkyl, —C(=O)—N((C₁₋₄)alkyl)₂, —C(=O)—(C₁₋₆)alkyl, —COOH, and —COO(C₁₋₆)alkyl; or R¹¹ᵃ and R¹¹ᵇ are linked, together with the nitrogen to which they are bonded, to form a 3- to 7-membered monocyclic saturated or unsaturated heterocycle optionally fused to at least one other cycle to form a heteropolycycle, said heterocycle and heteropolycycle optionally containing from one to three further heteroatoms each independently selected from N, S and O, and being optionally substituted with one or more substituents each independently selected from halogen, (C₁₋₆)alkyl, hydroxy, cyano, nitro, (C₁₋₆)haloalkyl, —O—(C₁₋₆)alkyl, —O—(C₁₋₆)haloalkyl, —NH₂, —NH(C₁₋₄)alkyl, —N((C₁₋₄)alkyl)₂, —C(=O)—NH₂, —C(=O)—NH(C₁₋₄)alkyl, —C(=O)—N((C₁₋₄)alkyl)₂, —C(=O)—(C₁₋₆)alkyl, —COOH, and —COO(C₁₋₆)alkyl;

R² is a group of formula:

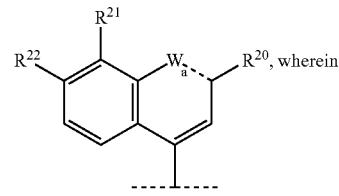

R²⁰ is H, OH, halogen, or Y¹—R²⁰ᵃ wherein Y¹ is a bond, O, S, or NR²⁰ᵇ and wherein:

R²⁰ᵃ is selected from the group consisting of: (C₁₋₈)alkyl, (C₁₋₆)alkyl-C≡N, (C₂₋₈)alkenyl, (C₂₋₈)alkynyl and (C₃₋₇)cycloalkyl, each of said alkyl, alkenyl, alkynyl and cycloalkyl being optionally substituted with one, two or three substituents, each independently selected from:

halogen, (C₁₋₆)alkyl optionally substituted with —O—(C₁₋₆)alkyl or —O—(C₃₋₆)cycloalkyl, (C₃₋₇)cycloalkyl, —O—(C₁₋₆)alkyl, Het, —O—(C₃₋₆)cycloalkyl, —NH₂, —NH(C₁₋₄)alkyl and —N((C₁₋₄)alkyl)₂; and R²⁰ᵇ is H, (C₁₋₆)alkyl or (C₃₋₆)cycloalkyl;

and W is N; and the dotted line "a" is a double bond; or R²⁰ is oxo, and W is NR²³ wherein R²³ is H, (C₁₋₆)alkyl, (C₂₋₆)alkenyl or (C₂₋₆)alkynyl; and the dotted line "a" is a single bond;

R²¹ is halogen or Y²—R²¹ᵃ, wherein Y² is a bond, O, S, SO or SO₂, and R²¹ᵃ is (C₁₋₆)alkyl, (C₂₋₆)alkenyl, (C₂₋₆)alkynyl, (C₃₋₇)cycloalkyl or (C₃₋₇)cycloalkyl-(C₁₋₆)alkyl-;

R²² is H, —OH, —O—(C₁₋₄)alkyl, —NH₂, —NH(C₁₋₄)alkyl or —N((C₁₋₄)alkyl)₂;

or R² is a group of formula:

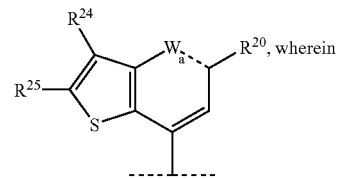

R²⁰, W and the dotted line "a" are as defined above;
R²⁴ is H or R²¹ as defined above; and
R²⁵ is H or (C₁₋₆)alkyl;

X is O or NH;

R³ is (C₁₋₁₀)alkyl, (C₃₋₇)cycloalkyl or (C₃₋₇)cycloalkyl-(C₁₋₄)alkyl-, a) wherein the cycloalkyl and cycloalkyl-alkyl- may be mono-, di- or tri-substituted with (C₁₋₃)alkyl;

b) wherein the alkyl, cycloalkyl and cycloalkyl-alkyl- may be mono- or di-substituted with substituents each independently selected from hydroxy and O—(C₁₋₆)alkyl;

c) wherein each alkyl group may be mono-, di- or tri-substituted with halogen; and d) wherein in each cycloalkyl group being 5-, 6- or 7-membered, one or two —CH₂-groups not being directly linked to each other may be replaced by —O— such that the O-atom is linked to the group X via at least two C-atoms;

D is a 3 to 8 atom saturated or unsaturated alkylene chain; and the dotted line "b" is a single bond or a double bond;
wherein Het as used herein is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a pharmaceutically acceptable salt or ester thereof;
with the proviso that
when $R^2$ is a group of formula

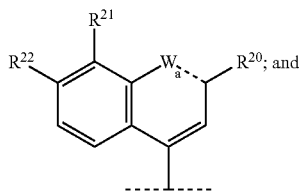

W is N; and the dotted line "a" is a double bond; and
$R^{20}$ is H, halogen, or $Y^1$—$R^{20a}$, wherein $Y^1$ is O and $R^{20a}$ is $(C_{1-6})$alkyl or $(C_{3-6})$cycloalkyl; or $Y^1$ is a bond and $R^{20a}$ is $(C_{1-6})$alkyl; and
$R^{21}$ is halogen or $Y^2$—$R^{21a}$, wherein $Y^2$ is O and $R^{21a}$ is $(C_{1-6})$alkyl or $(C_{3-6})$cycloalkyl; and
$R^{22}$ is H; and
$R^3$ is $(C_{1-6})$alkyl optionally substituted with halo, or $R^3$ is —$(CH_2)_p$—$(C_{3-7})$cycloalkyl wherein p is 0-4, or $R^3$ is a tetrahydrofuran ring linked through the C3 or C4 position of the ring;
then $R^1$ is not $NHSO_2R^{11}$ wherein $R^{11}$ is $(C_{1-6})$alkyl or unsubstituted $(C_{3-7})$cycloalkyl.

2. The compound according to claim 1 wherein $R^2$ is a group of formula:

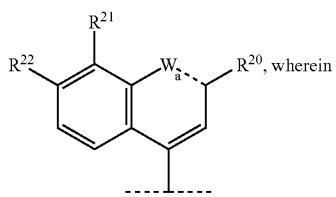

W, $R^{20}$, $R^{21}$, $R^{22}$ and the dotted line "a" are defined as in claim 1.

3. The compound according to claim 1 wherein W is N; the dotted line "a" is a double bond; and $R^{20}$ is H, OH, halogen, or $Y^1$—$R^{20a}$ wherein
$Y^1$ is a bond, O, S, or $NR^{20b}$;
$R^{20a}$ is selected from the group consisting of: $(C_{1-8})$alkyl, $(C_{2-8})$alkenyl, $(C_{2-8})$alkynyl and $(C_{3-7})$cycloalkyl, each of said alkyl, alkenyl, alkynyl and cycloalkyl being optionally substituted with one, two or three substituents, each independently selected from:
halogen, $(C_{1-6})$alkyl, $(C_{3-7})$cycloalkyl, Het, —O—$(C_{1-6})$alkyl, —O—$(C_{3-6})$cycloalkyl, —$NH_2$, —$NH(C_{1-4})$alkyl and —$N((C_{1-4})$alkyl$)_2$; and
$R^{20b}$ is H, $(C_{1-6})$alkyl or $(C_{3-6})$cycloalkyl;
wherein Het is defined as in claim 1.

4. The compound according to claim 2 wherein W is N; the dotted line "a" is a double bond; and $R^{20}$ is H, $(C_{1-6})$alkyl, OH, —O—$(C_{1-6})$alkyl, —S—$(C_{1-6})$alkyl, —$(CH_2)_{0-4}$—CH=$CH_2$, —$(CH_2)_{0-4}$—C≡CH, —O—$(CH_2)_{0-4}$—CH=$CH_2$, —O—$(CH_2)_{0-4}$—C≡CH, —O—$(CH_2)_{1-4}$-OMe; —O—$(CH_2)_{14}$—$N(Me)_2$; —O—$(CH_2)_{1-4}$-Het; —S—$(CH_2)_{0-4}$-CH=$CH_2$, —S—$(CH_2)_{0-4}$—C≡CH, —S—$(CH_2)_{1-4}$-OMe; —S—$(CH_2)_{1-4}$-$N(Me)_2$, —S—$(CH_2)_{1-4}$-Het; $(C_{3-6})$cycloalkyl, —O—$(C_{3-6})$cycloalkyl, O—$(C_{1-6})$alkyl-$(C_{3-6})$cycloalkyl, —S—$(C_{3-6})$cycloalkyl, or —S—$(C_{1-6})$alkyl-$(C_{3-6})$cycloalkyl; wherein Het is 5- or 6-membered monocyclic heteroaryl containing from one to three heteroatoms each independently selected from N, O and S;
each of said $(C_{1-6})$alkyl, —O—$(C_{1-6})$alkyl, —S—$(C_{1-6})$alkyl, —$(CH_2)_{0-4}$-CH=$CH_2$, —$(CH_2)_{0-4}$—C≡CH, —O—$(CH_2)_{0-4}$-CH=$CH_2$, —O—$(CH_2)_{0-4}$—C≡CH, —S—$(CH_2)_{0-4}$—CH=$CH_2$, —S—$(CH_2)_{0-4}$—C≡CH, $(C_{3-6})$cycloalkyl, —O—$(C_{3-6})$cycloalkyl, and —S—$(C_{3-6})$cycloalkyl being optionally substituted with one, two or three substituents, each independently selected from $(C_{1-4})$alkyl, —O—$(C_{1-4})$alkyl, and halo;
or $R^{20}$ is $NR^{20a}R^{20b}$ wherein $R^{20a}$ is $(C_{1-4})$alkyl, and $R^{20b}$ is H, $(C_{1-4})$alkyl or $(C_{3-5})$cycloalkyl.

5. The compound according to claim 4 wherein $R^{20}$ is H, methyl, ethyl, propyl, 1-methylethyl, butyl, 2-methylpropyl, cyclopropyl, cyclobutyl, cyclopentyl, cyclohexyl, —CH=$CH_2$, —C≡CH, O-methyl, O-ethyl, O-propyl, O—$CH(CH_3)_2$, O-cyclopropyl, O-cyclobutyl, O-cyclopentyl, O-cyclohexyl, O—$CH_2CH_2CF_3$, —O—CH=$CH_2$, —O—$CH_2$—CH=$CH_2$, O—C≡CH, —O—$CH_2$—C≡CH, —O—$CH_2$—C≡$CCH_3$, —O—$CH_2$—$CH_2$—OMe, —O—$CH_2$—$CH_2$—$N(Me)_2$, S-methyl, S-ethyl, S-propyl, S—$CH(CH_3)_2$, S-cyclopropyl, S-cyclobutyl, S-cyclopentyl, S-cyclohexyl, —S—CH=$CH_2$, —S—$CH_2$—CH=$CH_2$, S—C≡CH, —S—$CH_2$—C≡CH, —S—$CH_2$—$CH_2$-OMe, —S—$CH_2$—$CH_2$—$N(Me)_2$,

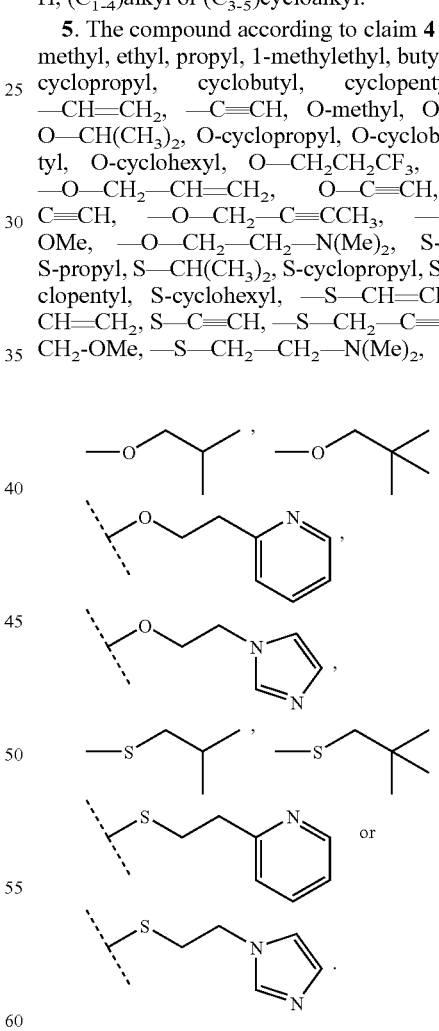

6. The compound according to claim 2 wherein $R^{21}$ is selected from: fluorine, chlorine, bromine, —$CH_3$, —$CH_2CH_3$, —$CH_2CH_2CH_3$, —$OCH_3$, —$OCH_2CH_3$, —$OCH_2CH_2CH_3$, —$SCH_3$, —$SCH_2CH_3$, —$SCH_2CH_2CH_3$, —(SO)$CH_3$, —(SO)$CH_2CH_3$, —(SO)$CH_2CH_2CH_3$, —($SO_2$)$CH_3$, —($SO_2$)$CH_2CH_3$, —($SO_2$)$CH_2CH_2CH_3$,

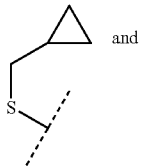

and

—C≡CH.

7. The compound according to claim 2 wherein $R^{22}$ is selected from: H, —OH, —OCH$_3$, —OCH$_2$CH$_3$, —OCH$_2$CH$_2$CH$_3$, —NHCH$_3$, —N(CH$_3$)$_2$, —N(CH$_3$)CH$_2$CH$_3$ and —N(CH$_3$)CH$_2$CH$_2$CH$_3$.

8. The compound according to claim 7 wherein $R^{22}$ is H or —OCH$_3$.

9. The compound according to claim 1 wherein X is O.

10. The compound according to claim 1 wherein $R^3$ is selected from (C$_{2-8}$)alkyl, (C$_{3-7}$)cycloalkyl and (C$_{3-7}$)cycloalkyl-(C$_{1-3}$)alkyl-,
   a) wherein said cycloalkyl and cycloalkyl-alkyl- may be mono-, di- or tri-substituted with (C$_{1-3}$)alkyl; and
   b) wherein said alkyl, cycloalkyl and cycloalkyl-alkyl- may be mono- or di-substituted with substituents each independently selected from hydroxy and O—(C$_{1-4}$)alkyl; and
   c) wherein each of said alkyl groups may be mono-, di- or tri-substituted with fluorine or mono-substituted with chlorine or bromine; and
   d) wherein in each of said cycloalkyl groups being 5-, 6- or 7-membered, one or two —CH$_2$-groups not being directly linked to each other may be replaced by —O— such that the O-atom is linked to the group X via at least two C-atoms.

11. The compound according to claim 10 wherein $R^3$ is selected from cyclopropyl, cyclobutyl, cyclopentyl, cyclohexyl, and a group selected from:

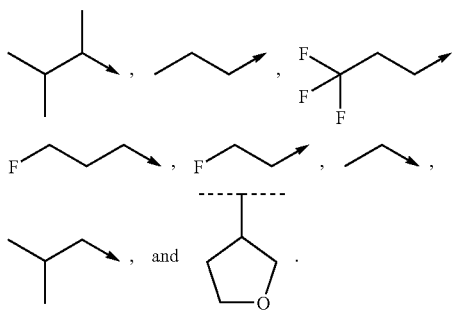

12. The compound according to claim 1 wherein linker D is a 5 carbon atom chain.

13. The compound according to claim 1 wherein the dotted line "b" is a single bond or a double bond in the Z (cis) configuration.

14. The compound according to claim 1 of formula (Ia):

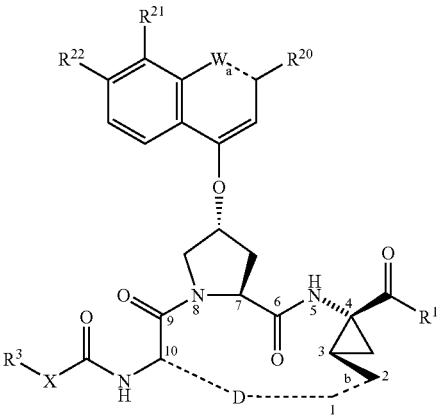

(Ia)

wherein $R^1$ is hydroxy or NHSO$_2$R$^{11}$ wherein $R^{11}$ is (C$_{1-6}$)alkyl, (C$_{3-7}$)cycloalkyl, (C$_{6 \text{ or } 10}$)aryl, Het, (C$_{3-7}$)cycloalkyl-(C$_{1-6}$)alkyl-, (C$_{6 \text{ or } 10}$)aryl-(C$_{1-4}$)alkyl- or Het-(C$_{1-4}$)alkyl-, all of which being optionally mono-, di- or tri-substituted with substituents selected from:
   halogen, hydroxy, cyano, nitro, (C$_{1-6}$)alkyl, (C$_{1-6}$)haloalkyl, O—(C$_{1-6}$)alkyl, —O—(C$_{1-4}$)haloalkyl, —C(O)—(C$_{1-6}$)alkyl, —C(O)—NH$_2$, —C(O)—NH(C$_{1-4}$)alkyl, —C(O)—N((C$_{1-4}$)alkyl)$_2$, —NH$_2$, —NH(C$_{1-4}$)alkyl and —N((C$_{1-4}$)alkyl)$_2$;
   or $R^{11}$ is —NR$^{11a}$R$^{11b}$ wherein $R^{11a}$ is H or (C$_{1-6}$)alkyl, and $R^{11b}$ is H, (C$_{1-6}$)alkyl, (C$_{3-6}$)cycloalkyl, (C$_{6 \text{ or } 10}$)aryl, Het, (C$_{3-6}$)cycloalkyl-(C$_{1-4}$)alkyl-, (C$_{6 \text{ or } 10}$)aryl-(C$_{1-4}$)alkyl- or Het-(C$_{1-4}$)alkyl-, or $R^{11a}$ and $R^{11b}$ are linked to each other to form a 3 to 7-membered nitrogen-containing ring optionally containing one or two further heteroatoms selected from: O, S or N, all of said $R^{11a}$ and $R^{11b}$ being optionally substituted with:
   halogen, hydroxy, cyano, nitro, (C$_{1-6}$)alkyl, (C$_{1-6}$)haloalkyl, O—(C$_{1-6}$)alkyl, —O—(C$_{1-4}$)haloalkyl, —C(O)—(C$_{1-6}$)alkyl, —C(O)—NH$_2$, —C(O)—NH(C$_{1-4}$)alkyl, —C(O)—N((C$_{1-4}$)alkyl)$_2$, —NH$_2$, —NH(C$_{1-4}$)alkyl and —N((C$_{1-4}$)alkyl)$_2$;

$R^{20}$ is H, OH, halogen, or $Y^1$—R$^{20a}$ wherein $Y^1$ is a bond, O, S, or NR$^{20b}$ wherein:
   $R^{20a}$ is selected from the group consisting of: (C$_{1-8}$)alkyl, (C$_{1-6}$)alkyl-C≡N, (C$_{2-8}$)alkenyl, (C$_{2-8}$)alkynyl, all of said alkyl, alkenyl and alkynyl being optionally mono- or di-substituted with:
      halogen, (C$_{1-6}$)alkyl, —O—(C$_{1-6}$)alkyl, (C$_{1-4}$)alkyl-O—(C$_{1-6}$)alkyl, —O—(C$_{3-6}$)cycloalkyl, (C$_{1-4}$)alkyl-O—(C$_{3-6}$)cycloalkyl, amino, (C$_{1-6}$)alkylamino, or di((C$_{1-6}$)alkyl)amino; and
   $R^{20b}$ is H, (C$_{1-6}$)alkyl or (C$_{3-6}$)cycloalkyl;
and W is N; and the dotted line "a" is a double bond; or
$R^{20}$ is oxo, and W is NR$^{23}$ wherein $R^{23}$ is H, (C$_{1-6}$)alkyl, (C$_{2-6}$)alkenyl, (C$_{2-6}$)alkynyl; and the dotted line "a" is a single bond;
$R^{21}$ is halogen, (C$_{1-6}$)alkyl, (C$_{2-6}$)alkenyl, (C$_{2-6}$)alkynyl, —O—(C$_{1-6}$)alkyl, —O—(C$_{2-6}$)alkenyl, —O—(C$_{2-6}$)alkynyl, —S—(C$_{1-6}$)alkyl, —S—(C$_{2-6}$)alkenyl, and —S—(C$_{2-6}$)alkynyl, wherein the sulfur is in any oxidized state;
$R^{22}$ is H, —OH, —O—(C$_{1-4}$)alkyl, —NH$_2$, —NH(C$_{1-4}$)alkyl or —N((C$_{1-4}$)alkyl)$_2$;
X is O or NH;

$R^3$ is $(C_{1-10})$alkyl, $(C_{3-7})$cycloalkyl, $(C_{3-7})$cycloalkyl-$(C_{1-4})$alkyl-,
  a) wherein the cycloalkyl and cycloalkyl-alkyl- may be mono-, di- or tri-substituted with $(C_{1-3})$alkyl;
  b) wherein the alkyl, cycloalkyl and cycloalkyl-alkyl- may be mono- or di-substituted with substituents selected from hydroxy and O—$(C_{1-6})$alkyl;
  c) wherein all the alkyl groups may be mono-, di- or tri-substituted with halogen; and
  d) wherein in the cycloalkyl groups, being 5-, 6- or 7-membered, one or two —$CH_2$-groups not being directly linked to each other may be replaced by —O—;

D is a 3 to 8 atom saturated or unsaturated alkylene chain; and the dotted line "b" is a single bond or a double bond;

or a pharmaceutically acceptable salt or ester thereof.

15. The compound according to claim 1 wherein $R^1$ is hydroxy or $NHSO_2R^{11}$; wherein $R^{11}$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
  a) each of which optionally being mono-, di- or tri-substituted with substituents each independently selected from fluorine and methyl; and
  b) each of which optionally being mono- or disubstituted with substituents each independently selected from hydroxy, trifluoromethyl, methoxy, phenoxy and trifluoromethoxy; and
  c) each of which optionally being monosubstituted with a substituent selected from chlorine, bromine, cyano, nitro, —CO—$NH_2$, —CO—$NHCH_3$, —CO—N$(CH_3)_2$, —$NH_2$, —$NH(CH_3)$ and —$N(CH_3)_2$;

wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl,

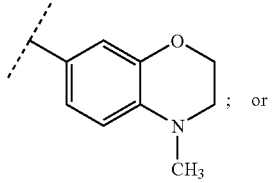

and ; or $R^{11}$ is selected from cyclopropyl, cyclobutyl, cyclopentyl and cyclohexyl;
  a) each of which optionally being mono-, di- or tri-substituted with fluorine; and
  b) each of which optionally being mono- or disubstituted with substituents selected from hydroxy, methoxy and trifluoromethoxy; and
  c) each of which optionally being monosubstituted with a substituent selected from chlorine, bromine, cyano, nitro, —CO—$NH_2$, —CO—$NHCH_3$, —CO—N$(CH_3)_2$, —$NH_2$, —$NH(CH_3)$ and —$N(CH_3)_2$; and
  d) each of which being optionally substituted with one or more $(C_{1-8})$alkyl, wherein each $(C_{1-8})$alkyl is independently optionally substituted with one or more substituents each independently selected from —O—$(C_{1-6})$alkyl, hydroxy, halogen, $(C_{2-10})$alkenyl, $(C_{2-10})$alkynyl, $(C_{3-7})$cycloalkyl, $(C_{4-7})$cycloalkenyl, aryl, aryloxy, and aryl-$(C_{1-4})$alkyl-O—, wherein each of said aryl and aryloxy is optionally substituted with $(C_{1-6})$alkyl; or $R^{11}$ is —$N(R^{11a})(R^{11b})$, wherein
  $R^{11a}$ and $R^{11b}$ are each independently selected from H, methyl, ethyl, propyl, 1-methylethyl, cyclopropyl, cyclobutyl, cyclopentyl, cyclohexyl, phenyl and phenylmethyl; wherein said methyl, ethyl, propyl, 1-methylethyl, cyclopropyl, cyclobutyl, cyclopentyl, cyclohexyl, phenyl and phenylmethyl are optionally substituted with one or more substituents each independently selected from halogen, $(C_{1-4})$alkyl, hydroxy, cyano, O—$(C_{1-4})$alkyl, —$NH_2$, —$NH(C_{1-4})$alkyl, —$N((C_{1-4})$alkyl$)_2$, —CO—$NH_2$, —CO—NH$(C_{1-4})$alkyl, —CO—$N((C_{1-4})$alkyl$)_2$, —COOH, and —COO$(C_{1-4})$alkyl; or $R^{11a}$ and $R^{11b}$ are linked, together with the nitrogen to which they are bonded, to form a 3-4-, 5- or 6-membered monocyclic saturated or unsaturated heterocycle, optionally containing from one to three further heteroatoms each independently selected from N, S and O, and optionally substituted with one, two or three substituents each independently selected from halogen, $(C_{1-4})$alkyl, hydroxy, cyano, O—$(C_{1-4})$alkyl, —$NH_2$, —$NH(C_{1-4})$alkyl, —$N((C_{1-4})$alkyl$)_2$, —CO—$NH_2$, —CO—NH$(C_{1-4})$alkyl, —CO—$N((C_{1-4})$alkyl$)_2$, —COOH, and —COO$(C_{1-4})$alkyl; and $R^2$ is a group of formula

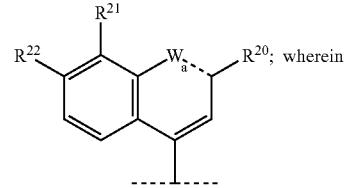

$R^{20}$ is oxo, W is $NR^{23}$ wherein $R^{23}$ is Me, Et, —$CH_2CH$=$CH_2$ or H and the dotted line "a" is a single bond; or W is N, the dotted line "a" is a double bond; and $R^{20}$ is H, OH, halogen, or $Y^1$—$R^{20a}$ wherein
  $Y^1$ is a bond, O, S, or $NR^{20b}$;
  $R^{20a}$ is selected from the group consisting of: $(C_{1-8})$alkyl, $(C_{2-8})$alkenyl, $(C_{2-8})$alkynyl and $(C_{3-7})$cycloalkyl, each of said alkyl, alkenyl, alkynyl and cycloalkyl being optionally substituted with one, two or three substituents, each independently selected from:
    halogen, $(C_{1-6})$alkyl, $(C_{3-7})$cycloalkyl, Het, —O—$(C_{1-6})$alkyl, —O—$(C_{3-6})$cycloalkyl, —$NH_2$, —$NH(C_{1-4})$alkyl and —$N((C_{1-4})$alkyl$)_2$;
    wherein Het is defined as in claim 1; and
  $R^{20b}$ is H, $(C_{1-6})$alkyl or $(C_{3-6})$cycloalkyl; and $R^{21}$ is selected from: fluorine, chlorine, bromine, —$CH_3$, —$CH_2CH_3$, —$CH_2CH_2CH_3$, —$OCH_3$, —$OCH_2CH_3$, —$OCH_2CH_2CH_3$, —$SCH_3$, —$SCH_2CH_3$, —$SCH_2CH_2CH_3$, —(SO)$CH_3$, —(SO)$CH_2CH_3$, —(SO)$CH_2CH_2CH_3$, —(SO$_2$)$CH_3$, —(SO$_2$)$CH_2CH_3$, —(SO$_2$)$CH_2CH_2CH_3$,

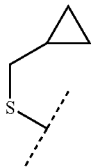

and —C≡CH; and $R^{22}$ is selected from: H, —OH, —OCH$_3$, —OCH$_2$CH$_3$, —OCH$_2$CH$_2$CH$_3$, —NHCH$_3$, —N(CH$_3$)$_2$, —N(CH$_3$)CH$_2$CH$_3$ and —N(CH$_3$)CH$_2$CH$_2$CH$_3$;

or $R^2$ is a group of formula

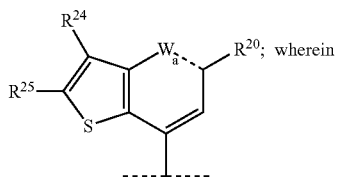

W is N; the dotted line "a" is a double bond; and $R^{20}$ is H, OH, halogen, or $Y^1$—$R^{20a}$ wherein $Y^1$ is a bond, O, S, or $NR^{20b}$;

$R^{20a}$ is selected from the group consisting of: $(C_{1-8})$alkyl, $(C_{2-8})$alkenyl, $(C_{2-8})$alkynyl and $(C_{3-7})$cycloalkyl, each of said alkyl, alkenyl, alkynyl and cycloalkyl being optionally substituted with one, two or three substituents, each independently selected from:

halogen, $(C_{1-6})$alkyl, $(C_{3-7})$cycloalkyl, Het, —O—$(C_{1-6})$alkyl, —O—$(C_{3-6})$cycloalkyl, —NH$_2$, —NH$(C_{1-4})$alkyl and —N$((C_{1-4})$alkyl$)_2$; wherein Het is defined as in claim 1; and $R^{20b}$ is H, $(C_{1-6})$alkyl or $(C_{3-6})$cycloalkyl; and $R^{24}$ is H or $(C_{1-6})$alkyl; and $R^{25}$ is H; and X is O or NH; and $R^3$ is selected from $(C_{2-8})$alkyl, $(C_{3-7})$cycloalkyl and $(C_{3-7})$cycloalkyl-$(C_{1-3})$alkyl-, a) wherein said cycloalkyl and cycloalkyl-alkyl- may be mono-, di- or tri-substituted with $(C_{1-3})$alkyl; and b) wherein said alkyl, cycloalkyl and cycloalkyl-alkyl- may be mono- or di-substituted with substituents each independently selected from hydroxy and O—$(C_{1-4})$alkyl; and c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O— such that the O-atom is linked to the group X via at least two C-atoms; and linker D is a 3 to 8 atom saturated or unsaturated alkylene chain; and the dotted line "b" is a single bond or a double bond.

16. The compound according to claim 1 wherein $R^1$ is hydroxy or NHSO$_2$R$_{11}$, wherein $R^{11}$ is selected from methyl, ethyl, 1-methylethyl, propyl, ethenyl, cyclopropyl, cyclobutyl, cyclopentyl, phenyl,

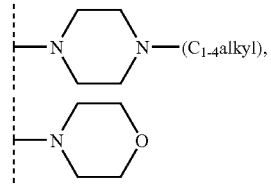

and —N(CH$_3$)$_2$; wherein said phenyl is optionally monosubstituted with halogen and wherein said cyclopropyl is optionally substituted at the 1-position with methyl, ethyl, propyl or butyl, each of said methyl, ethyl, propyl and butyl being optionally further substituted with phenyl, $(C_{3-6})$cycloalkyl, $(C_{2-6})$alkenyl or $(C_{1-4})$alkoxy; and $R^2$ is a group of formula

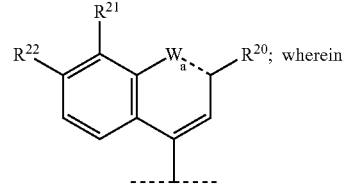

$R^{20}$ is oxo, W is $NR^{23}$ wherein $R^{23}$ is Me, Et, —CH$_2$CH=CH$_2$ or H and the dotted line "a" is a single bond; or W is N, the dotted line "a" is a double bond, and $R^{20}$ is H, $(C_{1-6})$alkyl, OH, —O—$(C_{1-6})$alkyl, —S—$(C_{1-6})$alkyl, —(CH$_2$)$_{0-4}$—CH=CH$_2$, —(CH$_2$)$_{0-4}$—C≡CH, —O—(CH$_2$)$_{0-4}$—CH=CH$_2$, —O—(CH$_2$)$_{0-4}$—C≡CH, —O—(CH$_2$)$_{1-4}$-OMe; —O—(CH$_2$)$_{1-4}$-N(Me)$_2$; —O—(CH$_2$)$_{1-4}$-Het; —S—(CH$_2$)$_{0-4}$—CH=CH$_2$, —S—(CH$_2$)$_{0-4}$—C≡CH, —S—(CH$_2$)$_{1-4}$-OMe; —S—(CH$_2$)$_{1-4}$—N(Me)$_2$, —S—(CH$_2$)$_{1-4}$-Het; $(C_{3-6})$cycloalkyl, —O—$(C_{3-6})$cycloalkyl, O—$(C_{1-6})$alkyl-$(C_{3-6})$cycloalkyl, —S—$(C_{3-6})$cycloalkyl, or —S—$(C_{1-6})$alkyl-$(C_{3-6})$cycloalkyl; wherein Het is 5- or 6-membered monocyclic heteroaryl containing from one to three heteroatoms each independently selected from N, O and S;

each of said $(C_{1-6})$alkyl, —O—$(C_{1-6})$alkyl, —S—$(C_{1-6})$alkyl, —(CH$_2$)$_{0-4}$—CH=CH$_2$, —(CH$_2$)$_{0-4}$—C≡CH, —O—(CH$_2$)$_{0-4}$—CH=CH$_2$, —O—(CH$_2$)$_{0-4}$—C≡CH, —S—(CH$_2$)$_{0-4}$—CH=CH$_2$, —S—(CH$_2$)$_{0-4}$—C≡CH, $(C_{3-6})$cycloalkyl, —O—$(C_{3-6})$cycloalkyl, and —S—$(C_{3-6})$cycloalkyl being optionally substituted with one, two or three substituents, each independently selected from $(C_{1-4})$alkyl, —O—$(C_{1-4})$alkyl, and halo;

or $R^{20}$ is $NR^{20a}R^{20b}$ wherein $R^{20a}$ is $(C_{1-4})$alkyl, and $R^{20b}$ is H, $(C_{1-4})$alkyl or $(C_{3-5})$cycloalkyl; and $R^{21}$ is selected from: fluorine, chlorine, bromine, —CH$_3$, —CH$_2$CH$_3$, —CH$_2$CH$_2$CH$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, —(SO)CH$_3$, —(SO)CH$_2$CH$_3$, —(SO)CH$_2$CH$_2$CH$_3$, —(SO$_2$)CH$_3$, —(SO$_2$)CH$_2$CH$_3$, —(SO$_2$)CH$_2$CH$_2$CH$_3$,

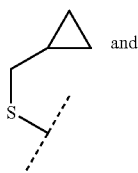
and and —C≡CH; and $R^{22}$ is selected from H, —OCH$_3$ and —N(CH$_3$)$_2$;

or $R^2$ is a group of formula

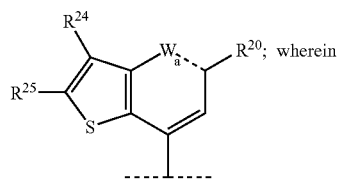

W is N; the dotted line "a" is a double bond;

$R^{20}$ is $Y^1$—$R^{20a}$, wherein $Y^1$ is O and $R^{20a}$ is (C$_{1-8}$)alkyl;

$R^{24}$ is H or (C$_{1-6}$)alkyl; and $R^{25}$ is H; and

X is O or NH; and $R^3$ is selected from cyclopropyl, cyclobutyl, cyclopentyl, cyclohexyl, and a group selected from:

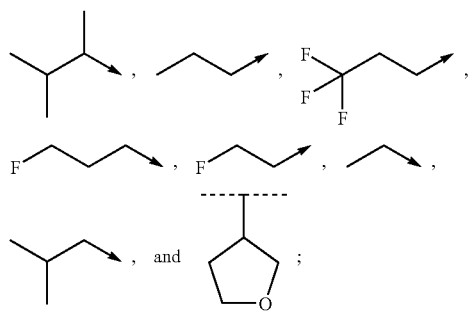

and linker D is a 3 to 8 atom saturated or unsaturated alkylene chain; and the dotted line "b" is a single bond or a double bond.

17. The compound according to claim 1 wherein $R^1$ is hydroxy or NHSO$_2$R$^{11}$, wherein $R^{11}$ is methyl, cyclopropyl, phenyl,

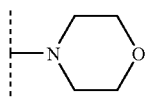

or —N(CH$_3$)$_2$; and $R^2$ is a group of formula

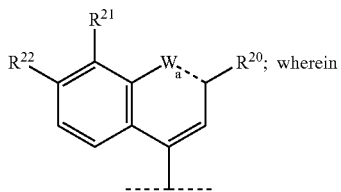

$R^{20}$ is oxo, W is NR$^{23}$ wherein $R^{23}$ is Me, Et, —CH$_2$CH=CH$_2$ or H and the dotted line "a" is a single bond; or W is N, the dotted line "a" is a double bond, and $R^{20}$ is H, methyl, ethyl, 1-methylethyl, —C≡CH, O-methyl, O-ethyl, O-propyl, O—CH(CH$_3$)$_2$, O-cyclopentyl, O—CH$_2$CH$_2$CF$_3$, —O—CH=CH$_2$, —O—CH$_2$—CH=CH$_2$, —O—CH$_2$—C≡CH, —O—CH$_2$—C≡CCH$_3$, —O—CH$_2$CH$_2$OMe, —O—CH$_2$CH$_2$N(Me)$_2$, S-methyl, S-ethyl, S-propyl, S—CH(CH$_3$)$_2$,

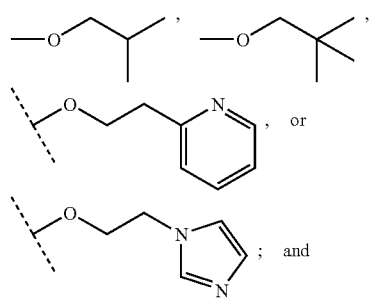

; and $R^{21}$ is selected from fluorine, chlorine, bromine, —CH$_3$, —OCH$_3$, —SCH$_3$, —SCH$_2$CH$_3$, (SO)CH$_3$, (SO$_2$)CH$_3$, —(SO$_2$)CH$_2$CH$_3$,

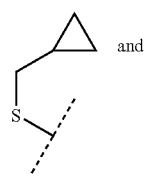
and

—C≡CH; and or $R^2$ is a group of formula

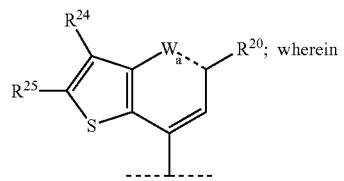

wherein

W is N; the dotted line "a" is a double bond;

$R^{20}$ is —O—CH$_2$CH$_3$;

$R^{24}$ is H or CH$_3$; and $R^{25}$ is H; and

X is O; and $R^3$ is selected from cyclopentyl,

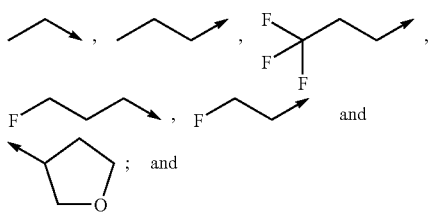

linker D is a 5 carbon atom chain; and
the dotted line "b" is a single bond or a double bond in the Z (cis) configuration.

18. A pharmaceutical composition comprising an anti-hepatitis C virally effective amount of a compound according to claim 1 or a pharmaceutically acceptable salt or ester thereof, and a pharmaceutically acceptable carrier medium or auxiliary agent.

19. The pharmaceutical composition according to claim 18 further comprising a therapeutically effective amount of at least one other antiviral agent.

20. The pharmaceutical composition according to claim 19, wherein said antiviral agent is ribavirin.

21. The pharmaceutical composition according to claim 19, wherein said antiviral agent is selected from an other anti-HCV agent, HIV inhibitor, HAV inhibitor and HBV inhibitor.

22. The pharmaceutical composition according to claim 21, wherein said other anti-HCV agent is selected from the group consisting of immunomodulatory agents, other inhibitors of HCV NS3 protease, inhibitors of HCV polymerase and inhibitors of another target in the HCV life cycle.

23. The pharmaceutical composition according to claim 22, wherein said immunomodulatory agent is selected from α-interferon, γ-interferon and pegylated α-interferon.

24. The pharmaceutical composition according to claim 22, wherein said inhibitor of another target in the HCV life cycle is selected from inhibitors of: helicase, NS2/3 protease and internal ribosome entry site (IRES).

25. A method for the treatment of a hepatitis C viral infection in a mammal comprising administering to the mammal an anti-hepatitis C virally effective amount of a compound according to claim 1, or a pharmaceutically acceptable salt or ester thereof.

26. A method for the treatment of a hepatitis C viral infection in a mammal comprising administering to the mammal an anti-hepatitis C virally effective amount of a combination of a compound according to claim 1, or a pharmaceutically acceptable salt or ester thereof, and at least one other antiviral agent.

27. The method according to claim 26, wherein said antiviral agent is ribavirin.

28. The method according to claim 26, wherein said other antiviral agent is selected from an other anti-HCV agent, HIV inhibitor, HAV inhibitor and HBV inhibitor.

29. The method according to claim 28, wherein said other anti-HCV agent is selected from immunomodulatory agents, other inhibitors of HCV NS3 protease, inhibitors of HCV polymerase and inhibitors of another target in the HCV life cycle.

30. The method according to claim 29, wherein said immunomodulatory agent is selected from α-interferon, γ-interferon and pegylated α-interferon.

31. The method according to claim 29, wherein said inhibitor of another target in the HCV life cycle is selected from inhibitors of: helicase, NS2/3 protease and internal ribosome entry site (IRES).

32. A method of inhibiting the replication of hepatitis C virus by exposing the virus to a hepatitis C viral NS3 protease inhibiting amount of a compound according to claim 1, or a pharmaceutically acceptable salt or ester thereof.

33. An article of manufacture comprising
a composition effective to treat an HCV infection or to inhibit the NS3 protease of HCV and
packaging material comprising a label which indicates that the composition can be used to treat infection by the hepatitis C virus,
wherein said composition comprises a compound according to claim 1 or a pharmaceutically acceptable salt or ester thereof.

34. The compound according to claim 1, which is selected from the group consisting of compounds of the formula:

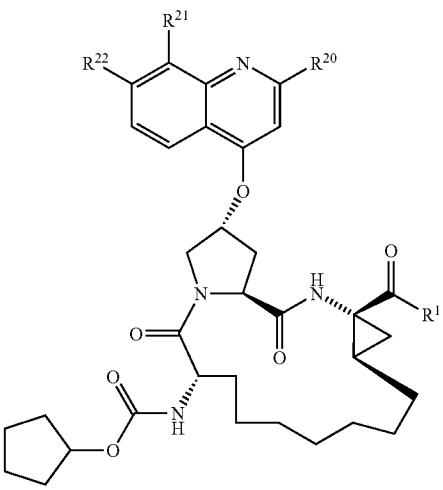

wherein $R^1$, $R^{20}$, $R^{21}$ and $R^{22}$ are defined as follows: in the table below:

$R^1$ is

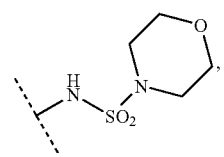

$R^{20}$ is —OEt, $R^{21}$ is Br and $R^{22}$ is —OMe;
$R^1$ is

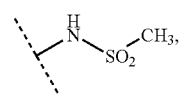

$R^{20}$ is —OEt, $R^{21}$ is Br and $R^{22}$ is —OMe;
$R^1$ is

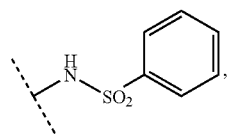

$R^{20}$ is

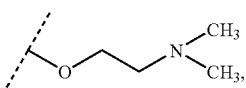

$R^{21}$ is Cl and $R^{22}$ is H;
$R^1$ is

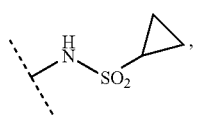

$R^{20}$ is —SCH$_2$CH$_2$CH$_3$, $R^{21}$ is Cl and $R^{22}$ H; and
$R^1$ is

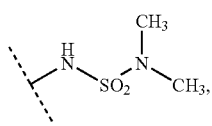

$R^{20}$ is —OEt, $R^{21}$ is —SEt and $R^{22}$ is H.

35. The compound according to claim 1 of the formula:

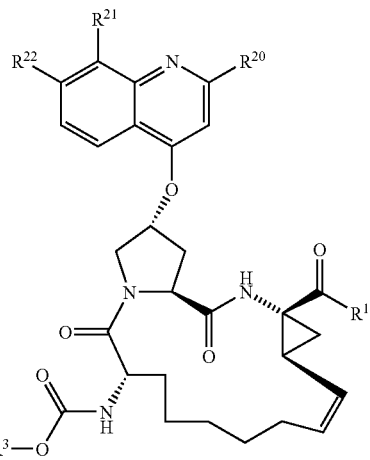

wherein $R^1$ is

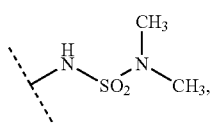

$R^{20}$ is —OEt, $R^{21}$ is Me, $R^{22}$ is H and $R^3$ is

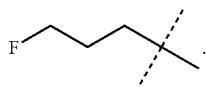

36. The compound according to claim 1, which is a compound of the formula:

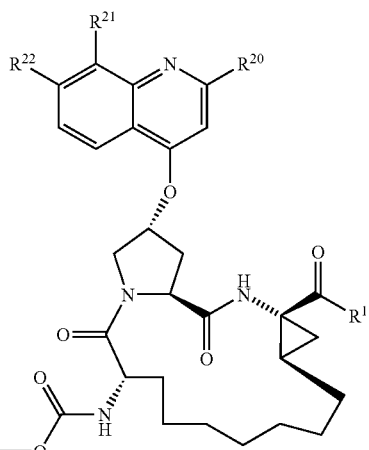

wherein $R^1$ is

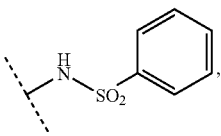

$R^{20}$ is —OEt, $R^{21}$ is CH$_3$ and $R^{22}$ H; or
$R^1$ is

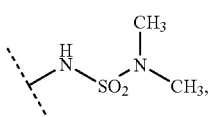

$R^{20}$ is —OEt, $R^{21}$ is CH$_3$ and $R^{22}$ is —OMe.

37. The compound according to claim 1 wherein $R^1$ is NHSO$_2$R$^{11}$; wherein
  $R^{11}$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
   a) each of which optionally being mono-, di- or tri-substituted with substituents each independently selected from fluorine and methyl; and
   b) each of which optionally being mono- or disubstituted with substituents each independently selected from hydroxy, trifluoromethyl, methoxy, phenoxy and trifluoromethoxy; and c) each of which optionally being monosubstituted with a substituent selected from chlorine, bromine, cyano, nitro, -CO-NH$_2$, -CO-NHCH$_3$, -CO-N(CH$_3$)$_2$, -NH$_2$, -NH(CH$_3$) and -N(CH$_3$)$_2$;
wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl,
benzothienyl, piperidinyl, piperazinyl, morpholinyl, triazolyl, tetrazolyl, and

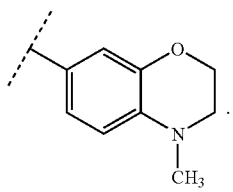

38. The compound according to claim 1 wherein R$^1$ is NHSO$_2$R$^{11}$; wherein
R$^{11}$ is selected from cyclopropyl, cyclobutyl, cyclopentyl and cyclohexyl;
a) each of which optionally being mono-, di- or tri-substituted with fluorine; and
b) each of which optionally being mono- or disubstituted with substituents selected from hydroxy, methoxy and trifluoromethoxy; and
c) each of which optionally being monosubstituted with a substituent selected from chlorine, bromine, cyano, nitro, -CO-NH$_2$, -CO-NHCH$_3$, -CO-N(CH$_3$)$_2$, -NH$_2$, -NH(CH$_3$) and -N(CH$_3$)$_2$; and
d) each of which being optionally substituted with one or more (C$_{1-8}$)alkyl, wherein each (C$_{1-8}$)alkyl is independently optionally substituted with one or more substituents each independently selected from -O-(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O-, wherein each of said aryl and aryloxy is optionally substituted with (C$_{1-6}$)alkyl.

39. The compound according to claim 1 wherein R$^1$ is NHSO$_2$R$^{11}$ wherein R$^{11}$ is -N(R$^{11a}$)(R$^{11b}$); wherein
R$^{11a}$ and R$^{11b}$ are each independently selected from H, methyl, ethyl, propyl, 1-methylethyl, cyclopropyl, cyclobutyl, cyclopentyl, cyclohexyl, phenyl and phenylmethyl; wherein said methyl, ethyl, propyl, 1-methylethyl, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O-(C$_{1-4}$)alkyl, -NH$_2$, -NH(C$_{1-4}$)alkyl, -N((C$_{1-4}$)alkyl)$_2$, -CO-NH$_2$, -CO-NH(C$_{1-4}$)alkyl, -CO-N((C$_{1-4}$)alkyl)$_2$, -COOH, and -COO(C$_{1-4}$)alkyl; or
R$^{11a}$ and R$^{11b}$ are linked, together with the nitrogen to which they are bonded, to form a 3- 4-, 5- or 6-membered monocyclic saturated or unsaturated heterocycle, optionally containing from one to three further heteroatoms each independently selected from N, S and O, and optionally substituted with one, two or three substituents each independently selected from halogen, (C$_{1-4}$)alkyl, hydroxy, cyano, O-(C$_{1-4}$)alkyl, -NH$_2$, -NH(C$_{1-4}$)alkyl, -N((C$_{1-4}$)alkyl)$_2$, -CO-NH$_2$, -CO-NH(C$_{1-4}$)alkyl, -CO-N((C$_{1-4}$)alkyl)$_2$, -COOH, and -COO(C$_{1-4}$)alkyl.

40. The compound according to claim 1 wherein R$^1$ is NHSO$_2$R$^{11}$, wherein the group R$^{11}$ is selected from methyl, ethyl, 1-methylethyl, propyl, ethenyl, cyclopropyl, cyclobutyl, cyclopentyl, phenyl,

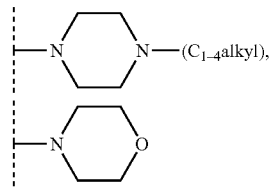

and -N(CH$_3$)$_2$; wherein said phenyl is optionally monosubstituted with halogen and wherein said cyclopropyl is optionally substituted at the 1-position with methyl, ethyl, propyl or butyl, each of said methyl, ethyl, propyl and butyl being optionally further substituted with phenyl, (C$_{3-6}$)cycloalkyl, (C$_{2-6}$)alkenyl or (C$_{1-4}$)alkoxy.

41. The compound according to claim 1, wherein R$^2$ is a group of formula:

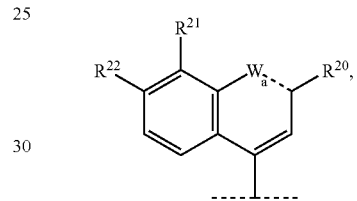

wherein
R$^{21}$ and R$^{22}$ are defined as in claim 1; R$^{20}$ is oxo; W is NR$^{23}$ wherein R$^{23}$ is Me, Et, -CH$_2$CH=CH$_2$ or H; and the dotted line "a" is a single bond.

42. The compound according to claim 1 wherein R$^2$ is a group of formula:

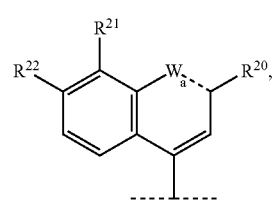

wherein
W, R$^{20}$, R$^{24}$, R$^{25}$ and the dotted line "a" are defined as in claim 1.

43. The compound according to claim 42, wherein W is N; the dotted line "a" is a double bond; and R$^{20}$ is H, OH, halogen, or Y$^1$-R$^{20a}$ wherein
Y$^1$ is a bond, O, S, or NR$^{20b}$;
R$^{20a}$ is selected from the group consisting of: (C$_{1-8}$)alkyl, (C$_{2-8}$)alkenyl, (C$_{2-8}$)alkynyl and (C$_{3-7}$)cycloalkyl, each of said alkyl, alkenyl, alkynyl and cycloalkyl being optionally substituted with one, two or three substituents, each independently selected from:
halogen, (C$_{1-6}$)alkyl, (C$_{3-7}$)cycloalkyl, Het, -O-(C$_{1-6}$)alkyl, -O-(C$_{3-6}$)cycloalkyl, -NH$_2$, -NH(C$_{1-4}$)alkyl and -N((C$_{1-4}$)alkyl)$_2$; and
R$^{20b}$ is H, (C$_{1-6}$)alkyl or (C$_{3-6}$)cycloalkyl.

44. The compound according to claim 43, wherein $R^{20}$ is $Y^1$-$R^{20a}$, wherein $Y^1$ is O and $R^{20a}$ is $(C_{1-8})$alkyl.

45. The compound according to claim 43, wherein $R^{24}$ is H or $(C_{1-6})$alkyl.

46. The compound according to claim 43, wherein $R^{25}$ is H.

* * * * *